United States Patent [19]

Wiedeman et al.

[11] Patent Number: 5,386,011
[45] Date of Patent: Jan. 31, 1995

[54] HEXAPEPTIDE ANAPHYLATOXIN-RECEPTOR LIGANDS

[75] Inventors: Paul E. Wiedeman; Megumi Kawai; Jay R. Luly; Yat S. Or, all of Libertyville; Rolf Wagner, Gurnee, all of Ill.

[73] Assignee: Abbott Laboratories, Abbott Park, Ill.

[21] Appl. No.: 634,641

[22] Filed: Dec. 27, 1990

[51] Int. Cl.$^6$ .................. A61K 37/00; A61K 37/02; C07K 5/00; C07K 7/00
[52] U.S. Cl. ..................... 530/329; 530/317; 530/328; 530/327
[58] Field of Search ............. 530/317, 328, 327, 329; 514/11, 16, 17

[56] References Cited

FOREIGN PATENT DOCUMENTS 9009162 8/1990 WIPO .

OTHER PUBLICATIONS

Swerlick et al., *The Journal of Immunology*, vol. 140, No. 7, Apr. 1988, pp. 2376–2381.
Mollison et al, *PNAS*, vol. 86, pp. 292–296, Jan. 1989.
Hartung et al., The Journal of Immunology, vol. 130, No. 3, Mar. 1983, pp. 1345–1349.
Kings et al., Immunology Letters, 8, 1984 pp. 23–25.
Köhl et al., Eur. J. Immunol., 1990, vol. 20, pp. 1463–1468.

*Primary Examiner*—Robert J. Hill, Jr.
*Assistant Examiner*—A. M. Davenport
*Attorney, Agent, or Firm*—Jerry F. Janssen

[57] ABSTRACT

Oligopeptide compounds or oligopeptide analogue compounds of the formula A-B-D-E-G-J-L-M-Q are ligands for the anaphylatoxin receptor and are useful in the treatment of inflammatory disease states.

Also disclosed are anaphylatoxin receptor ligand compositions and a method for modulating anaphylatoxin activity.

12 Claims, No Drawings

HEXAPEPTIDE ANAPHYLATOXIN-RECEPTOR LIGANDS

TECHNICAL FIELD

This invention relates to organic compounds that modulate anaphylatoxin activity. It also relates to methods and compositions for modulating anaphylatoxin activity in human and animal hosts in need of such treatment.

BACKGROUND OF THE INVENTION

A wide variety of conditions including infection by bacteria, viruses or fungi, infiltration by cancer cells, allergic or autoimmune disorders and physically- or chemically-induced trauma causes an inflammatory response in humans. In all of these diseases and conditions in man and in most mammals, activation of the complement system (a set of proteins, regulatory factors and proteolytic enzymes) via either the classical or the alternative pathway results in the generation of biologically active peptides which serve to amplify and exacerbate the resulting inflammation. The most active peptide, anaphylatoxin C5a, a 74-amino acid polypeptide, is generated by cleavage of the alpha-chain of native C5 at a specific site by convertases (proteolytic enzymes) of the blood complement system as well as by enzymes of the coagulation system. C5a exists in vivo in two biologically active forms. Once it is liberated from C5, the carboxyl terminal arginine of C5a is rapidly removed by carboxypeptidase-N, leaving the des-Arg derivative. Although C5a des-Arg is less active than C5a, both are potent inflammatory mediators at concentrations likely to be generated in vivo (Fernandez, H. N.; Henson, P. M.; Otani, A.; Hugli, T. E. *J. Immunol.* 1978, 120, 109.). Together, these peptides along with C3a, C4a, and their des-Arg degradation products, collectively described herein as anaphylatoxin, are capable of triggering diverse inflammatory reactions.

Among the various cell types, the neutrophil response to C5a is the best defined. Cell surface receptors specific for C5a have been demonstrated on the neutrophil (Chenoweth, D. E.; Hugli, T. E. *Proc. Natl. Acad. Sci. U.S.A.* 1978, 75, 3943–3947. Huey, R.; Hugli, T. E. *J. Immunol.* 1985, 135, 2063–2068. Rollins, T. E.; Springer, M. S. *J. Biol. Chem.* 1985, 260, 7157–7160.), and the ligand-receptor interaction promotes human polymorpho-nuclear leukocyte (PMN) migration in a directed fashion (chemotaxis), adherence, oxidative burst, and granular enzyme release from these cells (Hugli, T. E. *Springer Semin. Immunopathol.* 1984, 7, 193–219.). The interaction of C5a with PMN and other target cells and tissues results in increased histamine release, vascular permeability, smooth muscle contraction, and an influx into tissues of inflammatory cells, including neutrophils, eosinophils, and basophils (Hugli, T. E. *Springer Semin. Immunopathol.* 1984, 7, 193–219.). C5a may also be important in mediating inflammatory effects of phagocytic mononuclear cells that accumulate at sites of chronic inflammation (Allison, A. C.; Ferluga, J.; Prydz, H.; Scherlemmer, H. U. *Agents and Actions* 1978, 8, 27.). C5a and C5a des-Arg can induce chemotaxis in monocytes (Ward, P. A. *J. Exp. Med.* 1968, 128, 1201. Snyderman, R.; Shin, H. S.; Dannenberg, A. C. *J. Immunol.* 1972, 109, 896.) and cause them to release lysosomal enzymes (McCarthy, K.; Henson, P. S. *J. Immunol.* 1979, 123, 2511.) in a manner analogous to the neutrophil responses elicited by these agents. Recent studies suggest that C5a may have an immunoregulatory role by enhancing antibody particularly at sites of inflammation (Morgan, E. L.; Weigle, W. O.; Hugli, T. E. *J. Exp. Med.* 1982, 155, 1412. Weigle, W. O.; Morgan, E. L.; Goodman, M. G.; Chenoweth, D. E.; Hugli, T. E. *Federation Proc.* 1982, 41, 3099. Morgan, E. L.; Weigle, W. O.; Hugli, T. E. *Federation Proc.* 1984, 43, 2543.).

C5a and C5a des-Arg play important roles in host defenses against bacterial infections and possibly in the mediation of some pathologic lesions such as the leukocyte infiltration seen in the lungs during acute respiratory distress syndrome. This mechanism seems to play a role in different pathological situations like pulmonary distress during hemodialysis, leukophoresis, cardiopulmonary bypass, and in acute myocardial infarction. Complement activation has been postulated to play an important pathological role in rheumatoid arthritis, serum sickness, systemic lupus erythematosus, ulcerative colitis, and forms of hepatic cirrhosis, chronic hepatitis, and glomerulonephritis, in certain shock states, during hemodialysis, and cardiopulmonary bypass, acute pancreatitis, myocardial infarction (which may be worsened by C5a-induced leuko-embolization following the interaction of complement with atheromatous plaques), asthma, bronchoconstriction, some auto-allergic diseases, transplant rejection, and post-viral encephalopathies.

By serving as antagonists by binding to and blocking the anaphylatoxin receptor, certain compounds of the present invention can reduce or prevent anaphylatoxin-mediated inflammation. Other compounds of the present invention are agonists that mimic anaphylatoxin activity, and assist the body in building its defense mechanism against invasion by infectious agents and malignancy. Additionally, these compounds may influence the immunoregulatory effects of anaphylatoxin. The possible involvement of anaphylatoxin in a wide range of diseases, as indicated by these examples, suggests that anaphylatoxin receptor ligands could have clinical applications for the treatment and prevention of the above-mentioned pathological conditions.

SUMMARY OF THE INVENTION

In accordance with the principal embodiment of the present invention, there are provided anaphylotoxin activity modifying compounds of the formula A-B-D-E-G-J-L-M-Q and the pharmaceutically acceptable salts, esters, or amides thereof.

In the generic formula given above, the groups A through Q have the following values:

A is $R_1$-$R_2$-$R_3$;
B is selected from $R_4$-$R_5$-$R_6$, $R_{35}$ and $R_{37}$;
D is selected from $R_7$-$R_8$-$R_9$ and $R_{35}$;
E is selected from $R_{10}$-$R_{11}$-$R_{12}$ and $R_{35}$;
G is selected from $R_{13}$-$R_{14}$-$R_{15}$ and $R_{35}$;
J is selected from $R_{16}$-$R_{17}$-$R_{18}$ and $R_{35}$;
T is selected from $R_{19}$-$R_{20}$-$R_{21}$ and $R_{35}$;
M is selected from a valence bond, $R_{22}$-$R_{23}$-$R_{24}$, and $R_{35}$;
Q is $R_{25}$-$R_{26}$-$R_{27}$;

The group $R_1$ is selected from the group consisting of aryl, lower alkyl, arylalkyl and hydrogen.

$R_2$ is selected from the group consisting of >$CR_{99}R_{100}$ and oxygen, with the proviso that when $R_2$ is oxygen, $R_1$ is aryl, lower alkyl or arylalkyl.

$R_3$ is selected from the group consisting of $>C=O$ and $>CH_2$, with the proviso that when $R_3$ is $>CH_2$ then $R_2$ cannot be oxygen.

$R_4$ is $>NR_{101}$ where $R_{101}$ is hydrogen, lower alkyl, arylalkyl or alkenyl.

$R_5$ is selected from the group consisting of $>CR_{201}R_{202}$, $>NR_{203}$, $>C=CR_{205}R_{206}$, existing in either the Z- or E-configuration, and substituted cyclopropyl of the formula

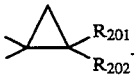

$R_6$, $R_9$, $R_{12}$, $R_{15}$, $R_{18}$, $R_{21}$ and $R_{24}$ are $>C=O$
$R_7$, $R_{10}$, $R_{13}$, $R_{16}$, $R_{19}$, and $R_{22}$, are $>NH$.

$R_8$ is selected from the group consisting of $>CR_{210}R_{211}$, $>NR_{213}$, $>C=CR_{215}R_{216}$, existing in either the Z- or E-configuration, and substituted cyclopropyl of the formula

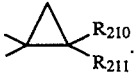

$R_{11}$ is selected from the group consisting of $>CR_{220}R_{221}$, $>NR_{223}$, $>C=CR_{225}R_{226}$, existing in either the Z- or E-configuration, and substituted cyclopropyl of the formula

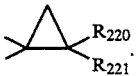

$R_{14}$ is selected from the group consisting of $>CR_{230}R_{231}$, $>NR_{233}$, $>C=CR_{235}R_{236}$, existing in either the Z- or E-configuration, and substituted cyclopropyl of the formula

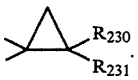

$R_{17}$ is selected from the group consisting of $>CR_{301}R_{302}$, $>NR_{303}$, $>C=CR_{305}R_{306}$, existing in either the Z- or E-configuration, and substituted cyclopropyl of the formula

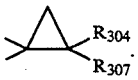

$R_{20}$ is selected from the group consisting of $>CR_{310}R_{311}$, $>C=CR_{315}R_{316}$, existing in either the Z- or E-configuration, and substituted cyclopropyl of the formula

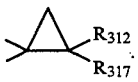

$R_{23}$ is selected from the group consisting of $>CR_{320}R_{321}$, $>C=CR_{325}R_{326}$, existing in either the Z- or E-configuration, and substituted cyclopropyl of the formula

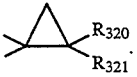

$R_{25}$ is selected from the group consisting of $>O$ and $>NR_{109}$, where $R_{109}$ is selected from hydrogen, lower alkyl and arylalkyl.

$R_{26}$ is selected from the group consisting of hydrogen, lower alkyl, arylalkyl, and $>NR_{110}$ where $R_{110}$ is selected from hydrogen, lower alkyl, aryl, and arylalkyl, with the provisos that (i) when $R_{25}$ is $>O$ then $R_{26}$ is lower alkyl, and (ii) when $R_{26}$ is hydrogen, lower alkyl, or arylalkyl then $R_{27}$ is absent.

$R_{27}$ is selected from the group consisting of hydrogen, lower alkyl, or aryl.

$R_{35}$ is a group having the structure

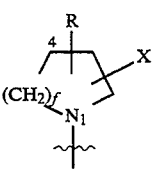

where f is an integer of 0 to 3, and X is $>C=O$. R is selected from hydrogen and lower alkyl, with the provisos that (i) when f is 0, X is at C-2 and R is at C-3 or C-4; (ii) when f is 1, X is at C-2 and R is at C-3, C-4 or C-5 and C-3,4 are saturated or unsaturated; (iii) when f is 2, X is at C-2, C-3 or C-4 and R is at C-2, C-3, C-4, C-5 or C-6 when the position is unoccupied by X and C-3,4 or C-4,5 are saturated or unsaturated and (iv) when f is 3, X is at C-2, C-3 or C-4 and R is at C-2, C-3, C-4, C-5, C-6 or C-7 when the position is unoccupied by X and C-3,4 or C-4,5 or C-5, 6 are saturated or unsaturated.

$R_{37}$ is a group having the structure

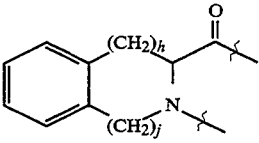

where h is 0 or 1 and j is 0 or 1 with the proviso that either h or j must be 1.

$R_1$ and $R_2$, taken together, optionally may represent a group selected from aryl or hydrogen.

$R_{26}$ and $R_{27}$, taken together, optionally represent a group selected from hydrogen, with the proviso that when $R_{25}$ is $>O$ then $R_{26}$ and $R_{27}$, taken together, represent hydrogen, lower alkyl or arylalkyl.

$R_1$, $R_2$ and $R_3$, taken together, optionally represent a group selected from lower alkyl, arylalkyl, alkenyl, hydrogen, or an N-terminal protecting group.

$R_{205}$, $R_{206}$, $R_{215}$, $R_{216}$, $R_{225}$, $R_{226}$, $R_{235}$, $R_{236}$, $R_{305}$, and $R_{306}$ are independently selected from the group consisting of hydrogen, lower alkyl, aryl, arylalkyl (Arylalkyl is excluded from $R_{305}$ and $R_{306}$ when $R_{19}$-$R_{20}$-$R_{21}$ represents an L-arginyl residue.), (cycloalkyl)alkyl, amidoalkyl (For $R_{305}$ and $R_{306}$, benzoyl amides and their heterocyclic variants are excluded when $R_{19}$-$R_{20}$-$R_{21}$ represents an L-arginyl residue.), (carboxyamido) alkyl (For $R_{305}$ and $R_{306}$, aniline amides and their heterocyclic variants are excluded when $R_{19}$-$R_{20}$-$R_{21}$ represents an L-arginyl residue.), ureidoalkyl, and (heterocyclic)alkyl (For $R_{305}$ and $R_{306}$, when, $R_{19}$-$R_{20}$-$R_{21}$ represents an L-arginyl residue, then the heterocycle can only be separated by one methylene unit from the alpha-carbon.).

$R_{315}$ and $R_{316}$ are independently selected from the group consisting of hydrogen, lower alkyl, aryl, arylalkyl (Arylalkyl is excluded when $R_{22}$-$R_{23}$-$R_{24}$ represents an L-arginyl residue.), and (cycloalkyl) alkyl;

$R_{99}$, $R_{202}$, $R_{211}$, $R_{221}$, $R_{231}$, $R_{302}$, $R_{311}$ and $R_{321}$ are independently selected from hydrogen, lower alkyl and arylalkyl. For $R_{302}$ and $R_{311}$, arylalkyl is limited to benzyl when $R_{19}$-$R_{20}$-$R_{21}$ and $R_{22}$-$R_{23}$-$R_{24}$ respectively represent an L-arginyl residue.

$R_{100}$ is hydrogen or lower alkyl.

$R_{201}$ is selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido)alkyl, (carboxyhydrazino)alkyl, ureidoalkyl, (heterocyclic)alkyl, (thioalkoxy)alkyl, and sulfhydrylalkyl.

$R_{203}$, $R_{213}$, $R_{223}$, $R_{233}$, and $R_{303}$ are independently selected from the group consisting of hydrogen, lower alkyl, alkenyl, arylalkyl (Arylalkyl is limited to benzyl at $R_{303}$ when $R_{19}$-$R_{20}$-$R_{21}$ represents an L-arginyl residue.), (cycloalkyl)alkyl, aminoalkyl (Aryl and arylalkyl amines are excluded from $R_{303}$ when $R_{19}$-$R_{20}$-$R_{21}$ represents an L-arginyl residue.), amidoalkyl (Benzoyl amides and their heterocyclic variants are excluded from $R_{303}$ when $R_{19}$-$R_{20}$-$R_{21}$ represents an L-arginyl residue.), hydroxyalkyl, guanidinoalkyl, carboxyalkyl, (carboxyamido) alkyl (Aniline amides and their heterocyclic variants are excluded from $R_{303}$ when $R_{19}$-$R_{20}$-$R_{21}$ represents an L-arginyl residue.), (carboxyhydrazino)alkyl, ureidoalkyl, (heterocyclic) alkyl (When $R_{19}$-$R_{20}$-$R_{21}$ represents an L-arginyl residue, then the heterocycle at $R_{303}$ can only be separated by one methylene unit from the alpha-carbon.), (thioalkoxy)alkyl and sulfhydrylalkyl, with the proviso that none of the groups $R_{203}$, $R_{213}$, $R_{223}$, $R_{233}$, or $R_{303}$ may be a vinyl group or have a heteroatom directly attached to the nitrogen or separated from it by one methylene unit.

$R_{210}$ is selected from the group consisting of hydrogen, lower alkyl, alkenyl, aryl, arylalkyl, (cycloalkyl)alkyl, aminoalkyl, amidinoalkyl, amidoalkyl, hydroxyalkyl, guanidinoalkyl, carboxyalkyl, (carboxyamido)alkyl, ureidoalkyl, (carboxyhydrazino)alkyl, (heterocyclic)alkyl, (thioalkoxy)alkyl and sulfhydrylalkyl.

$R_{220}$ is independently selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido) alkyl, (carboxyhydrazino) alkyl, ureidoalkyl, (heterocyclic) alkyl, (thioalkoxy) alkyl and sulfhydrylalkyl.

$R_{230}$ is independently selected from the group consisting of hydrogen, lower alkyl, alkenyl, aryl, arylalkyl, (cycloalkyl)alkyl, aminoalkyl, amidoalkyl, hydroxyalkyl, guanidinoalkyl, carboxyalkyl, (carboxyamido) alkyl, (carboxyhydrazino) alkyl, ureidoalkyl, (heterocyclic) alkyl, (thioalkoxy) alkyl and sulfhydrylalkyl.

$R_{301}$ is independently selected from the group consisting of hydrogen, lower alkyl, alkenyl, aryl, arylalkyl (Arylalkyl is limited to benzyl when $R_{19}$-$R_{20}$-$R_{21}$ represents an L-arginyl residue.), (cycloalkyl)alkyl, aminoalkyl (Aryl and arylalkyl amines are excluded when $R_{19}$-$R_{20}$-$R_{21}$ represents an L-arginyl residue.), amidoalkyl (Benzoyl amides and their heterocyclic variants are excluded when $R_{19}$-$R_{20}$-$R_{21}$ represents an L-arginyl residue.), hydroxyalkyl, guanidinoalkyl, carboxyalkyl, (carboxyamido)alkyl (Aniline amides of aspartyl residues and heterocyclic variants are excluded when $R_{19}$-$R_{20}$-$R_{21}$ represents an L-arginyl residue.), (carboxyhydrazino) alkyl, ureidoalkyl, (heterocyclic) alkyl (When $R_{19}$-$R_{20}$-$R_{21}$ represents an L-arginyl residue, then the heterocycle can only be separated by one methylene unit from the alpha-carbon.), (thioalkoxy) alkyl and sulfhydrylalkyl.

$R_{304}$ is independently selected from the group consisting of hydrogen, lower alkyl, alkenyl, aryl, arylalkyl (Arylalkyl is excluded when $R_{19}$-$R_{20}$-$R_{21}$ represents an L-arginyl residue.), (cycloalkyl) alkyl, aminoalkyl (Aryl and arylalkyl amines are excluded when $R_{19}$-$R_{20}$-$R_{21}$ represents an L-arginyl residue.), amidoalkyl (Benzoyl amides and their heterocyclic variants are excluded when $R_{19}$-$R_{20}$-$R_{21}$ represents an L-arginyl residue.), hydroxyalkyl, guanidinoalkyl, carboxyalkyl, (carboxyamido)alkyl (Aniline amides and heterocyclic variants are excluded when $R_{19}$-$R_{20}$-$R_{21}$ represents an L-arginyl residue.), (carboxyhydrazino)alkyl, ureidoalkyl, (heterocyclic)alkyl (When $R_{19}$-$R_{20}$-$R_{21}$ represents an L-arginyl residue, then the heterocycle must be directly attached to the cyclopropyl ring.), (thioalkoxy)alkyl and sulfhydrylalkyl.

$R_{307}$ and $R_{317}$ are independently selected from hydrogen; lower alkyl; aryl and arylalkyl, wherein arylalkyl is excluded for $R_{307}$ and $R_{317}$ when $R_{19}$-$R_{20}$-$R_{21}$ and $R_{22}$-$R_{23}$-$R_{24}$ respectively represent an L-arginyl residue.

$R_{310}$ is independently selected from the group consisting of hydrogen, lower alkyl, alkenyl, aryl, arylalkyl (Arylalkyl is limited to benzyl when $R_{22}$-$R_{23}$-$R_{24}$ represents an L-arginyl residue.), (cycloalkyl) alkyl, aminoalkyl (Aryl and arylalkyl amines are excluded when $R_{22}$-$R_{23}$-$R_{24}$ represents an L-arginyl residue.), amidoalkyl (When $R_{22}$-$R_{23}$-$R_{24}$ represents an L-arginyl residue, then benzoyl amides and their heterocyclic variants are excluded.), hydroxyalkyl, guanidinoalkyl, (carboxyamido)alkyl (Aniline amides of aspartyl residues and heterocyclic variants are excluded when $R_{22}$-$R_{23}$-$R_{24}$ represents an L-arginyl residue.), (carboxyhydrazino)alkyl, ureidoalkyl, (heterocyclic) alkyl (When $R_{22}$-$R_{23}$-$R_{24}$ represents an L-arginyl residue, then the heterocycle can only be separated by one methylene unit from the alpha-carbon.), and sulfhydrylalkyl.

$R_{312}$ is independently selected from the group consisting of hydrogen, lower alkyl, alkenyl, aryl, arylalkyl (Arylalkyl is excluded when $R_{22}$-$R_{23}$-$R_{24}$ represents an L-arginyl residue.), (cycloalkyl)alkyl, aminoalkyl (Aryl and arylalkyl amines are excluded when $R_{22}$-$R_{23}$-$R_{24}$ represents an L-arginyl residue.), amidoalkyl (When $R_{22}$-$R_{23}$-$R_{24}$ represents an L-arginyl residue, then benzoyl amides and their heterocyclic variants are excluded.), hydroxyalkyl, guanidinoalkyl, (carboxyamido)alkyl (Aniline amides and heterocyclic variants are excluded when $R_{22}$-$R_{23}$-$R_{24}$ represents an L-arginyl residue.), (carboxyhydrazino) alkyl, ureidoalkyl, (heterocyclic)alkyl (When $R_{22}$-$R_{23}$-$R_{24}$ represents ah L-arginyl residue, then the heterocycle must be directly attached to the cyclopropyl ring.), and sulfhydrylalkyl.

$R_{320}$ is selected from the group consisting of hydrogen, lower alkyl, aryl, arylalkyl, alkenyl, aminoalkyl, (cycloalkyl)alkyl and guanidinoalkyl.

$R_{325}$ and $R_{326}$ are independently selected from the group consisting of hydrogen, lower alkyl, aryl, arylalkyl, and (cycloalkyl)alkyl.

$R_{201}$ and $R_{202}$, $R_{210}$ and $R_{211}$, $R_{220}$ and $R_{221}$, $R_{230}$ and $R_{231}$, $R_{301}$ and $R_{302}$, $R_{310}$ and $R_{311}$, $R_{320}$ and $R_{321}$, each pair taken together, independently may optionally represent —$(CH_2)_z$— where z is an integer of from 2 to 6.

$R_{201}$ and $R_{202}$, $R_{210}$ and $R_{211}$, $R_{220}$ and $R_{221}$, $R_{230}$ and $R_{231}$, $R_{301}$ and $R_{302}$, $R_{310}$ and $R_{311}$, and $R_{320}$ and $R_{321}$, each pair taken together, independently may optionally represent —$CH_2C_6H_4CH_2$— where the two methylene chains are in an ortho configuration.

All of the foregoing definitions are with the provisos that, in the compounds of the present invention, (i) when more than one sulfhydrylalkyl is present in the compound, the compound exists in the oxidized disulfide form producing a cyclic molecule, or the two sulfhydryl moieties are connected by a $C_2$ to $C_8$ alkylene chain and (ii) when the compound contains a free amino group and carboxyl group, they can be cyclized to give the corresponding lactam.

The present invention also relates to a method for modulating anaphylatoxin activity in a mammal in need of such treatment, comprising administering to the mammal a therapeutically effective amount of a compound of claim 1.

The invention further relates to an anaphylatoxin modulating compositions comprising a pharmaceutical carrier and a therapeutically effective amount of a compound of claim 1.

DETAILED DESCRIPTION

As discussed above, C5a is the most active of a class of biologically active peptides which serve to amplify and exacerbate inflammation. While C5a contains 74 amino acid residues, it has been found in accordance with the present invention that oligopeptides containing as few as six amino acid residues are also actively bound by C5a receptors. Moreover, it has been found that peptidomimetic compounds (i.e. compounds which mimic the activity of peptides) in which certain groups replace the G-carbon in oligopeptides are also actively bound by C5a receptors.

The chemical structures of the compounds of the present invention are best understood by reference to the following structural formula in which it is understood that the segments are joined serially at the free valence bonds to form the compound A-B-D-E-G-J-L-M-Q.

In one embodiment M is a valence bond and none of the residues is proline.

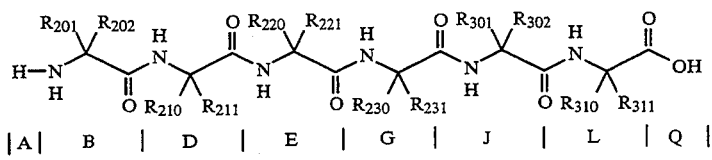

In another embodiment M is a valence bond and E is proline, ($R_{35}$ where F=1 and R=H).

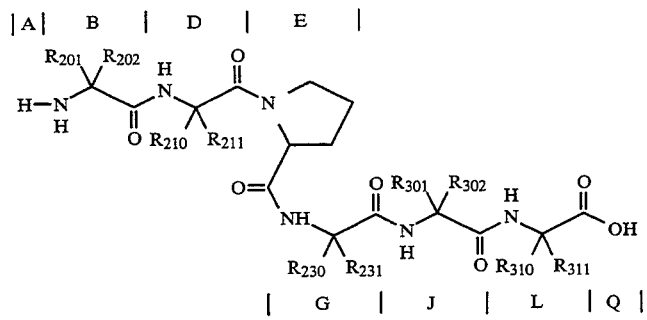

In another embodiment if more than one sulfhydrylalkyl is present in the compound, then the compound can exist in the oxidized disulfide form producing a cyclic molecule.

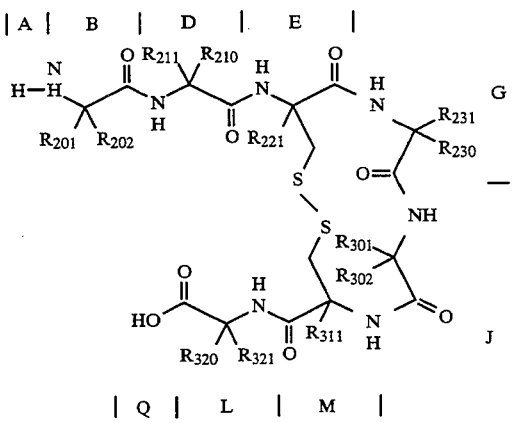

In another embodiment if the compound contains a free amino group and a free carboxyl group, then they can be cyclized to give the corresponding lactam.

|A| B | D | E | G /

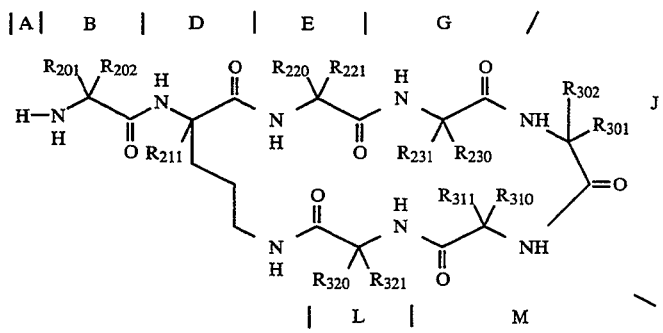

| L | M

As used throughout this specification and the appended claims, the following terms have the meanings specified.

The term "alkyl" as used herein refers to monovalent straight chain or branched chain groups of 1 to 12 carbon atoms, including, but not limited to methyl, ethyl, n-propyl, isopropyl, n-butyl, sec-butyl, isobutyl, tert-butyl, and the like.

The term "lower alkyl" as used herein refers to straight or branched chain alkyl groups containing from 1 to 8 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "alkylene" as used herein refers to divalent groups of from one to twelve carbon atoms derived by the removal of two hydrogen atoms from straight or branched saturated hydrocarbons. Examples include —CH$_2$—, —CH (CH$_3$)—, —C(CH$_3$)$_2$—, —CH(C$_2$H$_5$)—, —CH$_2$CH$_2$—, —CH$_2$CH(CH$_3$)—, —C(CH$_3$)$_2$C(CH$_3$)$_2$—, —CH$_2$CH$_2$CH$_2$— and the like.

The term "alkenyl" as used herein refers to straight or branched chain groups of 2 to 12 carbon atoms containing a carbon-carbon double bond, including, but not limited to ethenyl, 1,propenyl, 2-propenyl, 2-methyl-1-propenyl, 1-butenyl, 2-butenyl, and the like.

The term "cycloalkyl" as used herein refers to cyclic groups, of 3 to 8 carbons, including, but not limited to cyclopropyl, cyclobutyl, cyclopentyl, cyclohexyl, and the like.

The term "(cycloalkyl)alkyl" as used herein refers to a cycloalkyl group appended to a lower alkyl group, including, but not limited to cyclohexylmethyl and cyclohexylethyl.

The term "alkoxy" as used herein refers to an alkyl group as defined above, attached to the remainder of the molecule through an oxygen atom. Alkoxy groups include, for example, methoxy, ethoxy, isopropoxy, n-butoxy, sec-butoxy, isobutoxy, tert-butoxy, and the like.

The term "sulfhydrylalkyl" as used herein refers to a —SH group appended to a lower alkyl group, as previously defined.

The term "protected sulfhydrylalkyl" refers to a sulfhydrylalkyl group, as previously defined, which has been transformed to the corresponding S-acetamidomethyl (S-Acm) or other similar protecting groups such as substituted or unsubstituted arylalkyl or t-butyl as known in the art, including, but not limited to S-phenacetamidomethyl. Typically used sulfhydrylalkyl protecting groups are described in: Gross, E; Meienhofer, J "The Peptides" Volume 3; Academic Press, 1981.

The term "thioalkoxy" as used herein refers to an alkyl group, as previously defined, attached to the remainder of the molecule through a sulfur atom. Examples of thioalkoxy groups include, but are not limited to, thiomethoxy, thioethoxy, thioisopropoxy, n-thiobutoxy, sec-thiobutoxy, isothiobutoxy, tert-thiobutoxy and the like.

The term "(thioalkoxy)alkyl" as used herein refers to a thioalkoxy group, as just defined, appended to a lower alkyl group.

The term "(thioarylalkoxy) alkyl" as used herein refers to a group of the structure R$_{420}$—S— appended to a lower alkyl where R$_{420}$ is an arylalkyl group as defined below.

The term "aryl" as used herein refers to substituted and unsubstituted carbocyclic aromatic groups including, but not limited to phenyl, 1- or 2-naphthyl, fluorenyl, (1,2)-dihydronaphthyl, (1,2,3,4)-tetrahydronaphthyl, indenyl, indanyl, and the like, wherein the aryl group may be substituted with 1, 2, or 3 substituents independently selected from halo, nitro, cyano, C$_1$ to C$_{12}$ alkyl, alkoxy, aroyl and halosubstituted alkyl.

The term "arylalkyl" as used herein refers to an aryl group, as previously defined, appended to an alkyl group, including, but not limited to benzyl, 1- and 2-naphthylmethyl, halobenzyl, alkoxybenzyl, hydroxybenzyl, aminobenzyl, nitrobenzyl, guanidinobenzyl, fluorenylmethyl, phenylmethyl (benzyl), 1-phenylethyl, 2-phenylethyl, 1-naphthylethyl, and the like.

The term "benzyl" as used herein refers specifically to phenyl substituted methyl in which the phenyl group may be substituted with 1, 2, or 3 substituents independently selected from halo, nitro, cyano, alkyl of from one to twelve carbon atoms, alkoxy, aroyl, and halosubstituted alkyl, and the like.

The term "aryloxy" as used herein refers to an aryl group as previously defined, attached to the parent molecular moiety through an oxygen atom. Aryloxy includes, but is not limited to phenoxy, 1-naphthoxy, 2-naphthoxy and the like.

The term "arylalkoxy" as used herein refers to an arylalkyl group as previously defined, attached to the parent molecular moiety through an oxygen atom. Arylalkoxy includes, but is not limited to benzyloxy, 2-phenethyloxy, 1-naphthylmethyloxy and the like.

The term "aroyl" as used herein refers to an aryl group as defined above, attached to the parent molecule through a carbonyl group. Examples include benzoyl and substituted benzoyl.

The term "alkylamino" as used herein refers to a group having the structure -NH(alkyl) where the alkyl portion is as defined above. Alkylamino groups include, for example, methylamino, ethylamino, isopropylamino and the like.

The term "dialkylamino" as used herein refers to a group having the structure —N(alkyl)(alkyl) where the two alkyl groups may be the same or different and are as previously defined.

The term "aminoalkyl" as used herein refers to a group having the structure —$NR_{342}R_{343}$ appended to a lower alkyl group, as previously defined. The groups $R_{342}$ and $R_{343}$ are independently selected from hydrogen, lower alkyl, aryl and arylalkyl. Additionally, $R_{342}$ and $R_{343}$ taken together, may optionally be —$(CH_2)_{mm}$— where mm is an integer of from 2 to 6.

The term "amidinoalkyl" as used herein refers to a group having the structure —$NHC(=NH)R_{350}$ appended to a lower alkyl group, as previously defined. The group $R_{350}$ is independently selected from lower alkyl, aryl, arylalkyl, and (cycloalkyl)alkyl.

The term "amidoalkyl" as used herein refers to a group having the structure —$NR_{344}C(O)R_{345}$ appended to a lower alkyl group, as previously defined. The groups $R_{344}$ and $R_{345}$ are independently selected from hydrogen, lower alkyl, aryl, arylalkyl, and halosubstituted alkyl. Additionally, $R_{344}$ and $R_{345}$ taken together may optionally be —$(CH_2)_{kk}$— where kk is an integer of from 2 to 6.

The term "carboxyalkyl" as used herein refers to a carboxyl group, —$CO_2H$, appended to a lower alkyl group, as previously defined.

The term "(carboxyamido)alkyl" as used herein refers to a group of the formula —$C(O)NR_{340}R_{341}$, appended to a lower alkyl group, as previously defined. The groups $R_{340}$ and $R_{341}$ are independently selected from hydrogen, lower alkyl, aryl and arylalkyl. Alternatively, $R_{340}$ and $R_{341}$ taken together may optionally be —$(CH_2)_{pp}$— wherein pp is an integer of from 2to 6.

The term "(carboxyhydrazino)alkyl" as used herein refers to a group having the structure —$C(O)NR_{425}NHR_{430}$ appended to a lower alkyl group, as previously defined. The groups $R_{425}$ and $R_{430}$ are independently selected from hydrogen, lower alkyl, aryl and arylalkyl.

The term "guanidinoalkyl" as used herein refers to a group of the structure —$NR_{346}C(=NR_{347})NHR_{348}$ appended to a lower alkyl group, as previously defined. $R_{346}$, $R_{347}$, and $R_{348}$ are independently selected from hydrogen, lower alkyl, heterocyclic, aminoalkyl and aryl. Alternatively, $R_{347}$ and $R_{348}$ taken together may optionally be —$(CH_2)_{vv}$— wherein vv is an integer of from 2 to 6.

The term "ureidoalkyl" as used herein refers to a group having the structure —$NHC(O)NH_2$ appended to a lower alkyl group, as previously defined.

The term "heterocyclic" as used herein refers to any aromatic or non-aromatic 5- or 6-membered ring independently selected from the group consisting of one nitrogen, oxygen, or sulfur; one oxygen and one nitrogen; one sulfur and one nitrogen; one, two, or three nitrogens; wherein the 5-membered ring has 0 to 2 double bonds and the 6-membered ring has 0 to 3 double bonds, wherein the nitrogen and sulfur heteroatoms may optionally be oxidized, wherein the nitrogen heteroatom may optionally be quaternized, and including any bicyclic group in which any of the above heterocyclic rings is fused to a benzene ring. Representative heterocycles include, but are not limited to pyrrolyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazoyl, oxazolidinyl, isoxazolyl, isoxazolidinyl, morpholinyl, indolyl, quinolinyl, thiazolyl, thiazolidinyl, isothiazolyl, isothiazolidinyl, isoquinolinyl, benzimidazolyl, benzothiazolyl, benzoxazolyl, furyl, thienyl, and benzothienyl.

The term "(heterocyclic)alkyl" as used herein refers to a heterocyclic group, as previously defined, appended to an alkyl group as previously defined.

The term "hydroxyalkyl" as used herein refers to —OH appended to a lower alkyl group.

The term "naturally occuring amino acid" refers to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The term "N-terminal protecting group" refers to those groups, as known in the art, intended to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxycarbonyl (Cbz), and benzoyl groups. Other groups are described in: Gross, E.; Meienhofer, J. "The Peptides"Volume 3; Academic Press, 1981.

The term "anaphylatoxin" is used herein to mean C5a, C4a, C3a, or the corresponding des-Arg degradation products.

The term "pharmaceutically acceptable salt" refers to non-toxic acid addition salts such as salts formed with inorganic acids such as hydrochloric acid, hydrobromic acid, phosphoric acid, sulfuric acid and perchloric acid or with organic acids such as acetic acid, oxalic acid, maleic acid, malic acid, tartaric acid, citric acid, succinic acid or malonic acid. Other pharmaceutically acceptable salts include inorganic nitrate, sulfate, acetate, malate, formate, lactate, tartrate, succinate, citrate, p-toluenesulfonate, and the like, including, but not limited to cations based on the alkali and alkaline earth metals, such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Examples of pharmaceutically acceptable, non-toxic esters of the compounds of this invention include $C_1$ to $C_6$ alkyl esters wherein the alkyl group is straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compound of formula I may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6-membered heterocycle containing one nitrogen atom. Amides derived from ammonia, $C_1$ to $C_3$ alkyl primary amides and $C_1$ to $C_2$ dialkyl secondary amides are preferred. Amides of the compound of formula I may be prepared according to conventional methods.

Numerous asymmetric centers may exist in the compounds of the present invention. The present invention contemplates the various stereoisomers and mixtures thereof. In particular, chiral centers can exist at $R_5$, $R_8$, $R_{11}$, $R_{14}$, $R_{17}$, $R_{20}$ and $R_{23}$. Compounds of the present invention containing up to three α-amino acid residues of non-natural configuration have been found to be effective as modulators of anaphylotoxin activity.

Particular stereoisomers are prepared by selecting the starting amino acids or amino acid analogs having the desired stereochemistry and reacting these starting materials by the methods detailed below. Starting compounds of particular stereochemistry are either commercially available or are made by the methods detailed below and resolved by techniques well known in the organic chemical arts.

One class of preferred compounds of the present invention are those in which the group $R_5$ is preferably selected from $>CR_{201}R_{202}$ where $R_{201}$ is selected from aryl and arylalkyl; $R_{202}$ is selected from the group consisting of hydrogen and lower alkyl; $>NR_{203}$ where $R_{203}$ is arylalkyl; $>C=CR_{205}R_{206}$, existing in the Z- or E-configuration where $R_{205}$ is selected from the group consisting of hydrogen and lower alkyl; $R_{206}$ is chosen from the group consisting of aryl or arylalkyl; and substituted cyclopropyl of the formula $$\triangle\substack{R_{201} \\ R_{202}}$$

where $R_{201}$ is selected from aryl and arylalkyl and $R_{202}$ is selected from the group consisting of hydrogen and lower alkyl.

In another class of preferred compounds of the present invention are those wherein $R_8$ is preferably selected from the group consisting of $>CR_{210}R_{211}$ where $R_{210}$ is selected from the group consisting of arylalkyl; aminoalkyl; guanidinoalkyl; and lower alkyl; $R_{211}$ is selected from hydrogen and lower alkyl; $>NR_{213}$ where $R_{213}$ is selected from the group consisting of arylalkyl; aminoalkyl; guanidinoalkyl; and lower alkyl; with the proviso that $R_{213}$ may not have a heteroatom directly attached to the nitrogen or separated from it by one methylene unit; $>C=CR_{215}R_{216}$, existing in either the Z- or E-configuration where $R_{215}$ is selected from hydrogen and lower alkyl; $R_{216}$ is selected from arylalkyl and lower alkyl; and substituted cyclopropyl of the formula $$\triangle\substack{R_{210} \\ R_{211}}$$

where $R_{210}$ is selected from the group consisting of arylalkyl; aminoalkyl; guanidinoalkyl; and lower alkyl; $R_{211}$ is selected from hydrogen and lower alkyl.

The group $R_{17}$ preferably is selected from the group consisting of $>CR_{301}R_{302}$ where $R_{301}$ is selected from the group consisting of lower alkyl; arylalkyl (Arylalkyl is limited to benzyl when $R_{19}$-$R_{20}$-$R_{21}$ represents an L-arginyl residue.); $R_{302}$ is selected from hydrogen and lower alkyl; $>NR_{303}$; $R_{303}$ is selected from the group consisting of hydrogen; lower alkyl; (cycloalkyl) alkyl; and arylalkyl (Arylalkyl is limited to benzyl when $R_{19}$-$R_{20}$-$R_{21}$ represents an L-arginyl residue.); $>C=CR_{305}R_{306}$, existing in either the Z- or E-configuration; $R_{305}$ is selected from hydrogen and lower alkyl; $R_{306}$ is selected from aryl, arylalkyl (Arylalkyl is excluded when $R_{19}$-$R_{20}$-$R_{21}$ represents an L-arginyl residue.); lower alkyl; hydrogen; and (cycloalkyl) alkyl and substituted cyclopropyl of the formula $$\triangle\substack{R_{304} \\ R_{307}}$$

where $R_{304}$ is selected from the group consisting of lower alkyl; aryl; arylalkyl (Arylalkyl is excluded when $R_{19}$-$R_{20}$-$R_{21}$ represents an L-arginyl residue.); and (cycloalkyl) alkyl; $R_{307}$ is selected from hydrogen and lower alkyl.

The group $R_{20}$ is preferably selected from the group consisting of $>CR_{310}R_{311}$ where $R_{310}$ is selected from the group consisting of arylalkyl (Arylalkyl is limited to benzyl when $R_{22}$-$R_{23}$-$R_{24}$ represents an L-arginyl residue.); and guanidinoalkyl; $R_{311}$ is selected from hydrogen and lower alkyl; $>C=CR_{315}R_{316}$, existing in either the Z- or E-configuration where $R_{315}$ is selected from hydrogen and lower alkyl; $R_{316}$ is selected from arylalkyl (Arylalkyl is excluded when $R_{22}$-$R_{23}$-$R_{24}$ represents an L-arginyl residue.) and aryl; and substituted cyclopropyl of the formula $$\triangle\substack{R_{312} \\ R_{317}}$$

where $R_{312}$ is selected from the group consisting of aryl, arylalkyl (Arylalkyl is excluded when $R_{22}$-$R_{23}$-$R_{24}$ represents an L-arginyl residue.) and guanidinoalkyl; $R_{311}$ is selected from hydrogen and lower alkyl.

One class of preferred compounds of the present invention are those in which when G and L are alpha amino acid residues, the chirality of $R_{14}$ and $R_{20}$ is of the D- or unnatural configuration.

One class of preferred compounds of the present invention are those in which $R_4$, $R_7$, $R_{10}$, $R_{13}$, $R_{16}$, $R_{19}$, and $R_{22}$ are $>NH$; or $R_4$, $R_7$, $R_{13}$, $R_{16}$, $R_{19}$, and $R_{22}$ are $>NH$ and E is $R_{35}$.

Another class of preferred compounds are those in which $R_1$-$R_2$-$R_3$ taken together is independently selected from hydrogen, lower alkyl or acetyl.

One class of preferred compounds of the present invention are those in which the groups $R_6$, $R_9$, $R_{12}$, $R_{15}$, $R_{18}$, $R_{21}$, and $R_{24}$ are independently selected from $>C=O$.

Specific examples of compounds, as well as their pharmaceutically acceptable salts, esters, and amides, contemplated as falling within the scope of the present invention include, but are not necessarily limited to, the following:

H-Phenylalanyl-Lysyl-Alanyl-{(2S)-2-Amino-3-cyclohexylpropanoyl}-{(2S)-2-Amino-3-cyclohexylpropanoyl}-DLeucyl-DArginyl-OH;

H-(p-Iodo)Phenylalanyl-Lysyl-{(2S)-2-Amino-3-cyclohexylpropanoyl}-{(2S)-2-Amino-3-cyclohexylpropanoyl}-Leucyl-DAlanyl-Arginyl-OH;

H-Phenylalanyl-Lysyl-Prolyl-DLeucyl-{(2S)-2-Amino-3-cyclohexylpropanoyl}-DArginyl-OH;

H-Phenylalanyl-Lysyl-Alanyl-{(2S)-2-Amino-3-cyclohexylpropanoyl}-Leucyl-DPhenylalanyl-Arginyl-OH;

(N-Methyl)Phenylalanyl-Lysyl-Prolyl-DTyrosyl-{(2S)-2-Amino-3-cyclohexylpropanoyl}-DArginyl-OH;

H-Phenylalanyl-Lysyl-Prolyl-DPhenylalanyl-{(2S)-2-Amino-3-cyclohexylpropanoyl}-DArginyl-OH;

H-Phenylalanyl-Lysyl-Alanyl-{(2S)-2-Amino-3-cyclohexylpropanoyl}-{(2S)-2-Amino-3-cyclohexylpropanoyl}-DLeucyl-Arginyl-OH;

H-Phenylalanyl-Lysyl-Alanyl-{(2S)-2-Amino-3-cyclohexylpropanoyl}-{(2S)-2-Amino-3-cyclohexylpropanoyl}-Leucyl-DArginyl-OH;

(N-Methyl)Phenylalanyl-Lysyl-Prolyl-D(1-Naphthylalanyl)-Phenylalanyl-DArginyl-OH;

(N-Methyl)Phenylalanyl-Lysyl-Prolyl-DPhenylalanyl-{(2S)-2-Amino-3-cyclohexylpropanoyl}-DArginyl-OH;

H-Phenylalanyl-Lysyl-Alanyl-{(2S)-2-Amino-3-cyclohexylpropanoyl}-{(2S)-2-Amino-3-cyclohexylpropanoyl}-Leucyl-DNorleucyl-OH.

In one embodiment of the present invention $R_{13}$-$R_{14}$-$R_{15}$ taken together is {(2R)-2-amino-3-cyclohexylpropanoyl}. Representative examples of this embodiment include the following compounds, as well as their pharmaceutically acceptable salts, esters, and amides:

(N-Methyl)Phenylalanyl-Lysyl-Tyrosyl-{(2R)-2-Amino-3-cyclohexylpropanoyl}-Phenylalanyl-DArginyl-OH;

(N-Methyl)Phenylalanyl-Lysyl-Glutamyl-{(2R)-2-Amino-3-cyclohexylpropanoyl}-Phenylalanyl-DArginyl-OH;

(N-Methyl)Phenylalanyl-Lysyl-Lysyl-{(2R)-2-Amino-3-cyclohexylpropanoyl}-Phenylalanyl-DArginyl-OH;

(N-Methyl)Phenylalanyl-Lysyl-Prolyl-{(2R)-2-Amino-3-cyclohexylpropanoyl}-(1-Naphthylalanyl)-DArginyl-OH;

(N-Methyl)Phenylalanyl-Lysyl-Prolyl-{(2R)-2-Amino-3-cyclohexylpropanoyl}-Phenylalanyl-DArginyl-OH;

H-Phenylalanyl-Lysyl-Prolyl-{(2R)-2-Amino-3-cyclohexylpropanoyl}-Phenylalanyl-DArginyl-OH;

(N-Methyl)Phenylalanyl-Lysyl-{(2R/S )-2-Amino-5-phenylpentanoyl}-{(2R)-2-Amino-3-cyclohexylpropanoyl}-Phenylalanyl-DArginyl-OH;

(N-Methyl)Phenylalanyl-Lysyl-Prolyl-{(2R)-2-Amino-3-cyclohexylpropanoyl}-Tryptophanyl-DArginyl-OH;

(N-Methyl)Phenylalanyl-Lysyl-Arginyl-{(2R)-2-Amino-3-cyclohexylpropanoyl}-Phenylalanyl-DArginyl-OH;

N-Acetyl-{(Z)-2-Amino-3-phenyl-2-propenoyl}-Lysyl-Prolyl{(2R)-2-Amino-3-cyclohexylpropanoyl}-Phenylalanyl-DArginyl-OH;

(N-Methyl)Phenylalanyl-Lysyl-Prolyl-{(2R)-2-Amino-3-cyclohexylpropanoyl}-Phenylalanyl-DPhenylalanyl-OH;

(N-Methyl)Phenylalanyl-Lysyl-Tryptophanyl-{(2R)-2-Amino-3-cyclohexylpropanoyl}-Phenylalanyl-DArginyl-OH;

(N-Methyl) Phenylalanyl-Lysyl-Alanyl-{(2R)-2-Amino-3-cyclohexylpropanoyl}-Phenylalanyl-DArginyl-OH;

H-Phenylalanyl-Lysyl-Azaglycyl-{(2R)-2-Amino-3-cyclohexylpropanoyl}-Phenylalanyl-DArginyl-OH;

(N-Methyl)Phenylalanyl-Lysyl-Prolyl-{(2R)-2-Amino-3-cyclohexylpropanoyl}-Norleucyl-DArginyl-OH;

(N-Methyl)Phenylalanyl-Lysyl-Prolyl-{(2R)-2-Amino-3-cyclohexylpropanoyl}-Phenylalanyl-{(R)-Phenylglycinyl}-OH;

(N-Methyl)Phenylalanyl-Lysyl-{(2S)-2-Amino-4-pentenoyl}-{(2R)-2-Amino-3-cyclohexylpropanoyl}-Phenylalanyl-DArginyl-OH;

(N-Methyl)(2R/S)(3-F)Phenylalanyl-Lysyl-Prolyl-{(2R)-2-Amino-3-cyclohexylpropanoyl}-Phenylalanyl-DArginyl-OH;

H-Phenylalanyl-Lysyl-Prolyl-{(2R)-2-Amino-3-cyclohexylpropanoyl}-Leucyl-DArginyl-OH.

In another embodiment of the present invention $R_{13}$-$R_{14}$-$R_{15}$ taken together is {(2R)-2-amino-3-cyclohexylpropanoyl} and $R_{16}$-$R_{17}$-$R_{18}$ taken together is {(2S)-2-amino-3-cyclohexylpropanoyl}. Representative examples of this embodiment include the following compounds, as well as their pharmaceutically acceptable salts, ester, and amides:

H-Phenylalanyl-Lysyl-Prolyl-{(2R)-2-Amino-3-cyclohexylpropanoyl}-{(2S)-2-Amino-3-cyclohexylpropanoyl}-DArginyl-OH;

H-{(R/S)-t-Butylalanyl}-Lysyl-Prolyl-{(2R)-2-Amino-3-cyclohexylpropanoyl}-{(2S) -2-Amino-3-cyclohexylpropanoyl}-DArginyl-OH;

(N-Methyl)Phenylalanyl-Ornithyl-Prolyl-{(2R)-2-Amino-3-cyclohexylpropanoyl}-{(2S)-2-Amino-3-cyclohexylpropanoyl}-DArginyl-OH;

(N,N-Dimethyl)Phenylalanyl-Lysyl-Prolyl-{(2R)-2-Amino-3-cyclohexylpropanoyl}-{(2S)-2-Amino-3-cyclohexylpropanoyl}-DArginyl-OH;

H-Phenylalanyl-Lysyl-Arginyl-{(2R)-2-Amino-3-cyclohexylpropanoyl}-{(2S)-2-Amino-3-cyclohexylpropanoyl}-DArginyl-OH;

H-Phenylalanyl-Arginyl-Prolyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Arginyl-{(2R)-2-Amino-3-cyclohexylpropanoyl}-{(2S)-2-Amino-3-cyclohexylpropanoyl}-DArginyl-OH;

H-Phenylalanyl-Lysyl-Lysyl-{(2R)-2-Amino-3-cyclohexylpropanoyl}-{(2S)-2-Amino-3-cyclohexylpropanoyl}-DArginyl-OH;

N-Acetyl-{(1R/S)(2R/S)((Z)-1-Amino-2-phenylcyclopropyl)-1-carbonyl}-Lysyl-Alanyl-{(2R)-2-Amino-3-cyclohexylpropanoyl}-{(2S)-2-Amino-3-cyclohexylpropanoyl}-Arginyl-OH;

(N-Methyl)Phenylalanyl-Lysyl-Prolyl-{(2R)-2-Amino-3-cyclohexylpropanoyl}-{(2S)-2-Amino-3-cyclohexylpropanoyl}-DTryptophanyl-OH;

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-N-(Me)(Benzyl);

H-Phenylalanyl-Ornithyl-Prolyl-{(2R)-2-Amino-3-cyclohexylpropanoyl}-{(2S)-2-Amino-3-cyclohexylpropanoyl}-DArginyl-OH;

H-Phenylalanyl-Lysyl-Phenylalanyl-{(2R)-2-Amino-3-cyclohexylpropanoyl}-{(2S)-2-Amino-3-cyclohexylpropanoyl}-DArginyl-OH;

N-Acetyl-Phenylalanyl-Lysyl-Alanyl-{(2R)-2-Amino-3-cyclohexylpropanoyl}-{(2S)-2-Amino-3-cyclohexylpropanoyl}-DArginyl-OH;

H-Phenylalanyl-Lysyl-Leucyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Alanyl-{(2R)-2-Amino-3-cyclohexylpropanoyl}-{(2S)-2-Amino-3-cyclohexylpropanoyl}-DArginyl-OH;

(N-Methyl)Phenylglycyl-Lysyl-Prolyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-OH;

(N-Methyl)Phenylalanyl-Norleucyl-Prolyl-{(2R)-2-Amino-3-cyclohexylpropanoyl}-{(2S)-2-Amino-3-cyclohexylpropanoyl}-DArginyl-OH;

H-Phenylalanyl-Lysyl-Arginyl-{(2R)-2-Amino-3-cyclohexylpropanoyl}-{(2S)-2-Amino-3-cyclohexylpropanoyl}-DAlanyl-OH;

(N-Methyl)Phenylalanyl-Lysyl-Tyrosyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl(N-epsilon-trifluoroacetyl)-Prolyl-{(2R)-2-Amino-3-cyclohexylpropanoyl}-{(2S)-2-Amino-3-cyclohexylpropanoyl}-DArginyl-OH;

H-Phenylalanyl-Lysyl-Alanyl-{(2R)-2-Amino-3-cyclohexylpropanoyl}-{(2S)-2-Amino-3-cyclohexylpropanoyl}-DArginyl-OH;

(N-Benzyl)DProlyl-Lysyl-Prolyl-{(2R)-2-Amino-3-cyclohexylpropanoyl}-{(2S)-2-Amino-3-cyclohexylpropanoyl}-DArginyl-OH.

METHOD OF TREATMENT

The compounds of the present invention serve to modulate the activity of anaphylatoxin. Certain compounds of the present invention function as anaphylatoxin antagonists, while others function as agonists. The antagonist compounds of the present invention block the anaphylatoxin receptor and prevent anaphylatoxin activity, which makes those compounds useful in the treatment and prevention of injurious conditions or diseases in which anaphylatoxin may be involved. Disease states in which anaphylatoxin is involved include asthma, bronchial allergy, chronic inflammation, systemic lupus erythematosus, vasculitis, serum sickness, angioedema, rheumatoid arthritis, osteoarthritis, gout, bullous skin diseases, hypersensitivity pneumonitis, idiopathic pulmonary fibrosis, immune complex-mediated glomerulonephritis, psoriasis, allergic rhinitis, adult respiratory distress syndrome, acute pulmonary disorders, endotoxin shock, hepatic cirrhosis, pancreatitis, inflammatory bowel diseases (including Crohn's disease and ulcerative colitis), thermal injury, Gram-negative sepsis, necrosis in myocardial infarction, leukophoresis, exposure to medical devices (including but not limited to hemodialyzer membranes and extracorpeal blood circulation equipment), chronic hepatitis, transplant rejection, post-viral encephalopathies, and/or ischemia induced myocardial or brain injury. These compounds may also be used as prophylactics for such conditions as shock accompanying Dengue fever. In addition, a combination of antibiotic and anti-inflammatory agent such as corticosteroids (e.g., methylprednisolone) and one or more of the above mentioned compounds may be employed.

Certain compounds of the invention are useful therapeutic agents because of their ability to mimic or promote anaphylatoxin activity and are therefore useful in stimulating the inflammatory response and immune response in mammals who are deficient in this regard. These agonist compounds may be used to assist the body in building its defense mechanism against invasion by infectious microorganisms or other stress. Interaction by these agonists at the anaphylatoxin receptor makes them useful in treating conditions or diseases including, but not limited to cancers (including but not limited to lung carcinoma), immunodeficiency diseases, and severe infections.

In some cases this will involve preventing the underlying cause of the disease state and in other cases, while the underlying disease will not be affected, the compounds of this invention will have the benefit of ameliorating the symptoms or preventing the manifestations of the disease.

The compounds of the present invention may be administered orally, parenterally, by inhalation spray, rectally, or topically in dosage unit formulations containing conventional nontoxic pharmaceutically acceptable carriers, adjuvants and vehicles as desired.

The term "parenteral" as used herein includes subcutaneous, intravenous, intramuscular, intrasternal, intra-arterial injection or infusion techniques, without limitation. The term "topically" encompasses administration rectally and by inhalation spray, as well as by the more common routes of the skin and the mucous membranes of the mouth and nose.

Actual dosage levels of active ingredients in the pharmaceutical compositions of this invention may be varied so as to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 mg to about 100 mg, more typically from about 0.1 mg to about 20 mg, of active compound per kilogram of body weight per day are administered daily to a mammalian host. If desired, the effective daily dose may be divided into multiple doses for purposes of administration, e.g. two to four separate doses per day.

FORMULATION OF PHARMACEUTICAL COMPOSITION

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like, Prolonged absorption of the injectable pharmaceutical form may be brought about by the inclusion of agents which delay abdorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

ANAPHYLATOXIN RECEPTOR BINDING Ki DETERMINATION

Specific inhibition of C5a binding activity of representative compounds of the present invention was measured using 0.03–1 nM $^{125}$I-C5a with 2.5–25 ug/mL of purified PMNL membrane fragments (Borregaard, N.; Heiple, J. M.; Simons, E. R.; and Clark, R. A. *J. Cell. Biol.* 1983, 97, 52–61.). Free and membrane-bound ligand were separated by filtration. Binding potencies for representative examples of compounds of this invention are listed in Table 1.

TABLE 1

| In vitro C5a Receptor Binding Potency of Compounds of this Invention. | |
|---|---|
| Example | $K_i$ μM |
| 6 | 0.080 |
| 58 | 0.011 |
| 107 | 3.6 |
| 125 | 0.026 |
| 152 | 0.083 |
| 187 | 0.30 |
| 212 | 0.11 |
| 224 | 0.012 |
| 360 | 0.053 |
| 370 | 0.085 |
| 40 | 0.10 |
| 97 | 0.52 |
| 120 | 0.11 |
| 128 | 0.039 |
| 166 | 0.035 |
| 195 | 1.5 |
| 214 | 0.09 |
| 305 | 0.22 |
| 367 | 1.9 |
| 390 | 4.0 |

SYNTHESIS OF COMPOUNDS

The novel compounds and salts thereof of the invention can be utilized effectively as therapeutic agents. Accordingly, the present invention further relates to therapeutic compositions comprising a novel compound having the general formula I or salts thereof as an active component.

The compounds of the invention may be prepared by a synthetic method of elongation of a peptide chain through condensation of one amino acid by one, or by a method of coupling fragments consisting of two or several amino acids, or by a combination of these methods in accordance with conventional peptide synthesis methods.

The condensation of two amino acids, the condensation of an amino acid with a peptide or the condensation of one peptide with another peptide may be effected in accordance with conventional condensation methods such as azide method, mixed acid anhydride method, symmetrical anhydride method, DCC (dicyclohexylcarbodiimide) method, active ester method (p-nitrophenyl ester method, N-hydroxysuccinimide ester method, cyanomethyl ester method and the like), Woodward reagent K method, DCC-HOBT(1-hydroxy-benzotriazole) method and the like. These condensation reactions may be done by either solution methods or solid phase synthetic methods. When the peptide chain is elongated by the solid phase method, the C-terminal amino acid is linked to an insoluble carrier. As the insoluble carrier, any that can produce a detachable bond by reacting with a carboxyl group in a C-terminal amino acid may be used, and the examples thereof involve, for example, halomethyl resins such as chloromethyl resin, bromomethyl resin and the like, hydroxy-methyl resin, benzhydrylamine resin, and t-alkyloxycarbonyl hydrazide resin.

As conventional polypeptide synthesis, branched chain amino and carboxyl groups at alpha and omega positions in amino acids may be protected/deprotected if necessary. The protecting groups for amino groups which can be used involve, for example, benzyloxycarbonyl (Z), o-chlorobenzyloxycarbonyl ((2-Cl)Z), p-nitrobenzyloxycarbonyl (Z($NO_2$)), p-methoxybenzyloxycarbonyl (Z(OMe)), t-butoxycarbonyl (Boc), t-amyloxycarbonyl (Aoc), isobornyloxycarbonyl, admantyloxycarbonyl, 2-(4-biphenyl)-2-propyloxycarbonyl (Bpoc), 9-fluorenyl-methoxycarbonyl (Fmoc), methylsulfonylethoxycarbonyl (Msc), trifluoroacetyl, phthalyl, formyl, 2-nitrophenylsulfenyl (Nps), diphenylphosphinothioyl (Ppt), and dimethylphosphinothioyl (Mpt).

The examples of protecting groups for carboxyl groups involve, for example, benzyl ester (OBn), cyclohexyl ester, 4-nitrobenzyl ester (OBn$NO_2$), t-butyl ester (OtBu), 4-picolyl ester (OPic) and the like.

In the course of the synthesis of the present novel compounds, specific amino acids having functional groups other than amino and carboxyl groups in the branched chain such as arginine, cysteine, serine, and the like may be protected, if necessary, with suitable protecting group. It is preferable that for example, the guanidino group ($N^G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mds), 1,3,5-trimethylphenylsulfonyl (Mts) and the like, and the thiol group in cysteine may be protected with benzyl, p-methoxybenzyl, triphenylmethyl, acetamidomethyl, ethylcarbamyl, 4-methylbenzyl (4-MeBn), 2,4,6-trimethylbenzyl (Tmb) and the like, and the hydroxyl group in serine may be protected with benzyl (Bn), t-butyl, acetyl, tetrahydropyranyl and the like.

N-Acetylated peptides were prepared in analogy to Example 120. The following literature procedures were used to prepare N-alkyl- or N,N-dialkyl-amino acid derivatives. Lovett, J. A.; Portoghese, P. J. Med. Chem. 1987, 30, 1144–1149. Borch, R. F.; Hassid, A. I. J. Org. Chem. 1972, 37, 1673–1674. Hansen, D. W.; Pilipauskas, D. J. Org. Chem. 1985, 50, 945–950. Grieco, P. A.; Basha, A. J. Org. Chem. 1987, 52, 5746–5749. Shuman, R. T.; Smithwick, E. L.; Smiley, D. L.; Brooke, G. S.; Gesellchen, P. D. "Peptide: Structure and Function", Proceedings of the Eighth American Peptide Symposium, 1984; p 143–146. Cheung, S. T.; Benoiton, N. L. Can. J. Chem. 1977, 55, 906–910. These reactions were carried out either on the elongated peptide-resin or on amino acid derivatives and then incorporated into the peptide-resin.

The preparation of (2RS)-2-amino-5-phenylpentanoic acid is described in: Greenstein, J. P.; Winitz, M. "Chemistry of the Amino Acids"; John Wiley and Sons, Inc.: New York, 1961; Vol III, p. 2387.

(N-Boc)-(2R)-2-Amino-3-cyclohexylpropanoic acid: A solution of Boc-D-phenylalanine (50 g, 0.19 mol) in methanol (500 mL) was hydrogenated at room temperature at 4 atms with 5% rhodium on alumina (5.0 g). Removal of catalyst by filtration and evaporation yielded the product quantitatively. The (2S)-isomer was prepared in an identical manner from Boc-L-phenylalanine.

The following literature procedures were used to prepare N-guanidino substituted arginine derivatives: Mathias, L. J., Synthesis 1979, 561–576; Maryanoff, C. A.; Stanzione, R. C.; Plampin; J. M.; Mills, J. E. J. Org. Chem. 1986, 51, 1882–1884; Nestor, J. J.; Ho, T. L.; Simpson, R. A.; Horner, B. L.; Jones, G. H.; McRae, G. I.; Vickery, B. H. J. Med. Chem. 1982, 25, 795–801. The obtained arginine derivatives were attached to Merrifield resin as described in: Stewart, J. M.; Young, J. D. "Solid Phase Peptide Synthesis" 2nd edition; Pierce Chemical Co: Rockford, Ill., 1984; p 71–72. The amino acid resin obtained was used to construct the peptide, followed by cleavage and purification to yield the desired peptide analog.

C-terminal esters and acyl hydrazides were prepared as described in: Stewart, J. M.; Young, J. D. "Solid Phase Peptide Synthesis", 2nd edition; Pierce Chemical Co.: Rockford, Ill., 1984.

Disulfides were made according to the method described by: Rich, D. H.; Kawai, M.; Goodman, H. L.; Suttie, J. W. J. Med. Chem. 1983, 26, 910.

The compounds of the invention were prepared by standard solid phase peptide synthesis conditions as described in "Solid Phase Peptide Synthesis" by J. M. Stewart and J. D. Young, Second Edition (1984) and illustrated in Examples 1 and 2 in the experimental section.

The compounds of the invention may also be prepared by partial solid phase synthesis, fragment condensation methods and classical solution methods as exemplified by the methods described in "Peptide Synthesis" Second Edition, M. Bodanszky, Y. S. Klausner, and M. A. Ondetti (1976).

The standard chirality descriptors "R" and "S" are used to indicate an isomerically pure center, If "RS" to indicate a mixture, and "R/S" to indicate a single pure isomer of undetermined configuration. The descriptor "±" refers to a d,l mixture of amino acids at the indicated residue. The descriptor "*" or "**" when written in a chemical name indicates the site of a disulfide or amide linkage, respectively.

The foregoing may be better understood by reference to the following examples which are provided for illustration and not limitation of the practice of the invention. Unless otherwise indicated, the standard peptide methods described above and in examples 1 and 2 were used to assemble the different products, using the precursors indicated by the specific peptide sequence. The product was at least 95% pure, and gave NMR and mass spectra consistent with the proposed structure.

EXAMPLE 1

H-Phenylalanyl-Lysyl (N-epsilon-Cbz)-Prolyl-{(2R)-2-Amino-3-cyclohexyl-propanoyl}-{(2S)-2-Amino-3-cyclohexylpropanoyl}-DArginyl(N-guanidino-Tos) -Merrifield Resin Boc-DArginine(N-guanidino-Tos)-Merrifield resin (0.4–1.0 g) was placed in a solid phase peptide synthesis vessel and amino acids were attached to the resin sequentially in the following order: Boc-(2S)-2-Amino-3-cyclohexylpropanoic acid, Boc-(2R)-2-Amino-3-cyclohexylpropanoic acid, Boc-Proline, (N-alpha-Boc,N-epsilon-Cbz)Lysine, Boc-Phenylalanine, according to the protocol outlined in Agenda A to yield the protected peptide resin: H-Phenylalanyl-Lysyl (N-epsilon-Cbz)-Prolyl-{(2R)-2-Amino-3-cyclohexyl-propanoyl}-{(2S)-2-Amino-3-cyclohexylpropanoyl}-DArginyl(N-guanidino-Tos)-Merrifield resin. Following the synthesis, the protected peptide resin was removed from the reaction vessel by washing the resin three times with 20 mL DMF into a 30–60 mL sintered glass funnel, followed by washing the resin three times with 20 mL methylene chloride. The resin was dried at least five hours, then weighed.

Agenda A

1. Deblock: 45% trifluoroacetic acid (TFA) in methylene chloride containing 2.5% anisole (v/v/v).
2. Neutralization: 10% diisopropylethylamine (DIEA) in methylene chloride (v/v).
3. Single Coupling: 0.2–0.4M Boc-amino acid derivative in N,N-dimethylformamide (DMF), 0.2–0.4 M diisopropylcarbodiimide (DIC) in methylene chloride, reaction time, 60 minutes.
4. Resin base washing: 10% DIEA in methylene chloride (v/v).
5. Single Coupling repeated: same as Step 3.
6. Go to next amino acid residue (go back to Step 1).
7. Upon attachment of the final amino acid to the growing peptide chain, the protecting group (t-Boc) is removed as in Step 1.

EXAMPLE 2

H-Phenylalanyl-Lysyl-Prolyl-{(2R)-2-Amino-3-cyclohexylpropanoyl}-{(2S)-2-Amino-3-cyclohexylpropanoyl}-DArginyl-OH The protected peptide resin of Example 1 (0.6 g) was treated with 1.0 mL anisole and 10 mL hydrogen fluoride (HF) for 60 minutes at 0° C. The HF and anisole were removed in vacuo at 0° C., and the mixture of the peptide and resin was washed with diethyl ether (2×25 mL). The crude peptide was extracted from the mixture by treatment with portions of 20% aqueous acetic acid (4×25 mL), lyophilized to a dry amorphous powder, and purified by high performance liquid chromatography (HPLC) {column: 21.4 mm ID×25 cm or 41.4 mm ID×25 cm, Dynamax (Rainin), 8 um silica, C18 reverse-phase column}. The sample was purified by gradient elution {from 20 to 60% (80% acetonitrile in water with 0.1% trifluoroacetic acid)} at a flow rate of 15–45 mL/min. FAB+ MS: (M+H)+=853.

EXAMPLE 3

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-NHBenzyl N-Boc-D-Arginine hydrochloride (100 mg, 0.3 mmol) was coupled with benzylamine (40 uL, 0.4 mmol) using the mixed anhydride method described in Example 322 to give N-Boc-D-arginine benzylamide. The Boc group was removed by treatment with 4 M hydrochloric acid in dioxane for 1 h. The resulting D-arginine benzylamide was coupled to N-Boc-(N-methyl)phenylalanyl-lysyl(N-epsilon-Boc)-prolyl-{(2R)-2-amino-3-cyclohexylpropanoyl}-{(2S)-2-amino-3-cyclohexylpropanoyl}-OH, which was prepared as described in Example 322, using 1-(3-dimethyl-aminopropyl)-3-ethyl carbodiimide hydrochloride in dimethylformamide using the method described in Example 322. The crude product was deprotected with 50% trifluoroacetic acid in methylene chloride. The material thus obtained was purified by HPLC as described in Example 2 to give the title compound in 26% overall yield.

FAB+MS: (M+H)+=956 Amino Acid Anal.: PheMe (0.83), Lys (1.00), Pro (1.00), Cha (1.86), Arg (1.00)

EXAMPLE 4

H-Phenylalanyl-Lysyl-Alanyl-{(2S )-2-Amino-3-cyclohexylpropanoyl}-{(2S )-2-Amino-3-cyclohexylpropanoyl}-Leucyl-Ornithyl-OH

FAB+ MS: (M+H)+=898

EXAMPLE 5

H-{(R/S)-t-Butylalanyl}-Lysyl-Prolyl-{(2R)-2-Amino-3-cyclohexylpropanoyl}-{(2S )-2-Amino-3-cyclohexylpropanoyl}-DArginyl-OH

FAB+ MS: (M+H)+=833

EXAMPLE 6

H-{(R/S)-t-Butylalanyl}-Lysyl-Prolyl-{(2R)-2-Amino-3-cyclohexylproanoyl}-{(2S)-2-Amino-3-cyclohexylpropanoyl}-DArginyl-OH

FAB+ MS: (M+H)+=833

EXAMPLE 7

H-{3-(2'-Thienyl)alanyl}-Lysyl-Prolyl-D{3-(2'-Thienyl)alanyl}-{3-(2'-Thienyl)alanyl}-DArginyl-OH

FAB+ MS:(M+H)+=859

EXAMPLE 8

H-Phenylalanyl-Lysyl(N-epsilon-trifluoroacetyl)-Prolyl-{(2R)-2-Amino-3-cyclohexylpropanoyl}-DProlyl-DArginyl-OH FAB+ MS: (M+H)+=893 Amino Acid Anal.: Pro (2.15), Phe (1.06), Cha (0.88), Lys (0.94), Arg (0.97)

EXAMPLE 9

H-Phenylalanyl-Lysyl-Cysteinyl*-{(2S)-2-Amino-3-cyclohexylpropanoyl}-((2S)-2-Amino-3-cyclohexylpropanoyl}-Penicillaminyl*-Arginyl-OH
FAB+ MS: (M+H)+ =988

EXAMPLE 10

(N-Methyl)Phenylalanyl-Lysyl-Prolyl-{(2R)-2-Amino-3-cyclohexylpropanoyl}-Phenylalanyl-{(R/S)-2-Benzyl-arginyl}-OH
This compound was prepared in analogy to Example 378.
FAB+ MS: (M+H)+ =951 Amino Acid Anal.: PheMe (0.81), Lys (0.99), Pro (1.02), Cha (0.95), Phe (1.04)

EXAMPLE 11

H-{(2S)-2-Amino-3-cyclohexylpropanoyl}-Lysyl-Prolyl-{(2R)-2-Amino-3-cyclohexylpropanoyl}-Phenylalanyl-DArginyl-OH
FAB+ MS: (M+H)+ =853 Amino Acid Anal.: Pro (0.99), Phe (1.04), Cha (1.93), Lys (0.86), Arg (1.17)

EXAMPLE 12

H-Phenylalanyl-DLysyl-Alanyl-{(2S)-2-Amino-3-cyclohexylpropanoyl}-{(2S)-2-Amino-3-cyclohexylpropanoyl}-DArginyl-OH
FAB+ MS: (M+H)+ =827

EXAMPLE 13

N-Acetyl-Histidyl-Lysyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+ =972

EXAMPLE 14

(N-Methyl)Phenylalanyl-Lysyl-Prolyl-{(2R)-2-Amino-3-cyclohexylpropanoyl}-DPhenylalanyl-{p-Chloro-DPhenylalanyl}-OH
This compound was prepared in analogy to Example No. 322.
FAB+ MS: (M+H)+ =886

EXAMPLE 15

(N-Methyl)Phenylalanyl-Lysyl-Prolyl-{(2R)-2-Amino-3-cyclohexylpropanoyl}-Phenylalanyl-{D-4-Chlorophenylalanyl}-OH
This compound was prepared in analogy to Example No. 322.
FAB+ MS: (M+H)+ =886

EXAMPLE 16

(N-Methyl)Phenylalanyl-Lysyl-Prolyl-{(2R)-2-Amino-3-cyclohexylpropanoyl}-{(2,3R/S )-2-Amino-3-phenylpropanoyl}-DArginyl-OH
FAB+ MS: (M+H)+ =875

EXAMPLE 17

(N-Methyl)Phenylalanyl-Ornithyl-Prolyl-{(2R)-2-Amino-3-cyclohexylpropanoyl}-{(2S)-2-Amino-3-cyclohexylpropanoyl}-DArginyl-OH
FAB+ MS: (M+H)+ =853 Amino Acid Anal.: PheMe (0.89), Orn (1.09), Pro (1.12), Cha (1.89), Arg (1.00)

EXAMPLE 18

H-Phenylalanyl-Lysyl-{(2S)-2-Amino-3-cyclohexylpropanoyl}-Glycyl-Leucyl-DAlanyl-Arginyl-OH
FAB+ MS: (M+H)+ =844 Amino Acid Anal.: Phe (1.06), Lys (1.07), Cha (1.02), Gly (0.99), Leu (1.10), Ala (0.90), Arg (1.05)

EXAMPLE 19

(N-Methyl)Phenylalanyl-Lysyl-Prolyl-{(2R)-2-Amino-3-cyclohexylpropanoyl}-{(2R/S)-m-Fluorophenylalanyl}-DPhenylalanyl-OH
FAB+ MS: (M+H)+ =870

EXAMPLE 20

(N-Methyl)Phenylalanyl-Lysyl-Prolyl-{(2R)-2-Amino-3-cyclohexylpropanoyl}-{(2R/S )-m-Fluorophenylalanyl}-DPhenylalanyl-OH
FAB+ MS: (M+H)+ =870

EXAMPLE 21

(N-Methyl)Phenylalanyl-Lysyl-Prolyl-{(2R)-2-Amino-3-cyclohexylpropanoyl}-Isoleucyl-DArginyl-OH
FAB+ MS: (M+H)+ =827 Amino Acid Anal.: PheMe (1.14), Ile (0.99), Cha (1.00), Lys (0.92), Arg (1.09), Pro (1.12)

EXAMPLE 22

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-NH$_2$
Example 266, N-Boc-(N-Methyl)Phenylalanyl-Lysyl(N-epsilon-Boc)-Prolyl-{(2R)-2-Amino-3-cyclohexylpropanoyl}-{(2S)-2-Amino-3-cyclohexylpropanoyl}-DArginyl-OCH$_3$, (100 mg, 0.1 mmol) was placed in methanol (10 mL) saturated with ammonia in a sealed vessel. After 4 d, the mixture was evaporated to dryness. Removal of the Boc groups with 50% trifluoroacetic acid in methylene chloride furnished the crude material which was purified by HPLC as described in Example 2 to provide the title compound in 64% yield.
FAB+ MS: (M+H)+ =956 Amino Acid Anal.: PheMe (0.83), Lys (0.99), Pro (1.02), Cha (1.85), Arg (0.99)

EXAMPLE 23

H-Lysyl-{(2R/S)-2-Amino-5-phenylpentanoyl}-{(2S)-2-Amino-3-cyclohexylpropanoyl}-Alanyl-Leucyl-DAlanyl-Arginyl-OH
FAB+ MS: (M+H)+ =971

EXAMPLE 24

(N-Methyl)Phenylalanyl-Lysyl-Prolyl-{(2S)-2-Amino-3-cyclohexylpropanoyl}-Phenylalanyl-DNorleucyl-OH
FAB+ MS: (M+H)+ =818

EXAMPLE 25

H-(m-Fluoro)Phenylalanyl-Lysyl-Prolyl-{(2R)-2-Amino-3-cyclohexylpropanoyl}-Phenylalanyl-DArginyl-OH
FAB+ MS: (M+H)+ =865

EXAMPLE 26

(N,N-Dimethyl)Phenylalanyl-Lysyl-Prolyl-{(2R)-2-Amino-3-cyclohexylpropanoyl}-{(2S)-2-Amino-3-cyclohexylpropanoyl}-DArginyl-OH

FAB+ MS: (M+H)+ =881

EXAMPLE 27

H-Lysyl-Cysteinyl*-{(2S)-2-Amino-3-cyclohexylpropanoyl}-{(2S)-2-Amino-3-cyclohexylpropanoyl}-Dpenicillaminyl*-DAlanyl-Arginyl-OH

FAB+ MS: (M+H)+ =912

EXAMPLE 28

H-Phenylalanyl-Lysyl-Arginyl-{(2R)-2-Amino-3-cyclohexylpropanoyl}-{(2S)-2-Amino-3-cyclohexylpropanoyl}-DArginyl-OH FAB+ MS: (M+H)+ =913 Amino Acid Anal.: Phe (0.95), Lys (1.05), Cha (1.92), Arg (2.01)

EXAMPLE 29

H-Glycyl-Lysyl-Prolyl-{(2R)-2-Amino-3-cyclohexylpropanoyl}Phenylalanyl-DArginyl-OH FAB+ MS: (M+H)+ =757 Amino Acid Anal.: Gly (0.87), Phe (1.04), Cha (0.96), Lys (1.09), Arg (1.01), Pro (1.03)

EXAMPLE 30

(N- Isopropyl)Phenylalanyl-Lysyl-Alanyl-{(2R)-2-Amino-3-cyclohexylpropanoyl}-{(2S)-2-Amino-3-cyclohexylpropanoyl}-DArginyl-OH

FAB+ MS: (M+H)+ =869

EXAMPLE 31

N-Acetyl-Histidyl-Lysyl-Aspartyl-{(2R)-2-Amino-3-cyclohexylpropanoyl}-{(2R)-2-Amino-3-cyclohexylpropanoyl}-Leucyl-Arginyl-OH

FAB+ MS: (M+H)+ =1016

EXAMPLE 32

(N-Methyl)Phenylalanyl-Lysyl-Prolyl-{(2R)-2-Amino-3-cyclohexylpropanoyl}-Phenylalanyl-{(RS)-3-Fluorophenylalanyl}-OH This compound was prepared in analogy to Example No. 322.

FAB+ MS: (M+H)+ =870

EXAMPLE 33

(N-Methyl)Phenylalanyl-Lysyl-Prolyl-{(2R)-2-Amino-3-cyclohexylpropanoyl}-{(2,3R/S)-2-Amino-3-phenylpropanoyl}-DArginyl-OH

FAB+ MS: (M+H)+ =875

EXAMPLE 34

H-Arginyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =862 Amino Acid Anal.: Pro (0.97), Cha (2.03), Lys (0.97), Arg (2.02)

EXAMPLE 35

H-Lysyl-Phenylalanyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =940 Amino Acid Anal.: Lys (1.00), Phe (0.99), Cha (1.92), Leu (1.04), Ala (0.99), Arg (0.99)

EXAMPLE 36

(N-Methyl)Phenylalanyl-Lysyl-Prolyl-{(2R)-2-Amino-3-cyclohexylpropanoyl}-Alanyl-DPhenylalanyl-OH FAB+ MS: (M+H)+ =776 Amino Acid Anal.: Ala (0.99), PheMe (1.02), Phe (0.98), Cha (0.98), Lys (1.02), Pro (1.08)

EXAMPLE 37

H-Phenylalanyl-Lysyl-Prolyl-{(2R)-2-Amino-3-cyclohexylpropanoyl}-DPhenylalanyl-DArginyl-OH FAB+ MS: (M+H)+ =847 Amino Acid Anal.: Pro (1.05), Phe (1.92), Cha (1.03), Lys (0.96), Arg (1.04)

EXAMPLE 38

H-Lysyl-{(2R/S)-2-Amino-5-phenylpentanoyl}-{(2S)-2-Amino-3-cyclohexylpropanoyl}-Alanyl-Leucyl-DAlanyl-Arginyl-OH

FAB+ MS: (M+H)+ =971

EXAMPLE 39

(N-Methyl) Phenylalanyl-Lysyl-Tyrosyl-{(2R)-2-Amino-3-cyclohexylpropanoyl}-Phenylalanyl-DArginyl-OH FAB+ MS: (M+H)+ =927 Amino Acid Anal.: PheMe (0.97), Lys (0.93), Tyr (0.99), Cha (0.96), Phe (1.00), Arg (1.02)

EXAMPLE 40

(N-Methyl)Phenylalanyl-Lysyl-Glutamyl-{(2R)-2-Amino-3-cyclohexylpropanoyl}-Phenylalanyl-DArginyl-OH

FAB+ MS: (M+H)+ =893

EXAMPLE 41

H-DPhenylalanyl-Lysyl-Prolyl-{(2R)-2-Amino-3-cyclohexylpropanoyl}-{(2S)-2-Amino-3-cyclohexylpropanoyl}-DArginyl

This compound was prepared in analogy to Example 257.

FAB+ MS: (M+H)+ =835 Amino Acid Anal.: Phe (0.95), Lys (1.00), Pro (1.14), Cha (2.04), Arg (1.02)

EXAMPLE 42

H-Lysyl-Cysteinyl* -{(2S)-2-Amino-3-cyclohexylpropanoyl}-{(2S) -2-Amino-3-cyclohexylpropanoyl}-Penicillaminyl*-DAlanyl-Arginyl-OH

FAB+ MS: (M+H)+ =912

EXAMPLE 43

H-Phenylalanyl-Lysyl-Prolyl-DLysyl-{(2S)-2-Amino-3-cyclohexylpropanoyl}-DArginyl-OH FAB+ MS: (M+H)+ =828 Amino Acid Anal.: Phe (0.96), Lys (2.02), Cha (1.84), Arg (1.03)

EXAMPLE 44

(N-Methyl) Phenylalanyl-Lysyl-Prolyl-DLeucyl-Leucyl-Arginyl-OH

FAB+ MS: (M+H)+ =787 Amino Acid Anal.: PheMe (0.97), Leu (2.01), Lys (0.98), Arg (0.87), Pro (1.10)

EXAMPLE 45

H-Phenylalanyl-Lysyl-{2-Aminocyclohexanecarbonyl}-{(2R)-2-Amino-3-cyclohexylpropanoyl}-{(2S)-2-Amino-3-cyclohexylpropanoyl}-DArginyl-OH FAB+ MS: (M+H)+=881 Amino Acid Anal.: Phe (1.03), Lys (0.99), Cha (1.90), Arg (1.00)

EXAMPLE 46

N-Acetyl-Lysyl-Aspartyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+=950

EXAMPLE 47

(N-Methyl)Phenylalanyl-Lysyl-Prolyl-{(2R)-2-Amino-3-cyclohexylpropanoyl}-Tyrosyl(O-Ethyl)-DPhenylalanyl-OH
FAB+ MS: (M+H)+=896

EXAMPLE 48

(N-Methyl)Phenylalanyl-Lysyl-Prolyl-DLeucyl-Phenylalanyl-DArginyl-OH
FAB+ MS: (M+H)+=821 Amino Acid Anal.: PheMe (0.86), Leu (1.03), Phe (0.98), Lys (0.83), Arg (0.98), Pro (1.07)

EXAMPLE 49

H-DArginyl-Lysyl-Prolyl-{(2R)-2-Amino-3-cyclohexylpropanoyl}-{(2S)-2-Amino-3-cyclohexylpropanoyl}-DArginyl-OH
FAB+ MS: (M+H)+=862 Amino Acid Anal.: Pro (0.93), Lys (1.03), Arg (2.03)

EXAMPLE 50

H-Phenylalanyl-Arginyl-Prolyl-{(2R)-2-Amino-3-cyclohexylpropanoyl}-{(2S)-2-Amino-3-cyclohexylpropanoyl}-DArginyl-OH
FAB+ MS: (M+H)+=881 Amino Acid Anal.: Phe (0.96), Arg (2.05), Pro (1.02), Cha (1.96)

EXAMPLE 51

H-DLysyl-Phenylalanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+=940 Amino Acid Anal.: Lys (1.00), Phe (1.00), Cha (1.90), Leu (1.04), Ala (0.98), Arg (0.99)

EXAMPLE 52

(N-Methyl)Phenylalanyl-Lysyl-Prolyl-DIsoleucyl-Phenylalanyl-DArginyl-OH
FAB+ MS: (M+H)+=821 Amino Acid Anal.: PheMe (1.29), Ile (0.97), Phe (0.98), Lys (0.99), Arg (1.06), Pro (1.06)

EXAMPLE 53

(N-Methyl)Phenylalanyl-Lysyl(N-epsilon-trifluoroacetyl)-Prolyl-{(2R)-2-Amino-3-cyclohexylpropanoyl}-Phenylalanyl-DArginyl-OH
FAB+ MS: (M+H)+=957

EXAMPLE 54

H-Phenylalanyl-Lysyl-Alanyl-{(2S)-2-Amino-3-cyclohexylpropanoyl}-{(2S)-2-Amino-3-cyclohexylpropanoyl}-DArginyl-DArginyl-OH
FAB+ MS: (M+H)+=983

EXAMPLE 55

(N-Methyl)Phenylalanyl-Lysyl-Prolyl-{(2R)-2-Amino-3-cyclohexylpropanoyl}-(2-Naphthylalanyl)-DArginyl-OH
FAB+ MS: (M+H)+=911 Amino Acid Anal.: PheMe (0.95), Cha (0.92), Lys (1.08), Arg (0.90), Pro (1.14)

EXAMPLE 56

(N-Methyl)Phenylalanyl-Lysyl-Arginyl-{(2R)-2-Amino-3-cyclohexylpropanoyl}-{(2S)-2-Amino-3-cyclohexylpropanoyl}-DArginyl-OH
FAB+ MS: (M+H)+=926 Amino Acid Anal.: Phe (0.91), Lys (0.98), Cha (1.93), Arg (2.02)

EXAMPLE 57 (SEQUENCE ID NO. 1)

H-Phenylalanyl-Lysyl-Alanyl-{(2S)-2-Amino-3-cyclohexylpropanoyl}-{(2S)-2-Amino-3-cyclohexylpropanoyl}-Arginyl-OH
FAB+ MS: (M+H)+=827

EXAMPLE 58

H-Phenylalanyl-Lysyl-Lysyl-{(2R)-2-Amino-3-cyclohexylpropanoyl}-{(2S)-2-Amino-3-cyclohexylpropanoyl}-DArginyl-OH
FAB+ MS: (M+H)+=884 Amino Acid Anal.: Phe (0.96), Lys (2.02), Cha (1.84), Arg (1.03)

EXAMPLE 59

(N-Methyl)Phenylalanyl-{Lysyl(N,N-epsilon-dimethyl)}-Prolyl-{(2R)-2-Amino-3-cyclohexylpropanoyl}-Phenylalanyl-DArginyl-OH Boc-DArg(N-guanidino-Tos)-Merrifield resin (0.5 g, 0.44 mmol/g substitution) was used to construct the peptide. Amino acids were attached to the resin sequentially in the following order: Boc-phenylalanine, Boc-(2R)-2-amino-3-cyclohexylpropanoic acid, Boc-proline, (N-alpha-Boc-N-epsilon-Fmoc)-lysine, and Boc-N-methylphenylalanine. After the last amino acid was attached, the sequence was stopped at agenda A-5. Boc-protected resin was washed with methylene chloride (3×10 mL) and DMF (3×10 mL). After 20% piperidine in DMF (10 mL) was added and mixed for 30 min, the resin was washed with DMF (3×10 mL) and 30% formaldehyde aq. solution (0.2 mL, 2.5 mmol) in 0.1% acetic acid in DMF (10 mL) was added, followed by sodium cyanoborohydride (320 mg, 5 mmol). The reaction was allowed to proceed at room temperature for 1 h. After the peptide resin obtained was washed with DMF (3×10 mL) and methylene chloride (3×10 mL), the title compound was isolated by the method described in Example 2.
FAB+ MS: (M+H)+=889

EXAMPLE 60

H-Phenylalanyl-Lysyl-{2-Amino-2-methylpropanoyl}-{(2R)-2-Amino-3-cyclohexylpropanoyl}-{(2S)-2-Amino-3-cyclohexylpropanoyl}-DArginyl-OH
FAB+ MS: (M+H)+=841

EXAMPLE 61

H-Lysyl-Alanyl-{(2S)-2-Amino-3-cyclohexylpropanoyl}-{(2S)-2-Amino-3-cyclohexylpropanoyl}-Leucyl-DAlanyl-Arginyl-OH
FAB+ MS: (M+H)+=864

EXAMPLE 62

(N-Methyl)Phenylalanyl-Lysyl-Prolyl-{(2R)-2-Amino-3-cyclohexylpropanoyl}-{p-Nitrophenylalanyl}-DPhenylalanyl-OH
FAB+ MS: (M+H)+=897

EXAMPLE 63

(N-Methyl)Phenylalanyl-Lysyl-(1-Naphthylalanyl)-{(2R)-2-Amino-3-cyclohexylpropanoyl}-Phenylalanyl-DArginyl-OH FAB+ MS: (M+H)+ =961 Amino Acid Anal.: PheMe (0.94), Phe (0.97), Cha (0.94), Lys (1.00), Arg (1.03)

EXAMPLE 64

H-Phenylalanyl-Lysyl-Alanyl-{(2S)-2-Amino-3-cyclohexylpropanoyl}-{(2R)-2-Amino-3-cyclohexylpropanoyl}-Leucyl-Arginyl-OH

FAB+ MS: (M+H)+ =940

EXAMPLE 65

(N-Methyl)Phenylalanyl-{(2S)-2-Amino-6-benzamidinylhexanoyl}-Prolyl-{(2R)-2-Amino-3-cyclohexylpropanoyl}-Phenylalanyl-DArginyl-OH (N-Methyl)Phenylalanyl-Lysyl-Prolyl-{(2R)-2-Amino-3-cyclohexylpropanoyl}-Phenylalanyl-DArginyl-OH.3HOAc was prepared as described in Examples 1 and 2. The peptide was used without HPLC purification in the following reaction. This peptide (100 mg, 0.1 mmol) was dissolved in NaOH solution (1 N, 0.5 mL). The reaction mixture was diluted with acetone/water 2:1 (1.5 mL) and methylbenzimidate hydrochloride (60 mg, 0.35 mmol) was added. The reaction mixture was stirred at 50° C. overnight. The acetone was then removed in vacuo, the resulting aqueous solution acidified to pH 3 with trifluoroacetic acid, and acetonitrile added to dissolve any material that may oil out of the solution. The mixture is purified by HPLC by the method described in Example 2 to give the title compound (31 mg, 26% yield).

FAB+ MS: (M+H)+ =964 Amino Acid Anal.: PheMe (0.99), Phe (0.94), Pro (1.03), Cha (1.05), Arg (1.03)

EXAMPLE 66

H-Phenylalanyl-Lysyl-Prolyl-{(2S)-2-Amino-3-cyclohexylpropanoyl}-Phenylalanyl-DArginyl-OH FAB+ MS: (M+H)+ =847 Amino Acid Anal.: Pro (0.96), Phe (2.16), Cha (0.91), Lys (0.97), Arg (1.00)

EXAMPLE 67

H-Lysyl-Phenylalanyl-Alanyl-{(2S)-2-Amino-3-cyclohexylpropanoyl}-{(2S)-2-Amino-3-cyclohexylpropanoyl}-DArginyl-OH

FAB+ MS: (M+H)+ =827

EXAMPLE 68

(N-Methyl)Phenylalanyl-Lysyl-Prolyl-{(2R)-2-Amino-3-cyclohexylpropanoyl}-Phenylalanyl-{(2RS)-2-Amino-3-methyl-3-phenylbutanoyl}-OEt Conjugate addition of phenylmagnesium bromide to diethyl isopropylidinemalonate gave diethyl (alpha, alpha-dimethylbenzyl)malonate in quantitative yield: Holmberg, C. *Liebigs Ann. Chim.* 1981, 748–760. Monohydrolysis (Plattner, J. J.; Marcotte, P. A.; Kleinert, H. D.; Stein, H. H.; Greer, J.; Bolis, G.; Fung,. A. K.; Bopp, B. A.; Luly, J. R.; Sham, H. L.; Kempf, D. J.; Rosenberg, S. H.; Dellaria, J. F.; De, B.; Merits, I.; Perun, T. J. *J. Med. Chem.* 1988, 31, 2277–2288.) followed by Curtius rearrangement (Shioiri, T.; Ninomiya, K.; Yamada, S. *J. Am. Chem. Soc.* 1972, 94, 6203.) produced N-Boc-(R/S)-beta, beta-dimethylphenylalanine ethyl ester in 15% yield: 1H NMR (CDCl3, 300 MHz) δ1.0 (t, 3 H), 1.39 (s, 3 H), 1.4 (s, 9 H), 1.43 (s, 3 H), 3.94 (q, 2 H), 4.52 (d, 1 H), 5.06 (d, 1 H), 7.22 (m, 1 H), 7.32 (m, 4 H); mass spectrum, m/e 322 (M+H). After removal of the Boc group with 4 M hydrochloric acid in dioxane, the amino ester was coupled to N-Boc(N-Methyl)Phenylalanyl-Lysyl(N-epsilon-Boc)-Prolyl-{(2R)-2-Amino-3-cyclohexylpropanoyl}-Phenylalanyl-OH (Prepared as described in Example 322) with 1-(3-dimethylaminopropyl)-3-ethyl carbodiimide hydrochloride. The Boc groups were cleaved with methylene chloride-trifluoroacetic acid (1:1). HPLC, carried out as described in Example 2 provided the inseparable diastereomeric pair in a 35% combined yield.

FAB+ MS: (M+H)+ =908 Amino Acid Anal.: PheMe (1.02), Lys (1.01), Pro (0.99), Cha (0.99), Phe (1.00)

EXAMPLE 69

(N-Methyl)Phenylalanyl-Lysyl-Prolyl-{(2R)-2-Amino-3-cyclohexylpropanoyl}-{(2S)-2-Amino-3-cyclohexylpropanoyl}-{(2R/S)-2-Amino-3-methyl-3-phenylbutanoyl}-OEt This compound was prepared in analogy to Example 68. The diastereomeric pair, Examples 69 and 83, were separable by HPLC.

FAB+ MS: (M+H)+ =914 Amino Acid Anal.: PheMe (0.95), Lys (0.99), Pro (1.01), Cha (1.92)

EXAMPLE 70

(N-Methyl)Phenylalanyl-Citrullyl-Prolyl-DPhenylalanyl-{(2S)-2-Amino-3-cyclohexylpropanoyl}-DArginyl-OH FAB+ MS: (M+H)+ =890 Amino Acid Anal.: PheMe (0.90), Phe (1.04), Cha (0.91), Cit (1.06), Arg (1.06), Pro (1.03)

EXAMPLE 71

H-Phenylalanyl-Lysyl(N-epsilon-trifluoroacetyl)-Prolyl-{(2R)-2-Amino-3-cyclohexylpropanoyl}-Arginyl-DArginyl-OH FAB+ MS: (M+H)+ =952 Amino Acid Anal.: Phe (1.06), Lys (1.08), Cha (0.97), Pro (0.92), Arg (2.00)

EXAMPLE 72

H-Phenylalanyl-Lysyl-Alanyl-{(2S)-2-Amino-3-cyclohexylpropanoyl}-Glycyl-DArginyl-OH

FAB+ MS: (M+H)+ =731

EXAMPLE 73

H-Lysyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =834 Amino Acid Anal.: Lys (1.98), Pro (1.10), Cha (1.85), Arg (1.02)

EXAMPLE 74

(N-Methyl)Phenylalanyl-Glycyl-Prolyl-{(2R)-2-Amino-3-cyclohexylpropanoyl}-Phenylalanyl-DArginyl-OH

FAB+ MS: (M+H)+ =790

EXAMPLE 75

H-Phenylalanyl-Lysyl-DProlyl-{(2S)-2-Amino-3-cyclohexylpropanoyl}-Leucyl-DAlanyl-Arginyl-OH

FAB+ MS: (M+H)+ =884

EXAMPLE 76

(N-Methyl) Phenylalanyl-Lysyl-Prolyl-{(2R)-2-Amino-3-cyclohexylpropanoyl}-{p-Aminophenylalanyl}-DPhenylalanyl-OH
FAB+ MS: (M+H)+ =866

EXAMPLE 77

H-Phenylalanyl-DLysyl-{2-Amino-2-methylpropanoyl}-{(2R)-2-Amino-3-cyclohexylpropanoyl}-Phenylalanyl-DArginyl-OH
FAB+ MS: (M+H)+ =835

EXAMPLE 78

H-Phenylalanyl-Lysyl-Prolyl-DValyl-{(2S)-2-Amino-3-cyclohexylpropanoyl}-DArginyl-OH
FAB+ MS: (M+H)+ =799 Amino Acid Anal.: Phe (0.98), Lys (0.98), Pro (1.06), Val (0.93), Cha (1.01), Arg (1.04)

EXAMPLE 79

H-Phenylalanyl-Lysyl-Alanyl-{(2R)-2-Amino-3-cyclohexylpropanoyl}-{(2S)-2-Amino-3-cyclohexylpropanoyl}-Leucyl-Arginyl-OH
FAB+ MS: (M+H)+ =940

EXAMPLE 80

(N-Methyl)Phenylalanyl-Lysyl-Prolyl-{(2R)-2-Amino-3-cyclohexylpropanoyl}-Phenylalanyl-DTryptophanyl-OH
FAB+ MS: (M+H)+ =891

EXAMPLE 81

H-Phenylalanyl-Lysyl-Prolyl-{(2R)-2-Amino-3-cyclohexylpropanoyl}-Phenylalanyl-Arginyl-OH
FAB+ MS: (M+H)+ =847 Amino Acid Anal.: Pro (1.10), Phe (1.88), Cha (1.06), Lys (0.87), Arg (1.09)

EXAMPLE 82

H-DHistidyl-Lysyl-Alanyl-{(2S)-2-Amino-3-cyclohexylpropanoyl }-{(2S)-2-Amino-3-cyclohexylpropanoyl}-Leucyl-DArginyl-OH
FAB+ MS: (M+H)+ =930

EXAMPLE 83

(N-Methyl)Phenylalanyl-Lysyl-Prolyl-{(2R)-2-Amino-3-cyclohexylpropanoyl}-{(2S)-2-Amino-3-cyclohexylpropanoyl}-{(2R/S)-2-Amino-3-methyl-3-phenylbutanoyl}-OEt
The title compound was prepared as described in Example 69.
FAB+ MS: (M+H)+ =914 Amino Acid Anal.: PheMe (0.66), Lys (1.01), Pro (0.99), Cha (1.94)

EXAMPLE 84

(N-Methyl)Phenylalanyl-{(2S)2-Amino-6-ureidohexanoyl}-Prolyl-DPhenylalanyl-{(2S)-2-Amino-3-cyclohexylpropanoyl}-DArginyl-OH
FAB+ MS: (M+H)+ =904 Amino Acid Anal.: PheMe (0.91), Phe (1.07), Cha (0.93), hCit (0.98), Arg (1.06), Pro (1.04)

EXAMPLE 85

H-Phenylalanyl-Lysyl(N-epsilon-trifluoroacetyl)-Prolyl-DArginyl-{(2S)-2-Amino-3-cyclohexylpropanoyl}-DArginyl-OH FAB+ MS: (M+H)+ =952 Amino Acid Anal.: Pro (1.05), Phe (0.96), Lys (0.95), Arg (2.03)

EXAMPLE 86

H-Phenylalanyl-Lysyl-Alanyl-{(2S)-2-Amino-3-cyclohexylpropanoyl}-Alanyl-Leucyl-DArginyl-OH
FAB+ MS: (M+H)+ =858

EXAMPLE 87

(N-Methyl)Phenylalanyl-Lysyl-Prolyl-DAspartyl-Phenylalanyl-DArginyl-OH
FAB+ MS: (M+H)+ =823 Amino Acid Anal.: PheMe (0.99), Lys (0.92), Pro (0.95), Asx (1.04), Phe (1.05), Arg (1.06)

EXAMPLE 88

(N-Methyl)Phenylalanyl-Glutamyl-Prolyl-{(2R)-2-Amino-3-cyclohexylpropanoyl}-Phenylalanyl-DArginyl-OH
FAB+ MS: (M+H)+ =862

EXAMPLE 89

(N,N-Diallyl)Phenylalanyl-Lysyl-Alanyl-{(2R)-2-Amino-3-cyclohexylpropanoyl}-{(2S)-2-Amino-3-cyclohexylpropanoyl}-DArginyl-OH
FAB+ MS: (M+H)+ =907

EXAMPLE 90

H-Phenylalanyl-Lysyl-Alanyl-{(2S)-2-Amino-3-cyclohexylpropanoyl}-Leucyl-DProlyl-Arginyl-OH
FAB+ MS: (M+H)+ =884 Amino Acid Anal.: Phe (0.99), Lys (1.07), Ala (0.92), Cha (1.24), Leu (1.04), Pro (0.97), Arg (1.16)

EXAMPLE 91

(N-Methyl)Phenylalanyl-Lysyl-Prolyl-{(2R)-2-Amino-3-cyclohexylpropanoyl}-{2-Aminoindan-2-carbonyl}-Dphenylalanyl-OH
The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892.
FAB+ MS: (M+H)+ =864

EXAMPLE 92

N-Acetyl-{(1R/S)(2R/S)((Z)-1-Amino-2-phenylcyclopropyl)-1-carbonyl}-Lysyl-Alanyl-{(2R)-2-Amino-3-cyclohexylpropanoyl}-{(2S)-2-Amino-3-cyclohexylpropanoyl}-Arginyl-OH
The C-terminal pentapeptide is prepared under standard solid phase peptide synthesis conditions. The epsilon nitrogen of lysine is protected as its Fmoc derivative which remains intact during the acidic cleavage of the pentapeptide from the resin. Racemic ((Z)-1-Acetamido-2-phenylcyclopropane)-1-carboxylic acid is prepared from Z-acetamidocinnamic acid according to the methodology given in, Schmidt, U.; Lieberknecht, A.; Wild, *J. Synthesis* 1988, 159–172, and the references cited therein. This amino acid is then coupled in solution phase to the pentapeptide by the mixed acid anhydride method, and the Fmoc group is removed with piperidine. Separation of the diastereomeric products by HPLC furnishes the final product.

EXAMPLE 93

H-Phenylalanyl-Lysyl-{2-Amino-2-methylpropanoyl}-{(2R)-2-Amino-3-cyclohexylpropanoyl}-Phenylalanyl-DArginyl-OH
FAB+ MS: (M+H)+ =835

EXAMPLE 94

H-Phenylalanyl-Lysyl-Prolyl-{(2R)-2-Amino-3-cyclohexylpropanoyl}-{(2S)-2-Amino-3-cyclohexylpropanoyl}-DOrnithyl-OH FAB+ MS: (M+H)+=811 Amino Acid Anal.: Pro (1.01), Phe (0.98), Cha (1.99), Lys (1.02)

EXAMPLE 95 (SEQUENCE ID NO. 2)

H-Phenylalanyl-Lysyl-Alanyl-{(2S)-2-Amino-3-cyclohexylpropanoyl}-Leucyl-Arginyl-OH

FAB+ MS: (M+H)+=787

EXAMPLE 96

(N-Methyl)Phenylalanyl-Lysyl-Prolyl-{(2R)-2-Amino-3-cyclohexylpropanoyl}-{(2S)-2-Amino-3-cyclohexylpropanoyl}-DTryptophanyl-OH

FAB+ MS: (M+H)+=897

EXAMPLE 97

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-N-(Methyl)(Benzyl)

This compound was prepared in analogy to Example 3.

FAB+ MS: (M+H)+=970 Amino Acid Anal.: PheMe (0.83), Lys (1.00), Pro (1.02), Cha (1.90), Arg (0.98)

EXAMPLE 98

H-Phenylalanyl-Lysyl-Alanyl-{(2R)-2-Amino-3-cyclohexylpropanoyl}-{(2S)-2-Amino-3-cyclohexylpropanoyl)-DLeucyl-DArginyl-OH

FAB+ MS: (M+H)+=940

EXAMPLE 99

H-Arginyl-{(2R)-2-Amino-3-cyclohexylpropanoyl}-{(2S)-2-Amino-3-cyclohexylpropanoyl}-Alanyl-DLysyl-DPhenylalanyl-OH

FAB+ MS: (M+H)+=827

EXAMPLE 100

(N-Methyl)Phenylalanyl-Lysyl-Prolyl-DPhenylglycyl-Alanyl-DArginyl-OH

FAB+ MS: (M+H)+=765 Amino Acid Anal.: Ala (0.58), Phg (0.91), PheMe (0.94), Lys (0.97), Arg (1.03), Pro (1.04)

EXAMPLE 101

H-Phenylalanyl-Lysyl(N-epsilon-trifluoroacetyl)-Prolyl-{(2R)-2-Amino-3-cyclohexylpropanoyl}-Glutamyl-DArginyl-OH FAB+ MS: (M+H)+=925 Amino Acid Anal.: Glu (0.90), Pro (1.00), Phe (0.98), Cha (1.02), Lys (1.00), Arg (1.09)

EXAMPLE 102

H-Phenylalanyl-Lysyl-Alanyl-{(2S)-2-Amino-3-cyclohexylpropanoyl}-{(2S)-2-Amino-3-cyclohexylpropanoyl}DLeucyl-DArginyl-OH

FAB+ MS: (M+H)+=940

EXAMPLE 103

(N-Methyl)Phenylalanyl-Lysyl-Prolyl-DtLeucyl-Phenylalanyl-DArginyl-OH

FAB+ MS: (M+H)+=821 Amino Acid Anal.: PheMe (1.34), Lys (0.97), Pro (0.93), Phe (1.01), Arg (1.03)

EXAMPLE 104

H-Leucyl-Lysyl-Prolyl-{(2R)-2-Amino-3-cyclohexylpropanoyl}-Phenylalanyl-DArginyl-OH FAB+ MS: (M+H)+=813 Amino Acid Anal.: Pro (0 95), Leu (1.10), Phe (1.05), Cha (0.90), Lys (0.95), Arg (1.04)

EXAMPLE 105

H-{(3R/S)-1,2,3,4-Tetrahydroisoquinolin-3-carbonyl}-Lysyl-Alanyl-{(2R)-2-Amino-3-cyclohexylpropanoyl}-{(2S) -2-Amino-3-cyclohexylpropanoyl}-DArginyl-OH

FAB+ MS: (M+H)+=839

EXAMPLE 106

H-{(3R/S)-1,2,3,4-Tetrahydroisoquinolin-3-carbonyl}-Lysyl-Alanyl-{(2R)-2-Amino-3-cyclohexylpropanoyl}-{(2S)-2-Amino-3-cyclohexylpropanoyl}-DArginyl-OH

FAB+ MS: (M+H)+=839

EXAMPLE 107

H-(p-Iodo)Phenylalanyl-Lysyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+=1066 Amino Acid Anal.: Lys (0.72), Cha (1.99), Leu (1.00), Ala (1.29), Arg (1.05)

EXAMPLE 108

(N-Methyl)Phenylalanyl-Lysyl-Prolyl-{(2R)-2-Amino-3-cyclohexylpropanoyl}-{2-Aminoindan-2-carbonyl}-DArginyl-OH The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892.

FAB+ MS: (M+H)+=873

EXAMPLE 109

H-Phenylalanyl-Lysyl-Prolyl-DGlutamyl-{(2S)-2-Amino-3-cyclohexylpropanoyl}-DArginyl-OH

FAB+ MS: (M+H)+=929

EXAMPLE 110

H-Phenylalanyl-Ornithyl-Prolyl-{(2R)-2-Amino-3-cyclohexylpropanoyl}-{(2S)-2-Amino-3-cyclohexylpropanoyl}-DArginyl-OH FAB+ MS: (M+H)+=839 Amino Acid Anal.: Pro (1.04), Phe (1.03), Cha (1.94), Arg (0.98)

EXAMPLE 111

H-Phenylalanyl-Lysyl-Alanyl-{(2R)-2-Amino-3-cyclohexylpropanoyl}-{(2S)-2-Amino-3-cyclohexylpropanoyl}-Leucyl-DArginyl-OH

FAB+ MS: (M+H)+=940

EXAMPLE 112

(N-Methyl)Phenylalanyl-Lysyl-Lysyl-{(2R)-2-Amino-3-cyclohexylpropanoyl}-Phenylalanyl-DArginyl-OH FAB+ MS: (M+H)+=892 Amino Acid Anal.: PheMe (0.93), Phe (0.96), Cha (0.93), Lys (2.01), Arg (1.03)

EXAMPLE 113

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-NH(Phenethyl)

This compound was prepared in analogy to Example 3.

FAB+ MS: (M+H)+ =970 Amino Acid Anal.: PheMe (0.88), Lys (0.99), Pro (1.00), Cha (1.88), Arg (1.01)

EXAMPLE 114

H-Phenylalanyl-Lysyl-DAlanyl-{(2S)-2-Amino-3-cyclohexylpropanoyl}-{(2S)-2-Amino-3-cyclohexylpropanoyl}-DLeucyl-DArginyl-OH

FAB+ MS: (M+H)+ =940

EXAMPLE 115

(N-Methyl)Phenylalanyl-Lysyl-Prolyl-D(2-Naphthylalanyl)Phenylalanyl-DArginyl-OH

FAB+ MS: (M+H)+ =905

EXAMPLE 116

H-Phenylalanyl-Lysyl(N-epsilon-trifluoroacetyl)-Prolyl-DGlutaminyl-{(2S)-2-Amino-3-cyclohexylpropanoyl}-DArginyl-OH FAB+ MS: (M+H)+ =924 Amino Acid Anal.: Gln (1.09), Pro (0.97), Phe (0.95), Lys (0.94), Arg (1.05)

EXAMPLE 117

H-Phenylalanyl-Lysyl-Alanyl-{(2S)-2-Amino-3-cyclohexylpropanoyl}-DLeucyl-Arginyl-OH

FAB+ MS: (M+H)+ =787

EXAMPLE 118

H-Phenylalanyl-Lysyl-Phenylalanyl-{(2R)-2-Amino-3-cyclohexylpropanoyl}-{(2S)-2-Amino-3-cyclohexylpropanoyl}-DArginyl-OH FAB+ MS: (M+H)+ =903 Amino Acid Anal.: Phe (2.00), Lys (0.98), Cha (1.89), Arg (1.02)

EXAMPLE 119

H-Phenylalanyl-Lysyl-Prolyl-{(2R)-2-Amino-3-cyclohexylpropanoyl}-Arginyl-DArginyl-OH FAB+ MS: (M+H)+ =856 Amino Acid Anal.: Phe (0.97), Cha (0.93), Lys (1.03), Arg (1.98), Pro (1.02)

EXAMPLE 120

N-Acetyl-Phenylalanyl-Lysyl-Alanyl-{(2R)-2-Amino-3-cyclohexylpropanoyl}-{(2S)-2-Amino-3-cyclohexylpropanoyl}-DArginyl-OH The trifluoroacetic acid salt of Phenylalanyl-Lysyl(N-epsilon-Cbz)-Alanyl-{(2R)-2-Amino-3-cyclohexylpropanoyl}-{(2S)-2-Amino-cyclohexylpropanoyl)-DArgininyl(N-guanidino-Tos)-OResin (0.26 g) was prepared according to the procedure described in Example 1. The peptide-resin obtained was washed with 10%-diisopropylethylamine (DIEA) in methylene chloride (3×15 mL, 45 seconds each) and methylene chloride (4×15 mL). 10%-DIEA in methylene chloride (30 mL) was introduced into the reaction vessel and acetic anhydride (2 mL) was added. It was reacted at room temperature for 40 min. The N-acetyl-peptide-resin was treated with HF and anisole, was purified by HPLC, according to the procedure mentioned in Example 2 to yield 12 mg of pure product consistent with proposed structure.

FAB+ MS: (M+H)+ =869

EXAMPLE 121

H-(4-Methyl)Phenylalanyl-Lysyl-Alanyl-{(2S)-2-Amino-3-cyclohexylpropanoyl}-Leucyl-DAlanyl-Arginyl-OH

FAB+ MS: (M+H)+ =872

EXAMPLE 122

(N-Methyl) Phenylalanyl-Lysyl-Prolyl-{(2R)-2-Amino-3-cyclohexylpropanoyl}-{(2S)-2-Amino-3-cyclohexylpropanoyl}-{2-Aminoindan-2-carboxoyl}-OH The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892.

This peptide was prepared in analogy to Example No. 322.

FAB+ MS: (M+H)+ =870

EXAMPLE 123

(N-Methyl)Phenylalanyl-Lysyl-Prolyl-{(2R)-2-Amino-3-cyclohexylpropanoyl}-(1-Naphthylalanyl)-DArginyl-OH FAB+ MS: (M+H)+ =911 Amino Acid Anal.: PheMe (0.94), Cha (0.92), Lys (0.98), Arg (1.02), Pro (1.00)

EXAMPLE 124

H-Phenylalanyl-Lysyl-Prolyl-DLeucyl-{(2S)-2-Amino-3-cyclohexylpropanoyl}-DArginyl-OH FAB+ MS: (M+H)+ =813 Amino Acid Anal.: Pro (1.21), Leu (1.18), Phe (0.89), Cha (0.90), Lys (0.80), Arg (1.01)

EXAMPLE 125

H-Phenylalanyl-Lysyl-Alanyl-{(2S)-2-Amino-3-cyclohexylpropanoyl}-Leucyl-DPhenylalanyl-Arginyl-OH FAB+ MS: (M+H)+ =991 Amino Acid Anal.: Phe (1.95), Lys (0.99), Ala (1.02), Cha (1.04), Leu (1.07), Arg (1.05)

EXAMPLE 126

H-{(2R)-2-Amino-4-phenylbutanoyl}-Lysyl-{(2S)-2-Amino-3cyclohexylpropanoyl}-{(2S)-2-Amino-3-cyclohexylpropanoyl}-Leucyl-DAlanyl-Arginyl-OH

FAB+ MS: (M+H)+ =954

EXAMPLE 127

H-{(2S)-2-Amino-4-phenylbutanoyl}-Lysyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =954

EXAMPLE 128

(N-Methyl) Phenylalanyl-Lysyl-Prolyl-{(2R)-2-Amino-3-cyclohexylpropanoyl}-Phenylalanyl-DArginyl-OH FAB+ MS: (M+H)+ =861 Amino Acid Anal.: PheMe (0.77), Phe (0.97), Cha (0.94), Lys (0.81), Arg (1.02), Pro (1.02)

EXAMPLE 129 (SEQUENCE ID NO. 3)

H-Phenylalanyl-Lysyl-Phenylalanyl-{(2S)-2-Amino-3-cyclohexylpropanoyl}-Leucyl-Arginyl-OH

FAB+ MS: (M+H)+ =863

EXAMPLE 130

(N-Methyl)Phenylalanyl-Lysyl-Prolyl-{(2R)-2-Amino-3-cyclohexylpropanoyl}-{(2S)-2-Amino-3-cyclohexylpropanoyl}-{(2R/S)-2-Amino-3-methyl-3-phenylbutanoyl}-OH N-Boc-(R/S)-beta, beta-dimethylphenylalanine ethyl ester (100 mg, 0.3 mmol) was hydrolyzed overnight with lithium hydroxide monohydrate (20 mg, 0.5 mmol) in dioxane-water (2:1, 3 m$_L$) at 70° C. to obtain N-Boc-(R/S)-beta,betadimethylphenylalanine in quantitative yield. The Boc group was removed with 4 M HCl-dioxane, and the product was coupled to N-Boc-(N-Methyl)Phenylalanyl-Lysyl-Prolyl-{(2R)-2-Amino-3-cyclohexylpropanoyl}-{(2S)-2-Amino-3-cyclohexylpropanoyl}-OH as described in Example 322. Removal of the Boc groups and separation/purification of the diastereomeric pair was accomplished as described in Example 322 to supply a combined yield of 45%.

FAB+ MS: (M+H)+ =886 Amino Acid Anal.: PheMe (0.75), Lys (1.01), Pro (0.99), Cha (1.99)

EXAMPLE 131

(N-Methyl)Phenylalanyl-Lysyl-Prolyl-{(2R)-2-Amino-3-cyclohexylpropanoyl}-{(2S)-2-Amino-3-cyclohexylpropanoyl-}-{(2R/S)-2-Amino-3-methyl-3-phenylbutanoyl}-OH This compounds was prepared as described in Example 130.

FAB+ MS: (M+H)+ =886 Amino Acid Anal.: PheMe (0.71), Lys (1.00), Pro (1.00), Cha (1.98)

EXAMPLE 132

(N-Methyl)Phenylalanyl-Lysyl-Prolyl-{(2R) -2-Amino-3-cyclohexylpropanoyl }-Phenylalanyl-{(S)-Phenylglycinyl}-OH The title compound was prepared in analogy to Example 352.

FAB+ MS: (M+H)+ =838 Amino Acid Anal.: PheMe (0.74), Lys (0.99), Pro (1.05), Cha (0.98), Phe (0.97)

EXAMPLE 133

H-Phenylalanyl-Lysyl-Prolyl-{(2R)-2-Amino-3-cyclohexylpropanoyl}-Phenylalanyl-DArginyl-OH FAB+ MS: (M+H)+ =847 Amino Acid Anal: Pro (110), Phe (2.00), Cha (0.92), Lys (0.93), Arg (0.99)

EXAMPLE 134

H-Penicillaminyl\*-Lysyl-Alanyl-{(2S)-2-Amino-3-cyclohexylpropanoyl}-Leucyl-DCysteinyl\*-Arginyl-OH

FAB+ MS: (M+H)+ =872

EXAMPLE 135

H-Phenylalanyl-Lysyl-Glycyl-{(2R)-2-Amino-3-cyclohexylpropanoyl}-Phenylalanyl-DArginyl-OH

FAB+ MS: (M+H)+ =807

EXAMPLE 136

(N-Methyl)Phenylalanyl-Lysyl-Prolyl-DTyrosyl-{(2S)-2-Amino-3-cyclohexylpropanoyl}-DArginyl-OH FAB+ MS: (M+H)+ =877 Amino Acid Anal.: Pro (1.13), PheMe (0.98), Tyr (1.02), Cha (0.94), Lys (1.00), Arg (0.92)

EXAMPLE 137

H-DPhenylalanyl-Lysyl-Alanyl-{(2R)-2-Amino-3-cyclohexylpropanoyl}-{(2S)-2-Amino-3-cyclohexylpropanoyl}-DArginyl-OH

FAB+ MS: (M+H)+ =827

EXAMPLE 138 (SEQUENCE ID NO. 4)

H-Phenylalanyl-Lysyl-Alanyl-{(2S)-2-Amino-3-cyclohexylpropanoyl}-{(2S)-2-Amino-3-cyclohexylpropanoyl}-Leucyl-Arginyl-OH FAB+ MS: (M+H)+ =940 Amino Acid Anal.: Phe (0.99), Lys (0.99), Ala (0.91), Cha (1.90), Leu (1.03), Arg (1.00)

EXAMPLE 139

(N-Methyl)Phenylalanyl-Lysyl-Prolyl-{(2R)-2-Amino-3-cyclohexylpropanoyl}-Phenylalanyl-{2-Aminoindan-2-carbonyl}-OH The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892. This peptide was prepared in analogy to Example No. 322.

FAB+ MS: (M+H)+ =864

EXAMPLE 140

(N-Methyl)Phenylalanyl-Lysyl-Prolyl-D(1-Naphthylalanyl)-(1-Naphthylalanyl)-DArginyl-OH

FAB+ MS: (M+H)+ =955

EXAMPLE 141

H-Phenylalanyl-Lysyl-Prolyl-{(2R)-2-Amino-3-cyclohexylpropanoyl}-Valyl-DArginyl-OH FAB+ MS: (M+H)+ =799 Amino Acid Anal.: Pro (1.05), Val (0.98), Phe (0.87), Cha (0.76), Lys (0.78), Arg (0.84)

EXAMPLE 142

H-{(2R/S)-2-Amino-5-phenylpentanoyl}-Lysyl-{(2S) -2-Amino-3-cyclohexylpropanoyl}-{(2S)-2-Amino-3-cyclohexylpropanoyl}-Leucyl-DAlanyl-Arginyl-OH FAB+ MS: (M+H)+ =968 Amino Acid Anal.: hhPhe (0.64), Lys (1.03), Cha (2.03), Leu (1.03), Ala (0.93), Arg (1.01)

EXAMPLE 143

(N-Methyl)Phenylalanyl-Lysyl-Prolyl-{(2R)-2-Amino-3-cyclohexylpropanoyl}-{(2S)-2-Amino-3-cyclohexylpropanoyl}-{(R/S)-2-Methyl-arginyl}-OH (R/S)-(N-delta-Cbz)-2-methyl-ornithine benzyl ester was prepared in analogy to the compound prepared for the synthesis of Example 378: $^1$H NMR (CDCl3, 300 MHz) δ1.34 (s, 3 H), 1.5–1.7 (m, 4 H), 3.15 (q, 2 H), 4.77( b, 1 H), 5.1 (s, 2 H), 5.15 (d, 2 H), 7.35 (m, 10 H); mass spectrum, m/e 371 (M+H). The title compound was obtained using the methodology reported for Example 378.

FAB+ MS: (M+H)+ =881 Amino Acid Anal.: PheMe (0.80), Lys (1.00), Pro (1.00), Cha (1.87)

EXAMPLE 144

(N-Methyl)Phenylalanyl-Lysyl-Prolyl-{(2R)-2-Amino-3-cyclohexylpropanoyl}-{(2S)-2-Amino-3-cyclohexylpropanoyl}-{(R/S)-2-Methyl-arginyl}-OH This compound was prepared using the methodology reported for Example 143.

FAB+ MS: (M+H)+ =881 Amino Acid Anal.: PheMe (0.80), Lys (1.04), Pro (0.96), Cha (1.89)

EXAMPLE 145

(N-Methyl)(p-Nitro)Phenylalanyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =912 Amino Acid Anal.: Lys (0.69), Pro (1.12), Cha (1.92), Arg (1.00)

EXAMPLE 146

H-Histidyl-Lysyl-Alanyl-{(2S)-2-Amino-3-cyclohexylpropanoyl}-{(2S)-2-Amino-3-cyclohexylpropanoyl}-Leucyl-DArginyl-OH

FAB+ MS: (M+H)+ =930

EXAMPLE 147

(N-Methyl)Phenylalanyl-Lysyl-Prolyl-{(2R)-2-Amino-3-cyclohexylpropanoyl}-Phenylalanyl-DAlanyl-OH FAB+ MS: (M+H)+ =776 Amino Acid Anal.: Ala (1.07), PheMe (0.98), Phe (1.01), Cha (0.96), Lys (0.97), Pro (1.03)

EXAMPLE 148

H-Phenylalanyl-Lysyl-Leucyl-{(2R)-2-Amino-3-cyclohexylpropanoyl}-{(2S)-2-Amino-3-cyclohexylpropanoyl}-DArginyl-OH FAB+ MS: (M+H)+ =869 Amino Acid Anal.: Leu (1.01), Phe (0.96), Cha (2.00), Lys (0.98), Arg (1.05)

EXAMPLE 149

H-Phenylalanyl-Lysyl-DPenicillaminyl*-{(2S)-2-Amino-3-cyclohexylpropanoyl}-Leucyl-DCysteinyl*-Arginyl-OH

FAB+ MS: (M+H)+ =948

EXAMPLE 150

(N-Methyl)Phenylalanyl-Phenylalanyl-Prolyl-{(2R)-2-Amino-3-cyclohexylpropanoyl}-{(2S)-2-Amino-3-cyclohexylpropanoyl}DArginyl-OH FAB+ MS: (M+H)+ =886 Amino Acid Anal.: PheMe (1.30), Phe (0.91), Pro (1.08), Cha (1.96), Arg (1.01)

EXAMPLE 151

(N-Methyl)Phenylalanyl-Lysyl-Prolyl-{(2R)-2-Amino-3-cyclohexylpropanoyl}-Phenylalanyl-Arginyl-OH FAB+ MS: (M+H)+ =861 Amino Acid Anal.: Pro (1.15), PheMe (1.13), Phe (1.04), Cha (0.83), Lys (0.96), Arg (1.04)

EXAMPLE 152

(N-Methyl)Phenylalanyl-Lysyl-Alanyl-{(2R)-2-Amino-3-cyclohexylpropanoyl}-{(2S)-2-Amino-3-cyclohexylpropanoyl}-DArginyl-OH

FAB+ MS: (M+H)+ =841

EXAMPLE 153

H-Phenylalanyl-Lysyl-Alanyl-{(2S)-2-Amino-3-cyclohexylpropanoyl}-{(2S)-2-Amino-3-cyclohexylpropanoyl}-DAlanyl-OH

FAB+ MS: (M+H)+ =855

EXAMPLE 154

H-Alanyl-Phenylalanyl-Prolyl-{(2R)-2-Amino-3-cyclohexylpropanoyl}-{(2S)-2-Amino-3-cyclohexylpropanoyl}-DArginyl-OH

FAB+ MS: (M+H)+ =796

EXAMPLE 155

(N-Methyl)Phenylalanyl-Lysyl-{(2R/S)-2-Amino-5-phenylpentanoyl}-{(2R)-2-Amino-3-cyclohexylpropanoyl}-Phenylalanyl-DArginyl -OH FAB+ MS: (M+H)+ =939 Amino Acid Anal.: PheMe ( 1.02 ), Phe (0.94), Cha (0.99), Lys (1.01), Arg (1.05)

EXAMPLE 156

(N-Methyl)Phenylglycyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =853 Amino Acid Anal.: Lys (0.96), Pro (1.12), Cha (1.99), Arg (1.04)

EXAMPLE 157

(N-Methyl)Phenylalanyl-Lysyl-Prolyl-DLysyl-Phenylalanyl-DArginyl-OH

FAB+ MS: (M+H)+ =836 Amino Acid Anal.: PheMe (1.30), Phe (0.98), Lys (2.00), Arg (1.09), Pro (0.93)

EXAMPLE 158

(N-Methyl)Phenylalanyl-Lysyl(N-epsilon-formyl)-Prolyl-{(2R)-2-Amino-3-cyclohexylpropanoyl}-{(2S)-2-Amino-3-cyclohexylpropanoyl}-DArginyl-OH FAB+ MS: (M+H)+ =895 Amino Acid Anal.: PheMe (0.92), Lys (0.99), Pro (1.13), Cha (1.92), Arg (1.01)

EXAMPLE 159

H-Phenylalanyl-Lysyl-Phenylalanyl-{(2S)-2-Amino-3-cyclohexylpropanoyl}-{(2S)-2-Amino-3-cyclohexylpropanoyl}-DArginyl-OH

FAB+ MS: (M+H)+ =903

EXAMPLE 160

(N-Methyl)Phenylalanyl-Lysyl-Prolyl-{(2R)-2-Amino-3-cyclohexylpropanoyl}-Phenylalanyl-{(2R/S)-2-Amino-3-methyl-3-phenylbutanoyl}-OH This compound was prepared in analogy to Example 130.

FAB+ MS: (M+H)+ =880 Amino Acid Anal.: PheMe (0.72), Lys (1.01), Pro (0.98), Cha (0.99), Phe (1.01)

EXAMPLE 161

(N-Methyl)Phenylalanyl-Lysyl-Prolyl-{(2R)-2-Amino-3-cyclohexylpropanoyl}-Phenylalanyl-{(2R/S)-2-Amino-3-methyl-3-phenylbutanoyl}-OH This compound was prepared as described in Example 160.

FAB+ MS: (M+H)+ =880 Amino Acid Anal.: PheMe (0.76), Lys (1.00), Pro (0.98), Cha (1.00), Phe (1.02)

EXAMPLE 162

(N-Methyl)Phenylalanyl-Lysyl-Prolyl-{(2R)-2-Amino-3-cyclohexylpropanoyl}-Phenylalanyl-Glycyl-OH FAB+ MS: (M+H)+ =762 Amino Acid Anal.: Gly (1.04), PheMe (1.02), Phe (0.95), Cha (0.97), Lys (0.91), Pro (1.11)

EXAMPLE 163

H-Phenylalanyl-Lysyl-Prolyl-Dphenylalanyl-{(2S)-2-Amino-3-cyclohexylpropanoyl}-DArginyl-OH FAB+ MS: (M+H)+ =847 Amino Acid Anal.: Pro (1.00), Phe (1.92), Cha (1.03), Lys (0.95), Arg (1.09)

EXAMPLE 164

H-DPenicillaminyl*-Lysyl-Alanyl-{(2S)-2-Amino-3-cyclohexylpropanoyl}-Leucyl-DCysteinyl*-Arginyl-OH

FAB+ MS: (M+H)+ =872

EXAMPLE 165

(N-Methyl)Phenylalanyl-Lysyl-Prolyl-{(2R)-2-Amino-3-cyclohexylpropanoyl}-Tryptophanyl-DArginyl-OH FAB+ MS: (M+H)+ =900 Amino Acid Anal.: Pro (1.11), PheMe (1.02), Cha (1.04), Lys (0.84), Trp (0.84), Arg (1.15)

EXAMPLE 166

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-OH

FAB+ MS: (M+H)+ =867

EXAMPLE 167

H-Phenylalanyl-Aspartyl-{(2S)-2-Amino-3-cyclohexylpropanoyl}-{(2S)-2-Amino-3-cyclohexylpropanoyl}-Leucyl-DAlanyl-Arg

FAB+ MS: (M+H)+ =927

EXAMPLE 168

(N-Methyl)Phenylalanyl-Lysyl-Prolyl-{(2R)-2-Amino-3-cyclohexylpropanoyl}-Tyrosyl(O-Methyl)-DPhenylalanyl-OH

FAB+ MS: (M+H)+ =882

EXAMPLE 169

(N-Methyl)Phenylalanyl-Lysyl-Prolyl-DArginyl-Phenylalanyl-DArginyl-OH

FAB+ MS: (M+H)+ =864 Amino Acid Anal.: PheMe (1.03), Phe (1.00), Lys (0.93), Arg (2.07), Pro (0.89)

EXAMPLE 170

(N-Methyl)Tyrosyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =883 Amino Acid Anal.: Lys (0.93), Pro (1.10), Cha (1.99), Arg (1.07)

EXAMPLE 171 (SEQUENCE ID NO. 5)

H-Phenylalanyl-Lysyl-Alanyl-{(2S)-2-Amino-3-cyclohexylpropanoyl}-{(2S)-2-Amino-3-cyclohexylpropanoyl}-Leucyl-Lysyl-OH

FAB+ MS: (M+H)+ =912

EXAMPLE 172

(N-Methyl)Phenylalanyl-Lysyl-Arginyl-{(2R)-2-Amino-3-cyclohexylpropanoyl}-Phenylalanyl-DArginyl-OH FAB+ MS: (M+H)+ =920 Amino Acid Anal.: PheMe (1.04), Phe (0.95), Cha (0.95), Lys (0.99), Arg (2.06)

EXAMPLE 173

(N-Methyl)Phenylalanyl-Lysyl(N-epsilon-trifluoroacetyl)-Prolyl-DPhenylalanyl-{(2S)-2-Amino-3-cyclohexylpropanoyl}-DArginyl-OH FAB+ MS: (M+H)+ =957 Amino Acid Anal.: Pro (0.98) PheMe (0.90), Phe (1.00), Cha (1.04), Lys (1.00), Arg (1.07)

EXAMPLE 174

H-Lysyl-Phenylalanyl-Alanyl-{(2S)-2-Amino-3-cyclohexylpropanoyl}-{(2R)-2-Amino-3-cyclohexylpropanoyl}-DArginyl-OH

FAB+ MS: (M+H)+ =827

EXAMPLE 175

(N-Methyl)Phenylalanyl-Lysyl-Prolyl-{(2R)-2-Amino-3-cyclohexylpropanoyl}-Phenylalanyl-{(R/S)-t-Butylalanyl}-OH This peptide was constructed as described in Example No. 322.

FAB+ MS: (M+H)+ =832 Amino Acid Anal.: PheMe (1.06), Phe (0.96), Lys (0.99), Pro (1.04), Cha (0.83), t-butylAla (1.03)

EXAMPLE 176

(N-Methyl)Phenylalanyl-Lysyl-Prolyl-{(2R)-2-Amino-3-cyclohexylpropanoyl}-Phenylalanyl-{(R/S)-t-Butylalanyl}-OH This peptide was prepared in analogy to Example No. 322.

FAB+ MS: (M+H)+ =832 Amino Acid Anal.: PheMe (1.08), Phe (0.91), Lys (0.94), Pro (0.99), Cha (0.77), t-butylAla (0.97)

EXAMPLE 177

(N-Methyl)Phenylalanyl-Lysyl-Prolyl-{(2R)-2-Amino-3-cyclohexylpropanoyl}-Tyrosyl(O-Me)-DArginyl-OH

FAB+ MS: (M+H)+ =905

EXAMPLE 178

H-Phenylalanyl-Lysyl-Prolyl-{(2R)-2-Amino-3-cyclohexylpropanoyl}-DProlyl-DArginyl-OH

FAB+ MS: (M+H)+ =797

EXAMPLE 179

H-Phenylalanyl-Lysyl-Alanyl-{(2S)-2-Amino-3-cyclohexylpropanoyl}-Leucyl-DArginyl-OH

FAB+ MS: (M+H)+ =787

EXAMPLE 180

(N-Methyl)Phenylalanyl-Lysyl-Arginyl-{(2R)-2-Amino-3-cyclohexylpropanoyl}-Phenylalanyl-DPhenylalanyl-OH

FAB+ MS: (M+H)+ =911

EXAMPLE 181

(N-Methyl)Phenylalanyl-Lysyl-Prolyl-{(2R)-2-Amino-3-cyclohexylpropanoyl}-Phenylalanyl-Phenylalanyl-OH FAB+ MS: (M+H)+ =852 Amino Acid Anal.: Phe (2.07), Cha (0.88), Lys (0.99), Pro (1.06)

EXAMPLE 182

N-Acetyl-{(Z)-2-Amino-3-phenyl-2-propenoyl}-Lysyl-Prolyl-{(2R)-2-Amino-3-cyclohexylpropanoyl}-Phenylalanyl-DArginyl-OH The C-terminal pentapeptide is prepared using standard solid phase peptide synthesis techniques. The lysine is incorporated with the epsilon nitrogen protected with Fmoc which survives HF cleavage of the peptide from the resin and removal of the other protecting groups. Z-Acetamidocinnamic acid is coupled to the pentapeptide in solution phase employing the mixed acid anhydride method. The Fmoc group is subsequently removed with piperidine, and the crude peptide is purified by HPLC.

EXAMPLE 183

(N-Methyl)Alanyl-Lysyl-Prolyl-{(2R) -2-Amino-3-cyclohexylpropanoyl}-{(2S)-2-Amino-3-cyclohexylpropanoyl}-DArginyl-OH FAB+ MS: (M+H)+ =791 Amino Acid Anal.: Lys (0.87), Pro (1.12), Cha (2.01), Arg (1.01)

EXAMPLE 184

H-Phenylalanyl-Lysyl-Alanyl-{(2S)-2-Amino-3-cyclohexylpropanoyl}-{(2S)-2-Amino-3-cyclohexylpropanoyl}-DAlanyl-Arginyl-OH

FAB+ MS: (M+H)+ =898

EXAMPLE 185

(N-Methyl)Phenylalanyl-{(2S)-2-Amino-3-cyclohexylpropanoyl}-Prolyl-{(2R)-2-Amino-3-cyclohexylpropanoyl}-{(2S)-2-Amino-3-cyclohexylpropanoyl}-DArginyl-OH

FAB+ MS: (M+H)+ =892

EXAMPLE 186

(N-Methyl)Phenylalanyl-Lysyl-{(2S)-2-Amino-4-phenylbutanoyl}-{(2R)-2-Amino-3-cyclohexylpropanoyl}-Phenylalanyl-DArginyl-OH FAB+ MS: (M+H)+ =925 Amino Acid Anal.: PheMe (1.01), Phe (0.99), Cha/hPhe (1.92), Lys (1.00), Arg (1.01)

EXAMPLE 187

(N-Methyl)Phenylalanyl-Norleucyl-Prolyl-{(2R)-2-Amino-3-cyclohexylpropanoyl}-{(2S)-2-Amino-3-cyclohexylpropanoyl}-DArginyl-OH FAB+ MS: (M+H)+ =852 Amino Acid Anal.: Nle (0.95), Pro (1.07), Cha (1.85), Arg (0.98)

EXAMPLE 188

H-Phenylalanyl-Lysyl-Alanyl-{(2S)-2-Amino-3-cyclohexylpropanoyl}-{(2R)-2-Amino-3-cyclohexylpropanoyl}Leucyl-DArginyl-OH

FAB+ MS: (M+H)+ =940

EXAMPLE 189

(N-Methyl)Phenylalanyl-Arginyl-Prolyl-{(2R)-2-Amino-3-cyclohexylpropanoyl}-Phenylalanyl-DArginyl-OH FAB+ MS: (M+H)+ =889 Amino Acid Anal.: PheMe (1.05), Phe (0.97), Cha (0.97), Arg (1.96), Pro (1.07)

EXAMPLE 190

(N-Methyl)Phenylalanyl-Lysyl-Glycyl-{(2R)-2-Amino-3-cyclohexylpropanoyl}-Phenylalanyl-DArginyl-OH FAB+ MS: (M+H)+ =821 Amino Acid Anal.: Gly (1.02), PheMe (1.07), Phe (1.07), Cha (0.84), Lys (0.94), Arg (1.06)

EXAMPLE 191

H-DPhenylalanyl-Lysyl-Alanyl-{(2S)-2-Amino-3-cyclohexylpropanoyl}-{(2S)-2-Amino-3-cyclohexylpropanoyl}-Leucyl-DArginyl-OH

FAB+ MS: (M+H)+ =940

EXAMPLE 192

(N-Methyl)Phenylalanyl-Lysyl-Prolyl-{(2R)-2-Amino-3-cyclohexylpropanoyl}-Phenylalanyl-{(2RS)-2-Amino-2-methyl-3-phenylpropanoyl}-OH (2RS)-2-Amino-2-methyl-3-phenylpropanoic acid was coupled to Boc-(N-methyl)phenylalanyl-lysyl (N-epsilon-Boc)-prolyl-{(2R)-2-amino-3-cyclohexylpropanoyl}-phenylalanyl-OH as described in Example 322. Deprotection and HPLC purification also as described in the same example provided the title compound in 33% yield.

FAB+ MS: (M+H)+ =866 Amino Acid Anal.: PheMe (0.85), Lys (0.95), Pro (1.00), Cha (0.96), Phe (1.05)

EXAMPLE 193

(N-Methyl)Phenylalanyl-Lysyl(N-epsilon-nicotynyl)-Prolyl{(2R)-2-Amino-3-cyclohexylpropanoyl}-Phenylalanyl-DArginyl-OH The protected peptide resin; Boc-(N-Methyl)-Phenylalanyl-Lysyl-Prolyl-{(2R)-2-Amino-3-cyclohexylpropanoyl}-Phenylalanyl-DArginyl(N-guanidino-Tos)-O-resin was synthesized by the method described in Example No. 59. The N-epsilon-amino group of the lysyl residue was coupled with nicotinic acid (10 molar equivalents) in the presence of diisopropylcarbodiimide (DIPCDI) (10 molar equivalents) in DMF (15 mL) at room temperature for 5 h. The resin obtained was washed with DMF (3×10 mL) and methylene chloride (3×10 mL), and the title compound was obtained by the method described in Example 2.

FAB+ MS: (M+H)+ =966

EXAMPLE 194

H-Phenylalanyl-Lysyl-Prolyl-{(2R)-2-Amino-3-cyclohexylpropanoyl}-{(2S)-2-Amino-3-cyclohexylpropanoyl}-Arginyl-OH

FAB+ MS: (M+H)+ =853

EXAMPLE 195

H-Phenylalanyl-Lysyl-Alanyl-{(2S)-2-Amino-3-cyclohexylpropanoyl}-{(2S)-2-Amino-3-cyclohexylpropanoyl}-DLeucyl-Arginyl-OH

FAB+ MS: (M+H)+ =940

EXAMPLE 196

H-{(2S)-2-Amino-3-cyclohexylpropanoyl}-Lysyl-Prolyl-{(2R)-2-Amino-3-cyclohexylpropanoyl}-{(2S)-2-Amino-3-cyclohexylpropanoyl}-DArginyl-OH

FAB+ MS: (M+H)+ =859

EXAMPLE 197

(N-Methyl)Phenylalanyl-Lysyl-Prolyl-{(2R)-2-Amino-3-cyclohexylpropanoyl}-{(2S)-2-Amino-3-cyclohexylpropanoyl}-Phenylalanyl-OH FAB+ MS: (M+H)+ =858 Amino Acid Anal.: PheMe (0.91), Phe (1.19), Lys (0.97), Pro (0.91)

EXAMPLE 198

(N-Methyl)Leucyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =833 Amino Acid Anal.: Lys (0.96), Pro (1.04), Cha (1.97), Arg (1.01)

EXAMPLE 199

H-Phenylalanyl-Lysyl-Phenylalanyl-{(2S)-2-Amino-3-cyclohexylpropanoyl}-Leucyl-DArginyl-OH

FAB+ MS: (M+H)+ =863

EXAMPLE 200

H-Phenylalanyl-Lysyl(epsilon-N)-Prolyl-{(2R)-2-Amino-3-cyclehexylpropanoyl}-{(2S)-2-Amino-3-cyclohexylpropanoyl}-DArginyl-{(2S)-2-Amino-3-cyclohexylpropanoyl}

The peptide H-Phenylalanyl-Lysyl (epsilon-N[2-Cl-Z])-Prolyl-{ (2R)-2-Amino-3-cyclohexylpropanoyl}-{(2S)-2-Amino-3-cyclohexylpropanoyl}-DArginyl(N-guanidino-Tos)-{(2S)-2-Amino-3-cyclohexylpropanoyl)-O-Resin was prepared by the methods presented in Examples 1 and 2. The peptide-resin (0.76 mmol) was suspended in dry dimethylformamide (6 mL) under nitrogen then ethyl trifluoroacetate (0.6 mL, 7.6 mmol) and triethylamine (0.7 mL, 7.6 mmol) were added. The suspension was stirred gently overnight, the resin removed by filtration, washed with several portions of methylene chloride, and dried by aspiration. The peptide was then cleaved from the resin and purified by HPLC as described in Example 2. The resulting peptide (134 mg, 0.11 mmol) was dissolved in 40% aqueous acetonitrile (30 mL); 1 N hydrochloric acid (0.5 mL) was added and the mixture was lyophilized to give the hydrochloride salt of the peptide. The resulting white powder was dissolved in dry dimethylformamide (12 mL) at −20° C. under nitrogen. Diphenylphosphoryl azide (25.8 uL, 0.12 mmol) was added followed by triethylamine (70 uL, 0.5 mmol). The mixture was stored in a freezer at −15° C. for 12 d. The dimethylformamide was then removed in vacuo. The resulting oil was purified by HPLC as described in Example 2. The peptide (21.4 mg) was dissolved in methanol (0.9 mL) and water (0.9 mL) and saturated aqueous sodium carbonate solution (0.4 mL) was added. The mixture was stirred overnight at room temperature, then purified by HPLC to supply the title compound (6 mg, 5%).

FAB+ MS: (M+H)+ =988

EXAMPLE 201

H-Phenylalanyl-Lysyl-Prolyl-DGlutaminyl-{(2S)-2-Amino-3-cyclohexylpropanoyl}-DArginyl-OH FAB+ MS: (M+H)+ =828 Amino Acid Anal.: Glx (1.05), Phe (0.96), Cha (0.93), Lys (1.01), Arg (0.99), Pro (1.13)

EXAMPLE 202

9-Fluorenylmethyloxycarbonyl-Phenylalanyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =1075 Amino Acid Anal.: Phe (0.97), Lys (0.99), Pro (1.19), Cha (1.99), Arg (1.04)

EXAMPLE 203

H-Phenylalanyl-Lysyl-Alanyl-{(2S)-2-Amino-3-cyclohexylpropanoyl}-{(2S)-2-Amino-3-cyclohexylpropanoyl}-Leucyl-DArginyl -NHNH2

FAB+ MS: (M+H)+ =954

EXAMPLE 204

(N-Methyl)Phenylalanyl-Phenylalanyl-Prolyl-{(2R)-2-Amino-3-cyclohexylpropanoyl}-Phenylalanyl-DArginyl-OH FAB+ MS:(M+H)+ =880 Amino Acid Anal.: PheMe (1.11), Phe (1.84), Cha (0.99), Arg (1.08), Pro (1.08)

EXAMPLE 205

(N-Methyl)Phenylalanyl-Lysyl-Prolyl-{(2R/S)-2-Amino-5-phenylpentanoyl}-Alanyl-DArginyl-OH FAB+ MS: (M+H)+ =807 Amino Acid Anal.: Pro (1.15), Ala (0.78), PheMe (0.99), Lys (0.92), Arg (1.15)

EXAMPLE 206

H-Phenylalanyl-DLysyl-Alanyl-{(2S)-2-Amino-3-cyclohexylpropanoyl}-{(2S)-2-Amino-3-cyclohexylpropanoyl}-Leucyl-DArginyl-OH

FAB+ MS: (M+H)+ =940

EXAMPLE 207

(N-Methyl)Phenylalanyl-Lysyl-Arginyl-{(2R)-2-Amino-3-cyclohexylpropanoyl}-{(2S)-2-Amino-3-cyclohexylpropanoyl}-DAlanyl-OH FAB+ MS: (M+H)+ =842 Amino Acid Anal.: Ala (0.99), PheMe (1.03), Cha (1.95), Lys (0.99), Arg (1.02)

EXAMPLE 208

(2R)-2-Amino-3-cyclohexylpropanoyl}-Phenylalanyl-Lysyl-Alanyl-DArginyl-Phenylalanyl

This compound was prepared in analogy to Example 257.

FAB+ MS: (M+H)+ =803

EXAMPLE 209

H-Arginyl-Phenylalanyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =1009 Amino Acid Anal.: Pro (0.95), Phe (0.94), Cha (2.03), Lys (0.96), Arg (2.12)

EXAMPLE 210

H-Phenylalanyl-Lysyl-Alanyl-{(2S)-2-Amino-3-cyclohexylpropanoyl}-DLeucyl-DArginyl-OH

FAB+ MS: (M+H)+ =787

EXAMPLE 211

(N-Methyl)Phenylalanyl-Lysyl-prolyl-{(2R)-2-Amino-3-cyclohexylpropanoyl}-Dphenylalanyl-Dphenylalanyl-OH

FAB+ MS: (M+H)+ =852

EXAMPLE 212

(N-Methyl)Phenylalanyl-Lysyl-Prolyl-{(2R)-2-Amino-3-cyclohexylpropanoyl}-Phenylalanyl-DPhenylalanyl-OH FAB+ MS: (M+H)+ =852 Amino Acid Anal.: PheMe (0.94), Phe (2.09), Cha (0.89), Lys (0.99), Pro (1.09)

EXAMPLE 213

H-Histidyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =843 Amino Acid Anal.: His/-Cha (2.89), Lys (0.99), Pro (1.01), Arg (1.00)

EXAMPLE 214

H-Phenylalanyl-Lysyl-Alanyl-{(2S)-2-Amino-3-cyclohexylpropanoyl}-{(2S)-2-Amino-3-cyclohexylpropanoyl}-Leucyl-DArg

FAB+ MS: (M+H)+ =940

EXAMPLE 215

(N-Methyl)Phenylalanyl-{(2S)-2-Amino-3-cyclohexylpropanoyl}-Prolyl-{(2R)-2-Amino-3-cyclohexylpropanoyl}-Phenylalanyl-DArginyl-OH

FAB+ MS: (M+H)+ =886

EXAMPLE 216

(N-Methyl)Phenylalanyl-Lysyl-Tryptophanyl-{(2R)-2-Amino-3-cyclohexylpropanoyl}-Phenylalanyl-DArginyl-OH FAB+ MS: (M+H)+ =950 Amino Acid Anal.: Phe (0.98), Cha (0.97), Lys (2.01),.Arg (1.06), Pro (0.94)

EXAMPLE 217

H-Phenylalanyl-Lysyl-Alanyl-{(2R)-2-Amino-3-cyclohexylpropanoyl}-{(2R)-2-Amino-3-cyclohexylpropanoyl}-DArginyl-OH

FAB+ MS: (M+H)+ =827

EXAMPLE 218 (Sequency ID No. 6)

H-Phenylalanyl-Lysyl-Alanyl-Glycyl-{(2S)-2-Amino-3-cyclohexylpropanoyl}-Leucyl-Glycyl-OH

FAB+ MS: (M+H)+ =745

EXAMPLE 219

(N-Methyl)Phenylalanyl-Lysyl-Prolyl-{(2R/S)-2-Amino-3-cyclohexyl-2-methylpropanoyl}-Phenylalanyl-DArginyl-OH {Boc-(2R/S)-2-Amino-3-cyclohexyl-2-methylpropanoic acid} was prepared by hydrogenation of Boc-alpha-methylphenylalanine which was prepared as described in Example No. 232. The reduction was accomplished over a one week period using 1 g of 5% rhodium on carbon for each gram of amino acid in methanol under hydrogen (4 atm). MS: (M+H)+ =286. The peptide was synthesized as described in Example No. 232.

FAB+ MS: (M+H)+ =875 Amino Acid Anal.: PheMe (1.15), Phe (0.91), Lys (0.94), Arg (1.15), Pro (0.90)

EXAMPLE 220

(N-Methyl)Phenylalanyl-Lysyl-Prolyl-{(2R)-2-Amino-3-cyclohexylpropanoyl}-{(2S)-2-Amino-4-phenylbutanoyl}-DArginyl-OH FAB+ MS: (M+H)+ =875 Amino Acid Anal.: Pro (0.97), PheMe (1.00), Cha (1.98), Lys (0.98), Arg (1.08)

EXAMPLE 221

(N-Methyl)Phenylalanyl-Lysyl-Prolyl-{(2R)-2-Amino-3-cyclohexylpropanoyl}-{(2R)-2-Amino-4-phenylbutanoyl}-DArginyl-OH FAB+ MS: (M+H)+ =875 Amino Acid Anal.: Pro (1.05), PheMe (1.01), Cha (1.92), Lys (0.97), Arg (1.05)

EXAMPLE 222

H-Phenylalanyl-Lysyl-Alanyl-{(2S)-2-Amino-3-cyclohexylpropanoyl}-{(2R)-2-Amino-3-cyclohexylpropanoyl}-DArginyl-OH

FAB+ MS: (M+H)+ =827

EXAMPLE 223

H-Phenylalanyl-Lysyl-Arginyl-{(2R)-2-Amino-3-cyclohexylpropanoyl}-{(2S)-2-Amino-3-cyclohexylpropanoyl}-DAlanyl-OH FAB+ MS: (M+H)+ =827 Amino Acid Anal.: Ala (0.97), Phe (0.96), Cha (2.03), Lys (1.05), Arg (1.01)

EXAMPLE 224

(N-Methyl)Phenylalanyl-Lysyl-Prolyl-D(1-Naphthylalanyl)-Phenylalanyl-DArginyl-OH

FAB+ MS: (M+H)+ =905

EXAMPLE 225

H-DArginyl-Phenylalanyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =1009 Amino Acid Anal.: Pro (0.93), Phe (0.96), Cha (2.02), Lys (0.97), Arg (2.12)

EXAMPLE 226

H-Phenylalanyl-Lysyl-{(2S)-2-Amino-3-cyclohexylpropanoyl}-{(2S)-2-Amino-3-cyclohexylpropanoyl}-Leucyl-DAlanyl-Arginyl-OH

FAB+ MS: (M+H)+ =940

EXAMPLE 227

(N-Methyl)Phenylalanyl-Lysyl-Prolyl-{(2R)-2-Amino-3-cyclohexylpropanoyl}-DPhenylalanyl-Phenylalanyl-OH

FAB+ MS:(M+H)+ =852

EXAMPLE 228

(N-Methyl)Phenylalanyl-Lysyl-Prolyl-{(2R)-2-Amino-3-cyclohexylpropanoyl}-{(2S)-2-Amino-3-cyclohexylpropanoyl}-DPhenylalanyl-OH FAB+ MS: (M+H)+ =858 Amino Acid Anal.: PheMe (0.98), Phe (1.11), Cha (1.85), Lys (0.99), Pro (1.06)

EXAMPLE 229

H-Sarcosyl-Lysyl-Prolyl-{(2R)-2-Amino-3-cyclohexylpropanoyl}-{(2S)-2-Amino-3-cyclohexylpropanoyl}-DArginyl-OH FAB+ MS:(M+H)+ =777 Amino Acid Anal.: Sar (0.94), Lys (0.97), Pro (1.02), Cha (1.95), Arg (0.98)

EXAMPLE 230 (SEQUENCE ID NO. 7)

H-Phenylalanyl-Lysyl-Alanyl-{(2S)-2-Amino-3-cyclohexylpropanoyl}-{(2S)-2-Amino-3-cyclohexylpropanoyl}-Leucyl-OMe

FAB+ MS: (M+H)+ =798

EXAMPLE 231

(N-Methyl)Phenylalanyl-Tyrosyl-Prolyl-{(2R)-2-Amino-3-cyclohexylpropanoyl}-Phenylalanyl-DArginyl-OH

FAB+ MS: (M+H)+ = 896

EXAMPLE 232

H-{(2R/S)-2-Methylphenylalanyl}-Lysyl-Prolyl-{(2R)-2-Amino-3-cyclohexylpropanoyl}-Phenylalanyl-DArginyl-OH This compound was prepared as described in Examples 1 and 2 with the following exception. 1-Hydroxybenzotriazole (0.5g/g amino acid) was employed as a coupling aid during the incorporation of Boc-2-methylphenylalanine. Commercially available alpha-methyl-D,L-phenylalanine was converted to its t-butyl carbamate with BOC-ON as described in the following reference: Itoh, M.; Hagiwara, D.; Kamiya, T. *Bull. Chem. Soc. Jpn.*, 1977, 50, 718. MS: (M+H)+ = 280.

FAB+ MS: (M+H)+ = 861 Amino Acid Anal.: Phe (1.03), Cha (0.93), Lys (0.99), Arg (0.98), Pro (1.05)

EXAMPLE 233

H-{(2R/S)-2-Methylphenylalanyl}-Lysyl-Prolyl-{(2R)-2-Amino-3-cyclohexylpropanoyl}-Phenylalanyl-DArginyl-OH FAB+ MS: (M+H)+ = 861 Amino Acid Anal.: Phe (1.01), Cha (0.96), Lys (0.99), Arg (1.01), Pro (1.17)

EXAMPLE 234

H-Phenylalanyl-Lysyl-Alanyl-{(2R)-2-Amino-3-cyclohexylpropanoyl}-{(2S)-2-Amino-3-cyclohexylpropanoyl}-Arginyl-OH

FAB+ MS: (M+H)+ = 827

EXAMPLE 235 (SEQUENCE ID NO. 8)

H-Phenylalanyl-Lysyl-Alanyl-{(2S)-2-Amino-3-cyclohexylpropanoyl}-Glycyl-Leucyl-Glycyl-OH

FAB+ MS: (M+H)+ = 745

EXAMPLE 236

(N-Methyl)Phenylalanyl-Lysyl-Prolyl-{(2R)-2-Amino-3-cyclohexylpropanoyl}-{(2RS)-2-Amino-3-cyclohexyl-2-methylpropanoyl}-DArginyl-OH FAB+ MS: (M+H)+ = 881 Amino Acid Anal.: PheMe (1.12), Cha (0.96), Lys (0.98), Arg (1.07), Pro (0.95)

EXAMPLE 237

(N-Methyl)Phenylalanyl-Lysyl-Prolyl-{(2R)-2-Amino-3-cyclohexylpropanoyl}-{(2RS)-2-Amino-5-phenylpentanoyl}-DArginyl-OH

FAB+ MS: (M+H)+ = 889

EXAMPLE 238

H-Phenylalanyl-Lysyl-DHistidyl-{(2S)-2-Amino-3-cyclohexylopanoyl}-{(2S)-2-Amino-3-cyclohexylpropanoyl}-Leucyl-Arginyl-OH

FAB+ MS: (M+H)+ = 1006

EXAMPLE 239

H-Phenylalanyl-Alanyl-Arginyl-{(2R)-2-Amino-3-cyclohexylpropanoyl}-{(2S)-2-Amino-3-cyclohexylpropanol}-DArginyl-OH FAB+ MS: (M+H)+ = 855 Amino Acid Anal.: Ala (0.99), Phe (0.98), Cha (1.48), Arg (2.03)

EXAMPLE 240

(N-Methyl)Phenylalanyl-Lysyl-Prolyl-{(2R)-2-Amino-3-cyclohexylpropanoyl}-Phenylalanyl-Alanyl-OH FAB+ MS: (M+H)+ = 776 Amino Acid Anal.: Ala (1.02), PheMe (0.92), Phe (0.93), Cha (0.92), Lys (0.93), Pro (0.99)

EXAMPLE 241 (SEQUENCE ID NO. 9)

H-Phenylalanyl-Lysyl-Arginyl-Arginyl-Leucyl-Glycyl-Arginyl-OH

FAB+ MS: (M+H)+ = 932

EXAMPLE 242

H-Phenylalanyl-Lysyl-Alanyl-{(2S)-2-Amino-3-cyclohexylpropanoyl}-Leucyl-DAlanyl-Arginyl-OH

FAB+ MS: (M+H)+ = 858

EXAMPLE 243

(N-Methyl)Phenylalanyl-Lysyl-Prolyl-{(2S)-2-Amino-3-cyclohexylpropanoyl}-DPhenylalanyl-Phenylalanyl-OH

FAB+ MS: (M+H)+ = 852

EXAMPLE 244 (SEQUENCE ID NO. 10)

(N-Methyl)Phenylalanyl-Lysyl-Prolyl-Glycyl-Phenylalanyl-Arginyl-OH

FAB+ MS: (M+H)+ = 765 Amino Acid Anal.: Gly (1.09), PheMe (0.90), Phe (1.01), Lys (1.02), Arg (0.99), Pro (0.90)

EXAMPLE 245

H-Phenylalanyl-Lysyl-DProlyl-{(2R)-2-Amino-3-cyclohexylpropanoyl}-{(2S)-2-Amino-3-cyclohexylpropanoyl}-DArginyl-OH FAB+ MS: (M+H)+ = 853 Amino Acid Anal.: Phe (0.94), Lys (0.87), Pro (1.08), .Cha (2.08), Arg (1.06)

EXAMPLE 246

H-Phenylalanyl-Lysyl-{(2S)-2-Amino-3-cyclohexylpropanoyl}-{(2S)-2-Amino-3-cyclohexylpropanoyl}-DAlanyl-Arginyl-OH

FAB+ MS: (M+H)+ = 827

EXAMPLE 247

(N-Methyl)Phenylalanyl-Tyrosyl-Prolyl-{(2R)-2-Amino-3-cyclohexylpropanoyl}-{(2S)-2-Amino-3-cyclohexylpropanoyl}-DArginyl-OH

FAB+ MS: (M+H)+ = 902

EXAMPLE 248

(N-Methyl)Phenylalanyl-Lysyl-Prolyl-{(2R)-2-Amino-3-cyclohexylpropanoyl}-{2-Amino-2-methylpropanoyl}-DArginyl-OH FAB+ MS: (M+H)+ = 799 Amino Acid Anal.: PheMe (0.99), Cha (0.94), Lys (1.01), Arg (0.99), Pro (1.15)

EXAMPLE 249

H-Phenylalanyl-Lysyl-Alanyl-{(2R)-2-Amino-3-cyclohexylpropanoyl}-{(2R)-2-Amino-3-cyclohexylpropanoyl}-Arginyl-OH

FAB+ MS: (M+H)+ = 827

EXAMPLE 250

H-DPhenylalanyl-Lysyl-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =940 Amino Acid Anal.: Phe (0.99), Lys (0.95), Cha (1.97), Leu (1.08), Ala (0.97), Arg (1.01)

EXAMPLE 251

(N-Methyl)Phenylalanyl-Lysyl-prolyl-DNorleucyl-phenylalanyl-DArginyl-OH

FAB+ MS: (M+H)+ =821 Amino Acid Anal.: PheMe (1.07), Nle (1.03), Phe (0.96), Lys (0.93), Arg (1.05), Pro (1.03)

EXAMPLE 252

(N-Methyl)Phenylalanyl-Lysyl-Prolyl-{(2R)-2-Amino-3-cyclohexylpropanoyl}-Tyrosyl-DArginyl-OH FAB+ MS: (M+H)+ =877 Amino Acid Anal.: Pro (1.00), PheMe (0.98), Cha (0.95), Lys (0.99), Arg (1.08)

EXAMPLE 253 (SEQUENCE I.D. NO. 11)

(N-Methyl)Phenylalanyl-Lysyl-Alanyl-{(2S)-2-Amino-3-cyclohexylpropanoyl}-Alanyl-Leucyl-Arginyl-NHNH$_2$

FAB+ MS: (M+H)+ =886

EXAMPLE 254

(N-Methyl)Phenylalanyl-Lysyl-Prolyl-{(2R)-2-Amino-3-cyclohexylpropanoyl}-{(2S)-2-Amino-3-cyclohexylpropanoyl}-DTyrosyl-OH

FAB+ MS: (M+H)+ =874

EXAMPLE 255

(N-Methyl)Phenylalanyl-{(2S)2-Amino-6-ureido-hexanoyl}-Prolyl-{(2R)-2-Amino-3-cyclohexylpropanoyl}-Phenylalanyl-DArginyl-OH FAB+ MS: (M+H)+ =904 Amino Acid Anal.: PheMe (0.96), Phe (0.98), Cha (0.92), Cit (0.78), Arg (1.02), Pro (1.00)

EXAMPLE 256 (SEQUENCE ID NO. 12)

H-Phenylalanyl-Arginyl-Methionyl-Arginyl-Leucyl-Glycyl-Arginyl-OH

FAB+ MS: (M+H)+ =935

EXAMPLE 257

{(2R/S)-2-Amino-5-phenylpentanoyl}-Lysyl-Prolyl-{(2R)-2-Amino-3-cyclohexylpropanoyl}-{(2S)-2-Amino-3-cyclohexylpropanoyl}-DArginyl

The peptide salt H-{(2R/S)-2-Amino-5-phenylpentanoyl}-Lysyl(N-epsilon-Trifluoroacetyl)-Prolyl-{(2R)-2-Amino-3-cyclohexylpropanoyl}-{(2S)-2-Amino-3-cyclohexylpropanoyl}-DArginyl-OH-2TFA was prepared according to the protocol described in Examples 1 and 2. The peptide (146 mg, 0.12 mmol) was then dissolved in 40% CH$_3$CN (30 mL); 1 N HCl (0.5 mL, 0.24 mmol) was added and the mixture was lyophilized to give the hydrochloride salt of the peptide. The resulting white powder was dissolved in dry DMF (15 mL) at −20° C. under N$_2$. Diphenylphosphoryl azide (30 uL, 0.14 mmol) was added followed by triethylamine (83 uL, 0.6 mmol). The mixture was stored in a freezer at −15° C. for 12 d. The dimethylformamide was then removed in vacuo employing a 40° C. water bath. The resulting oil was purified by HPLC as described in Example 2 to furnish the cyclic peptide in which the epsilon amine of the lysine residue remained protected as its trifluoroacetyl amide. The peptide (43 mg) was dissolved in methanol (2 mL) and water (1.5 mL) and saturated aqueous sodium carbonate solution (0.1 mL) was added. The mixture was stirred overnight at ambient temperature then purified by HPLC to provide the title compound (30 mg, 29%).

FAB+ MS: (M+H)+ =863 Amino Acid Anal.: Lys (0.98), Pro (1.10), Cha (1.89), Arg (0.99), hhPhe (0.73)

EXAMPLE 258

H-{(2R/S)-2-Amino-5-phenylpentanoyl}-{(2S)-2-Amino-3-cyclohexylpropanoyl}-Alanyl-Leucyl-DAlanyl-Arginyl-OH

FAB+ MS: (M+H)+ =758

EXAMPLE 259

H-{(2R/S)-2-Amino-5-phenylpentanoyl}-{(2S)-2-Amino-3-cyclohexylpropanoyl}-Alanyl-Leucyl-DAlanyl-Arginyl-OH

FAB+ MS: (M+H)+ =758

EXAMPLE 260

(N-Methyl)Phenylalanyl-Alanyl-Lysyl-{(2R)-2-Amino-3-cyclohexylpropanoyl}-Phenylalanyl-DArginyl-OH FAB+ MS: (M+H)+ =835 Amino Acid Anal.: PheMe (1.20), Ala (1.02), Lys (0.97), Cha (0.95), Phe (1.00), Arg (1.01)

EXAMPLE 261

H-Phenylalanyl-Lysyl-DAlanyl-{(2R)-2-Amino-3-cyclohexylpropanoyl}-{(2S)-2-Amino-3-cyclohexylpropanoyl}-DArginyl-OH

FAB+ MS: (M+H)+ =827

EXAMPLE 262

N-Acetyl-Phenylalanyl-Lysyl-Ornithyl-(2R)-2-Amino-3-cyclohexylpropanoyl}-{(2S)-2-Amino-3-cyclohexylpropanoyl}-Arginyl

The trifluoroacetic acid salt of H-phenylalanyl-lysyl(N-epsilon-Fmoc)-ornithyl(n-delta-Cbz)-{(2R)-2-amino-3-cyclohexylpropanoyl}-{(2S)-2-amino-3-cyclohexylpropanoyl}-Darginyl(N-guanidino-Tos)-O-resin was synthesized according to the method described in Example 1. The resin was washed with 10% diisopropylethylamine in methylene chloride (3×10 mL) and with methylene chloride (3×10 mL). 10% Diisopropylethylamine in methylene chloride (15 mL), followed by acetic anhydride (10 molar equivalents) were added and the reaction was permitted to proceed at room temperature until a Kaiser test showed negative. The obtained peptide resin was washed with methylene chloride (3×10 mL) and dried. This was treated with HF as described in Example 2 to yield N-alpha acetyl phenylalanyl-lysyl(N-epsilon-Fmoc)-ornithyl-{(2R)-2-amino-3-cyclohexylpropanoyl}-{(2S)-2-amino-3-cyclohexylpropanoyl}-Darginyl-OH. The obtained peptide (300 mg, 0.25 mmol) was dissolved in degassed DMF (150 mL) and cooled to −40° C. Diphenylphosphoryl azide (DPPA)(83 u, 0.3 mmol) and sodium bicarbonate (105 mg, 125 mmol) were added. The reaction was carried out at −40° C. for 2 d and at 0–5° C. for 2 d. After the solvent was removed, the residue was treated with 20% piperidine in DMF (10 mL), and the title compound was isolated by the method described in Example 2.

FAB+ MS: (M+H)+ =894 Amino Acid Anal.: Phe (0.98), Lys (0.98), Orn (1.05), Cha (2.15), Arg (1.27)

EXAMPLE 263 (SEQUENCE ID NO. 13)

H-Arginyl-{(2S)-2-Amino-3-cyclohexylpropanoyl}-Phenylalanyl-{(2S)-2-Amino-3-cyclohexylpropanoyl}-Lysyl-Leucyl-OH

FAB+ MS: (M+H)+ =869

EXAMPLE 264

(N-Methyl)Phenylalanyl-Lysyl-Prolyl-{2-Aminoindan-2-carbonyl}-{(2S)-2-Amino-3-cyclohexylpropanoyl}-DArginyl-OH The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892.

FAB+ MS: (M+H)+ =873

EXAMPLE 265

H-DPhenylglycyl-Lysyl-Prolyl-{(2R)-2-Amino-3-cyclohexylpropanoyl}-Phenylalanyl-DArginyl-OH FAB+ MS: (M+H)+ =833 Amino Acid Anal.: Phg (0.81), Phe (0.88), Cha (0.98), Lys (0.93), Arg (1.07), Pro (1.11)

EXAMPLE 266

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-OMe DArginine methyl ester hydrochloride (131 mg, 0.5 mmol) was coupled to N-Boc-(N-Methyl)Phenylalanyl-Lysyl(N-epsilon-Boc)         -Prolyl-{(2R)-2-Amino-3-cyclohexylpropanoyl}-{(2S)-2-Amino-3-cyclohexylpropanoyl}-OH (456 mg, 0.5 mmol), which was prepared with the methodology described in Example 322, with 1-(3-dimethylaminopropyl)-3-ethyl carbodiimide in 93% yield using the methodology described in: Luly, J. R.; BaMaung, N.; Soderquist, J.; Fung, A. K. L.; Stein, H.; Kleinert, H. D.; Marcotte, P. A.; Egan, D. A.; Bopp, B.; Merits, I.; Bolis, G.; Greer, J.; Perun, T. J.; Plattner, J. J. *J. Med. Chem.* 1988, 31, 2264–2276. Deprotection in 50% trifluoroacetic acid/methylene chloride followed by HPLC purification as described in Example 2 furnished the title compound in 60% yield.

FAB+ MS: (M+H)+ =881 Amino Acid Anal.: PheMe (0.80), Lys (0.98), Pro (1.00), Cha (1.84), Arg (1.00)

EXAMPLE 267

H-Phenylalanyl-DLysyl-{(2S)-2-Amino-3-cyclohexylpropanoyl}-{(2S)-2-Amino-3-cyclohexylproanoyl}-Leucyl-DAlanyl-Arginyl-OH    FAB+    MS: (M+H)+ =940 Amino Acid Anal.: Phe (0.97), Lys (0.93), Cha (2.03), Leu (1.09), Ala (0.98), Arg (1.03)

EXAMPLE 268

(N-Methyl)Phenylalanyl-Lysyl-Alanyl-{(2R)-2-Amino-3-cyclohexylpropanoyl}-Phenylalanyl-DArginyl-OH FAB+ MS: (M+H)+ =835 Amino Acid Anal.: PheMe (1.03), Lys (1.03), Ala (1.00), Cha (0.95), Phe (0.99), Arg (0.99)

EXAMPLE 269

(N-Methyl)Phenylalanyl-Lysyl-Prolyl-DAlanyl-Phenylalanyl-DArginyl-OH

FAB+ MS: (M+H)+ =779 Amino Acid Anal.: Pro (0.96), Ala (0.93), PheMe (0.98), Phe (1.07), Lys (0.97), Arg (1.07)

EXAMPLE 270

(N-Methyl)DPhenylalanyl-Lysyl-Alanyl-{(2S)-2-Amino-3-cyclohexylpropanoyl}-Alanyl-Leucyl-Arginyl-OH

FAB+ MS: (M+H)+ =872

EXAMPLE 271

(N-Methyl)Phenylalanyl-Lysyl-Prolyl-{(2R)-2-Amino-3-cyclohexylpropanoyl}-Phenylalanyl-{(2R/S)-2-Amino-3,3-cyclopropyl-3-phenylpropanoyl}-OH 1-Phenyl-1-cyclopropane methanol was oxidized with activated dimethylsulfoxide (Mancuso, A. J.; Huang, S-L.; Swern, D. *J. Org. Chem.* 1978, 43, 2480–2482). This ketone was converted to (2R/S) -2-amino-3,3-cyclopropyl-3-phenylpropanoic acid according to the procedure given in: Gaudry, R. *Can. J. of Res.* 1948, 26, Sec. B, 387: $^1$H NMR (CDCl$_3$, 300 MHz) δ1.08–1.12 (m, 3 H), 1.42 (m, 1 H), 3.51 (s, 1 H), 7.32–7.44 (m, 5 H); mass spectrum, m/e 192(M+H). (2R/S)-2-Amino-3,3-cyclopropyl-3-phenylpropanoic acid was coupled with N-Boc-(N-methyl)phenylalanyl-lysyl(N-epsilon-Boc)-prolyl-{ (2R)-2-amino-3-cyclohexylpropanoyl}-phenylalanyl-OH as described in Example 322. The diastereomeric pair were purified and separated in a combined yield of 52% by HPLC as described in Example 2.

FAB+ MS: (M+H)+ =878 Amino Acid Anal.: PheMe (0.89), Lys (0.99), Pro (1.01), Cha (1.03), Phe (1.06)

EXAMPLE 272

(N-Methyl)Phenylalanyl-Lysyl-Prolyl-{(2R)-2-Amino-3-cyclohexylpropanoyl}-Phenylalanyl-(2R/S)-2-Amino-3,3-cyclopropyl-3-phenylpropanoyl}-OH This compounds was prepared as described in Example 271.

FAB+ MS: (M+H)+ =878 Amino Acid Anal.: PheMe (1.00), Lys (0.98), Pro (1.01), Cha (1.11), Phe (1.14)

EXAMPLE 273

(N-Methyl)Phenylalanyl-Lysyl-Phenylalanyl-{(2R)-2-Amino-3-cyclohexylpropanoyl}-Phenylalanyl-DArginyl-OH FAB+ MS: (M+H)+ =911 Amino Acid Anal.: PheMe (1.05), Phe (2.00), Cha (0.94), Lys (0.95), Arg (1.05)

EXAMPLE 274

H-Phenylalanyl-Arginyl-Methionyl-Glutaminyl-Leucyl-Glycyl-Arginyl-OH

FAB+ MS: (M+H)+ =907

EXAMPLE 275

H-Phenylalanyl-Lysyl-Azaglycyl-{(2R)-2-Amino-3-cyclohexylpropanoyl}-Phenylalanyl-DArginyl-OH This peptide is prepared using methodology similar to that described in: Dutta, A. S.; Giles, M. B.; Williams, J. C. *J. Chem. Soc., Perkin Trans.* 1 1986, 1655–64;

Dutta, A. S.; Giles, M. B.; Gormley, J. J.; Williams, J. C.; Kusner, E. J. *J. Chem. Soc., Perkin Trans.* 1 1987, 111–120.

EXAMPLE 276

H-Lysyl-{(2R/S)-2-Amino-5-phenylpentanoyl}-{(2S)-2-Amino-3-cyclohexylpropanoyl}-Alanyl-Leucyl-DAlanyl-Arginyl-OH FAB+ MS: (M+H)+ =886 Amino Acid Anal.: Lys (0.96), hhPhe (0.83), Cha (0.98), Ala (2.00), Leu (1.05), Arg (1.01)

EXAMPLE 277

H-Lysyl-{(2R/S)-2-Amino-5-phenylpentanoyl}-{(2S)-2-Amino-3-cyclohexylpropanoyl}-Alanyl-Leucyl-DAlanyl-Arginyl-OH FAB+ MS: (M+H)+ =886 Amino Acid Anal.: Lys (1.01), hhPhe (0.85), Cha (0.97), Ala (1.98), Leu (1.04), Arg (1.00)

EXAMPLE 278

(N-Methyl)Phenylalanyl-Lysyl-Tyrosyl-{(2R)-2-Amino-3-cyclohexylpropanoyl}-{(2S)-2-Amino-3-cyclohexylpropanoyl}-DArginyl-OH FAB+ MS: (M+H)+ =933 Amino Acid Anal.: PheMe (1.24), Lys (0.99), Tyr (0.98), Cha (1.97), Arg (1.03)

EXAMPLE 279

(N-Methyl)Phenylalanyl-Lysyl-{2-Amino-2-methylpropanoyl}-{(2R)-2-Amino-3-cyclohexylpropanoyl}-Phenylalanyl-DArginyl-OH

FAB+ MS: (M+H)+ =849

EXAMPLE 280

N-Acetyl-Phenylalanyl-Lysyl-DOrnithyl-(2R)-2-Amino-3-cyclohexylpropanoyl}-{(2S)-2-Amino-3-cyclohexylpropanoyl}-DArginyl

The title compound was prepared in analogy to Example 262.

FAB+ MS: (M+H)+ =894 Amino Acid Anal.: Phe (0.94), Lys (0.95), Orn (1.00), Cha (1.91), Arg (1.11)

EXAMPLE 281

H-{(2S)-2-Amino-3-cyclohexylpropanoyl}-{(2S)-2-Amino-3-cyclohexylpropanoyl}-Lysyl-Leucyl-DAlanyl-Arginyl-OH

FAB+ MS: (M+H)+ =793

EXAMPLE 282

(N-Methyl)Phenylalanyl-Lysyl-Prolyl-{(2R)-2-Amino-3-cyclohexylpropanoyl}-{(2R/S)-o-Fluorophenylalanyl}-DPhenylalanyl-OH

FAB+ MS: (M+H)+ =870

EXAMPLE 283

(N-Methyl)Phenylalanyl-Lysyl-Prolyl-{(2R)-2-Amino-3-cyclohexylpropanoyl}-{(2R/S)-o-Fluorophenylalanyl}-DPhenylalanyl-OH

FAB+ MS: (M+H)+ =870

EXAMPLE 284

(N-Methyl)Phenylalanyl-Lysyl-Prolyl-{(2R)-2-Amino-3-cyclohexylpropanoyl}-Alanyl-DArginyl-OH FAB+ MS: (M+H)+ =785 Amino Acid Anal.: Ala (0.63), PheMe (0.97), Cha (0.89), Lys (0.98), Arg (0.97), Pro (1.04)

EXAMPLE 285

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-NHNH$_2$ Hydrazine (40 uL) was added to a methanolic (10 mL) solution of Boc-(N-Methyl) Phenylalanyl-Lysyl(N-epsilon-Boc)Prolyl-{(2R)-2-Amino-3-cyclohexylpropanoyl}-{(2S) -2-Amino-3-cyclohexylpropanoyl}-DArginyl-OCH3 (100 mg, 0.1 mmol). The reaction was complete after stirring at room temperature overnight. The volatiles were removed under reduced pressure and the Boc groups were removed with 50% trifluoroacetic acid in methylene chloride. Following HPLC purification as described in Example 2, the title compound was obtained in 67% yield.

FAB+ MS: (M+H)+ =881 Amino Acid Anal.: PheMe (0.82), Lys (0.98), Pro (1.04), Cha (1.89), Arg (0.98)

EXAMPLE 286

N-Acetyl-Phenylalanyl-Lysyl-Alanyl-{(2S)-2-Amino-3-cyclohexylpropanoyl}-Alanyl-Leucyl-DTyrosyl-NHNH$_2$

FAB+ MS: (M+H)+ =921

EXAMPLE 287

(N-Methyl)Phenylalanyl-Alanyl-Prolyl-{(2R)-2-Amino-3-cyclohexylpropanoyl}-Phenylalanyl-DArginyl-OH FAB+ MS: (M+H)+ =804 Amino Acid Anal.: PheMe (1.01), Ala (1.04), Pro (1.04), Cha (0.88), Phe (0.99), Arg (0.99)

EXAMPLE 288

H-Phenylalanyl-DLysyl-Alanyl-{(2R)-2-Amino-3-cyclohexylpropanoyl}-{(2S)-2-Amino-3-cyclohexylpropanoyl}-DArginyl-OH

FAB+ MS: (M+H)+ =827

EXAMPLE 289

H-Phenylalanyl-Lysyl-Alanyl-{(2S)-2-Amino-3-cyclohexylpropanoyl}-{(2S)-2-Amino-3-cyclohexylpropanoyl}-DLysyl-DArginyl-OH

FAB+ MS: (M+H)+ =955

EXAMPLE 290

{(2R/S)-2-Amino-5-phenylpentanoyl}-Lysyl-Prolyl-{(2R)-2-Amino-3-cyclohexylpropanoyl}-{(2S)-2-Amino-3-cyclohexylpropanoyl}-DArginyl-Glycyl

The compound was prepared in a manner identical to that as described for Example No. 257.

FAB+ MS: (M+H)+ =921 Amino Acid Anal.: Lys (0.94), Pro (1.02), Cha (1.84), Arg (1.01), Gly (1.03), hhPhe (0.81)

EXAMPLE 291

(N-Methyl)Phenylalanyl-Lysyl-Prolyl-DLeucyl-{(2S)-2-Amino-3-cyclohexylpropanoyl}-Arginyl-OH FAB+ MS: (M+H)+ =827 Amino Acid Anal.: PheMe (1.01), Leu (0.99), Cha (0.88), Lys (1.00), Arg (1.09), Pro (1.02)

EXAMPLE 292 (Sequency ID No. 15)

H-Phenylalanyl-Lysyl-Arginyl-Methionyl-Glutaminyl-Leucyl-Glycyl-OH

FAB+ MS: (M+H)+ =879

EXAMPLE 293 (Sequency ID No. 16)

H-Phenylalanyl-Lysyl-Alanyl-{(2S)-2-Amino-3-cyclohexylpropanoyl}-{(2S)-2-Amino-3-cyclohexylpropanoyl}-Leucyl-Arginyl-NHNH$_2$
FAB+ MS: (M+H)+ = 939

EXAMPLE 294

H-Phenylalanyl-Lysyl-Lysyl-{(2R)-2-Amino-3-cyclohexylpropanoyl}-{(2S)-2-Amino-3-cyclohexylpropanoyl}-DAlanyl-OH FAB+ MS: (M+H)+ = 799 Amino Acid Anal.: Phe (1.02), Lys (1.97), Cha (1.96), Ala (1.01)

EXAMPLE 295

(N-Methyl)Phenylalanyl-Lysyl-Prolyl-{(2R)-2-Amino-3-cyclohexylpropanoyl}-Phenylglycyl-DArginyl-OH FAB+ MS: (M+H)+ = 847 Amino Acid Anal.: Phg (1.01), PheMe (0.87), Cha (1.04), Lys (0.78), Arg (1.12), Pro (1.16)

EXAMPLE 296

Phenylalanyl-Lysyl-Prolyl-{(2R)-2-Amino-3-cyclohexylpropanoyl}-{(2S)-2-Amino-3-cyclohexylpropanoyl}-DArginyl

The title compound was prepared in analogy to Example 257.

FAB+ MS: (M+H)+ = 835 Amino Acid Anal.: Phe (0.98), Lys (1.01), Pro (1.11), Cha (1.95), Arg (1.02)

EXAMPLE 297

H-Phenylalanyl-Lysyl-Alanyl-{(2S)-2-Amino-3-cyclohexylpropanoyl}-Glycyl-Arginyl-OH
FAB+ MS: (M+H)+ = 731

EXAMPLE 298

(N-Methyl)Phenylalanyl-Lysyl-{2-Aminoindan-2-carbony}-{(2R)-2-Amino-3-cyclohexylpropanoyl}-{(2S)-2-Amino-3-cyclohexylpropanoyl}-DArginyl-OH The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892.

FAB+ MS: (M+H)+ = 929

EXAMPLE 299

(N-Methyl)Phenylalanyl-Norleucyl-Prolyl-{(2R)-2-Amino-3-cyclohexylpropanoyl}-Phenylalanyl-DArginyl-OH FAB+ MS: (M+H)+ = 846 Amino Acid Anal.: PheMe (1.00), Phe (0.93), Cha (0.92), Arg (1.00), Pro (1.07)

EXAMPLE 300

H-Glycyl-Lysyl-Prolyl-{(2R)-2-Amino-3-cyclohexylpropanoyl}-{(2R/S)-2-Amino-5-phenylpentanoyl}-DArginyl-OH
FAB+ MS: (M+H)+ = 785

EXAMPLE 301

H-Glycyl-Lysyl-Prolyl-{(2R)-2-Amino-3-cyclohexylpropanoyl}-(2R/S)-2-Amino-5-phenylpentanoyl}-DArginyl-OH
FAB+ MS: (M+H)+ = 785

EXAMPLE 302

H-Phenylalanyl-Gutamyl(NHNH$_2$)-Alanyl-{(2S)-2-Amino-3-cyclohexylpropanoyl}-{(2S)-2-Amino-3-cyclohexylpropanoyl}Leucyl -DArginyl -NHNH$_2$
FAB+ MS: (M+H)+ = 887

EXAMPLE 303

(N-Methyl)Phenylalanyl-{(2S)-2-Amino-6-[guanidino(N{2imidazolinyl}-N,N'-ethylene]-hexanoyl}-Prolyl-{(2R)-2-Amino-3-cyclohexylpropanoyl}-Phenylalanyl-DArginyl-OH (N-Methyl)Phenylalanyl-Lysyl-Prolyl-{(2R)-2-Amino-3-cyclohexylpropanoyl}-Phenylalanyl-DArginyl-OH.3HOAc was prepared as described in Examples 1 and 2. This peptide (100 mg, 0.1 mmol), used without HPLC purification, was dissolved in NaOH solution (1 N, 0.5 ml). The reaction mixture was diluted with acetone/water 2:1 ( 1.5 mL) and methylthioimidazoline hydroiodide (85 mg, 0.35 mmol) was added. The reaction mixture was stirred at 50° C. overnight. The acetone was then removed in vacuo, the resulting aqueous solution acidified to pH 3 with trifluoroacetic acid, and acetonitrile added to dissolve any material that may oil out of the solution. The mixture was purified by HPLC using conditions described in Example 2 to give the title compound (3.1 mg, 3% yield).

FAB+ MS: (M+H)+ = 998 Amino Acid Anal.: PheMe (0.99), Phe (0.85), Pro (1.02), Cha (0.97), Arg (1.14)

EXAMPLE 304

(N-Methyl)Phenylalanyl-{(2S)-2-Amino-6-(N$^{G'}$-phenylguanidinyl)-hexanoyl}-Prolyl-{(2R)-2-Amino-3-cyclohexylpropanoyl}-Phenylalanyl-DArginyl-OH (N-Methyl)Phenylalanyl-Lysyl-Prolyl-{(2R)-2-Amino-3-cyclohexylpropanoyl}-Phenylalanyl-DArginyl-OH.3 HOAc was prepared as described in Examples 1 and 2. This peptide (100 mg, 0.1 mmol), used without HPLC purification, was dissolved in sodium hydroxide solution (1 N, 0.5 mL). The reaction mixture was diluted with acetone/water 2:1 (1.5 mL) and (2-methyl-3-phenyl-2-thiopseudo-thiourea hydroiodide (103 mg, 0.35 mmol) was added. The reaction mixture was stirred at 50° C. overnight. The acetone was then removed in vacuo, the resulting aqueous solution acidified to pH 3 with trifluoroacetic acid, and acetonitrile added to dissolve any material that may oil out of the solution. The mixture was then purified by HPLC conditions as described in Example 2 to furnish the title compound (8 mg, 0.1% yield). FAB+ MS: (M+H)+ = 980 Amino Acid Anal.: PheMe (1.08), Phe (0.98), Pro (1.04), Cha (1.03), Arg (0.98)

EXAMPLE 305

(N-Methyl)Phenylalanyl-Lysyl(N-epsilon-trifluoroacetyl)-Prolyl-{(2R)-2-Amino-3-cyclohexylpropanoyl}-{(2S)-2-Amino-3-cyclohexylpropanoyl}-DArginyl-OH FAB+ MS: (M+H)+ = 963 Amino Acid Anal.: Pro (0.94), PheMe (1.18), Cha (1.75), Lys (1.01), Arg (1.11)

EXAMPLE 306

H-Lysyl-DPhenylalanyl-Alanyl-{(2S)-2-Amino-3-cyclohexylpropanoyl}-{(2S)-2-Amino-3-cyclohexylpropanoyl}-DArginyl-OH.
FAB+ MS: (M+H)+ = 827

EXAMPLE 307

(N-Methyl)Phenylalanyl-Lysyl-Glycyl-{(2R)-2-Amino-3-cyclohexylpropanoyl}-Phenylalanyl-DPhenylalanyl-OH FAB+ MS: (M+H)+ =812 Amino Acid Anal.: Gly (0.91), PheMe (1.10), Phe (2.09), Cha (0.99), Lys (1.05)

EXAMPLE 308

(N-Methyl)Phenylalanyl-Lysyl-Prolyl-{(2R)-2-Amino-3-cyclohexylpropanoyl}-{2-aminocyclohexanecarbonyl}-DArginyl-OH

FAB+ MS: (M+H)+ =839

EXAMPLE 309 (SEQUENCE ID NO. 18)

H-Phenylalanyl-Arginyl-Methionyl-Glutaminyl-Leucyl-Glycyl-OH

FAB+ MS: (M+H)+ =751

EXAMPLE 310

H-Phenylalanyl-Lysyl-Penicillaminyl*-{(2S)-2-Amino-3-cyclohexylpropanoyl}-{(2S)-2-Amino-3-cyclohexylpropanoyl}DCysteinyl*-Arginyl-OH

FAB+ MS: (M+H)+ =988

EXAMPLE 311

(N-Methyl)Phenylalanyl-Lysyl-Lysyl-{(2R)-2-Amino-3-cyclohexylpropanoyl}-{(2S)-2-Amino-3-cyclohexylpropanoyl}-DAlanyl-OH FAB+ MS: (M+H)+ =813 Amino Acid Anal.: PheMe (0.99), Lys (1.98), Cha (2.00), Ala (1.02)

EXAMPLE 312

(N-Methyl)Phenylalanyl-Lysyl-Prolyl-Phenylglycyl-Alanyl-DArginyl-OH

FAB+ MS: (M+H)+ =765 Amino Acid Anal.: Ala (0.60), Phg (1.00), PheMe (0.96), Lys (1.03), Arg (1.00), Pro (0.91)

EXAMPLE 313

H-Phenylalanyl-Lysyl-Prolyl-DAlanyl-{(2S)-2-Amino-3-cyclohexylpropanoyl}-DArginyl-OH FAB+ MS: (M+H)+ =771 Amino Acid Anal.: Phe (0.99), Lys (1.02), Pro (0.93), Ala (0.97), Cha (1.01), Arg (1.03)

EXAMPLE 314 (SEQUENCE ID NO. 19)

H-Phenylalanyl-Lysyl-Alanyl-{(2S)-2-Amino-3-cyclohexylpropanoyl}-{(2S)-2-Amino-3-cyclohexylpropanoyl}-Leucyl-Glycyl-OH

FAB+ MS: (M+H)+ =841

EXAMPLE 315

H-{2-Aminoindan-2-carbonyl}-Lysyl-Prolyl-{(2R)-2-Amino-3-cyclohexylpropanoyl}-{(2S)-2-Amino-3-cyclohexylpropanoyl}-DArginyl-OH The following literature procedure was used to prepare 2-aminoindan-2-carboxylic acid: Pinder, R. M.; Butcher, B. H.; Buxton, D. A.; Howells, D. J. *J. Med. Chem.* 1971, 14, 892.

FAB+ MS: (M+H)+ =865

EXAMPLE 316

(N-Methyl)Phenylalanyl-Lysyl-Prolyl-{(2R)-2-Amino-3-cyclohexylpropanoyl}-Norleucyl-DArginyl-OH

FAB+ MS: (M+H)+ =827

EXAMPLE 317

H-Phenylalanyl-Lysyl-Prolyl-{(2R)-2-Amino-3-cyclohexylpropanoyl}-{(2S)-2-Amino-3-cyclohexylpropanoyl}-DLysyl-OH FAB+ MS: (M+H)+ =825 Amino Acid Anal.: Pro (1.20), Phe (1.06), Cha (1.81), Lys (1.94)

EXAMPLE 318

H-Phenylalanyl-Lysyl-Alanyl-{(2S)-2-Amino-3-cyclohexylpropanoyl}-Alanyl-Leucyl-DArginyl-NHNH$_2$

FAB+ MS: (M+H)+ =872

EXAMPLE 319

(N-Methyl)Phenylalanyl-{Lysyl(N-epsilon-[N-(1,3-Diaminopropyl) carbonyl])}-Prolyl-{(2R)-2-Amino-3-cyclohexylpropanoyl}-Phenylalanyl-DArginyl-OH The peptide Boc-(N-Methyl)Phenylalanyl-Lysyl(-Fmoc)-Prolyl-{(2R)-2-Amino-3-cyclohexylpropanoyl}-Phenylalanyl-DArginyl (N-guanidino-Tos)-OResin was synthesized according to the protocol described in Example 1, and the Fmoc protecting group was removed by treatment of the peptide-resin with piperidine according to the method shown in: Stewart, J. M; Young, J. D. "Solid Phase Peptide Synthesis" 2nd edition; Pierce Chemical Co.: Rockford, Ill., 1984; p 83. The resin, Boc-(N-Methyl)Phenylalanyl-Lysyl-Prolyl-{(2R)-2-Amino-3-cyclohexylpropanoyl}-Phenylalanyl-DArginyl(N-guanidino-Tos)-OResin (2.42 g, ca 0.96 meq), was agitated overnight with a nitrogen stream in a solution of dicarbonyl imidazole (1.6 g in 30 mL dimethylformamide) to form the carbonylimidazole derivative of lysine. The resin was then washed with dimethylformamide followed by methylene chloride and finally dried in a vacuum oven at room temperature overnight. The modified peptide-resin (0.74 g, ca 0.25 meq) was swelled with dimethyl-formamide and the solvent removed by filtration. The resin was then agitated overnight with a nitrogen stream in a solution of propanediamine (0.21 mL, 2.5 mmol) in dimethylformamide (20 ml). The resin was removed by filtration, washed with dimethylformamide and methylene chloride, and dried by aspiration. The peptide was then cleaved from the resin by treatment with anhydrous HF and purified by HPLC as described in Example 2 to supply the title compound (20 mg, 7% yield).

FAB+ MS: (M+H)+ =961 Amino Acid Anal.: PheMe (0.90), Phe (0.90), Lys (0.55), Pro (1.10), Cha (0.87), Arg (1.06)

EXAMPLE 320

(N-Methyl)Phenylalanyl-Lysyl-Prolyl-DPhenylalanyl-Alanyl-DArginyl-OH

FAB+ MS: (M+H)+ =779 Amino Acid Anal.: Pro (1.02), Ala (0.72), PheMe (1.03), Phe (1.09), Lys (1.04), Arg (1.09)

EXAMPLE 321

H-DLysyl-Phenylalanyl-Alanyl-{(2S)-2-Amino-3-cyclohexylpropanoyl}-{(2S)-2-Amino-3-cyclohexylpropanoyl}-DArginyl-OH

FAB+ MS: (M+H)+ =827

EXAMPLE 322

(N-Methyl)Phenylalanyl-Lysyl-Prolyl-{(2R)-2-Amino-3-cyclohexylpropanoyl}-Phenylalanyl-{D-4-Nitro-phenylalanyl}-OH Commercially available D-phenylalanine methyl ester hydrochloride (12 g) was hydrogenated with 5% rhodium on carbon (1.2 g) in 250 mL of methyl alcohol to yield (2R)-2-amino-3-cyclohexyl propanoic acid methyl ester hydrochloride in 97% yield. This (5.0 g, 18.4 mmol) was coupled with Boc-L-proline (3.97 g, 18.4 mmole)by standard methods [(1-hydroxybenzotriazole monohydride (HOBt) (2.74 g, 20 mmol), N-methylmorpholine (NMM) (2.23 mL, 20 mmol) and 1-(3-dimethylaminopropyl-3-ethylcarbodiimide hydrochloride (EDC) (3.89 g, 20 mmol) as exemplified by the methods described in "Peptide Synthesis" Second Edition, Bodanszky, M; Klausner, Y. S. and Ondetti, M. A., (1976) in 71% yield. The Boc-group was cleaved with 4 N hydrochloric acid in dioxane, and the obtained prolyl-(2R) -2-amino-3-cyclohexylpropanoic acid methyl ester hydrochloride was reacted with N-alpha-Cbz-N-epsilon-Boc-lysine (quantitative yield) according to the method mentioned above. The N-alpha-Cbz group was removed by hydrogenolysis (20%-palladium on charcoal 10% w/w) in acetic acid-isopropanol, and the obtained product was coupled with Boc-(N-methyl)-phenylalanine by the above method to obtain N-Boc-(N-methyl) phenylalanyl-lysyl(N-epsilon-Boc)-prolyl-{(2R)-2-amino-3-cyclohexylpropanoic acid methyl ester} in quantitative yield. Finally, the methyl ester (7.33 g, 9.5 mmole) was cleaved by treatment with 1.5 molar equivalents of lithium hydroxide (598 mg, 14.25 mmol) in 115 mL of methanolwater (2:1) mixture to obtain N-Boc-(N-methyl)phenylalanyllysyl (N-epsilon-Boc)-prolyl-{(2R)-2-amino-3-cyclohexylpropanoic acid} in 83% yield.

FAB+ MS: (M+H)+ =758

N-Boc-(N-methyl)phenylalanyl-lysyl(N-epsilon-Boc)-propyl-{(2R)-2-amino-3-cyclohexylpropanoic acid (1.5 g, 2 mmol) was reacted with phenylalanine methyl ester hydrochloride in tetrahydrofuran by the mixed anhydride method (isobutylchloroformate and N-methylmorpholine) as exemplified by the methods described in "Peptide Synthesis", Second Edition, Bodanszky, M.; Klausner, Y. S. and Ondetti, M. A., (1976) to obtain N-Boc-(N-methyl)phenylalanyl-lysyl (N-epsilon-Boc)-prolyl-{(2R)-2-amino-3-cyclohexylpropanoyl-phenylalanine methyl ester in quantitative yield. The methyl ester (1.7 g, 1.8 mmole) was saponified with 1.5 equivalents of lithium hydroxide (160 mg, 2.7 mmole) in 20 mL of methanol and water (2:1) according to the procedure described above to yield N-Boc-(N-methyl)-phenylalanyl-lysyl(N-epsilon-Boc)-prolyl-{(2R)-2-amino-3-cyclohexylpropanoyl}-phenylalanyl-OH in 99% yield.

N-Boc-(N-Methyl)Phenylalanyl-Lysyl(N-epsilon-Boc)-Prolyl-{(2R)-2-Amino-3-cyclohexylpropanoyl}-Phenylalanyl-OH (0.18 mmol) was dissolved in 3 mL of methylene chloride at −20° C. and triethylamine (25 uL, 0.18 mmol) and isobutylchloroformate (25 uL, 0.18 mmol) were added. After D-4-nitrophenylalanine (0.3 mmol) in 1 mL of dimethylformamide containing triethylamine (41.8 uL, 0.3 mmol) was added, the reaction was carried out at 20° C. for 1 h and at room temperature for one overnight. Solvent was removed and the residue was dissolved in ethyl acetate which was washed with brine, 10% potassium hydrogen sulfate, brine and dried over magnesium sulfate. Solvent was removed and the residue was treated with 4 N hydrochloric acid in dioxane to yield a crude title compound. HPLC purification gave the pure title compound.

FAB+ MS: (M+H)+ =897

EXAMPLE 323

H-Phenylalanyl-Lysyl-Prolyl-DArginyl-{(2S)-2-Amino-3-cyclohexylpropanoyl}-DArginyl-OH FAB+ MS: (M+H)+ =856 Amino Acid Anal.: Phe (0.95), Cha (0.96), Lys (0.92), Arg (2.07), Pro (1.11)

EXAMPLE 324

H-Phenylalanyl-Arginyl-Methionyl-Glutaminyl-Leucyl-Glycyl-Alanyl-OH

FAB+ MS: (M+H)+ =822

EXAMPLE 325

H-Phenylalanyl-Lysyl-{(2S)-2-Amino-3-cyclohexylpropanoyl}-Alanyl-Leucyl-DAlanyl-Arginyl-OH FAB+ MS: (M+H)+ =858 Amino Acid Anal.: Phe (1.00), Lys (1.01), Cha (0.97), Ala (1.95), Leu (1.04), Arg (1.00)

EXAMPLE 326

H-Phenylalanyl-Alanyl-Lysyl-{(2R)-2-Amino-3-cyclohexylpropanoyl}-{(2S)-2-Amino-3-cyclohexylpropanoyl}-DArginyl-OH FAB+ MS: (M+H)+ =827 Amino Acid Anal.: Phe (1.00), Ala (0.99), Lys (0.99), Cha (1.94), Arg (1.03)

EXAMPLE 327

(N-Methyl)Phenylalanyl-Lysyl-Aspartyl-{(2R)-2-Amino-3-cyclohexylpropanoyl}-Phenylalanyl-DArginyl-OH

FAB+ MS: (M+H)+ =879

EXAMPLE 328

H-Phenylalanyl-Lysyl-Prolyl-{(2R)-2-Amino-3-cyclohexylpropanoyl}-Alanyl-DArginyl-OH FAB+ MS: (M+H)+ =771 Amino Acid Anal.: Phe (0.98), Lys (0.99), Pro (1.13), Cha (1.00), Ala (0.70), Arg (1.03)

EXAMPLE 329

H-Phenylalanyl-Lysyl-Alanyl-{(2S)-2-Amino-3-cyclohexylpropanoyl}-Alanyl-Glycyl-OH

FAB+ MS: (M+H)+ =646

EXAMPLE 330

(N-Methyl)Phenylalanyl-Lysyl-Prolyl-{(2R)-2-Amino-3-cyclohexylpropanoyl}-Phenylalanyl-DLysyl-OH FAB+ MS: (M+H)+ =833 Amino Acid Anal.: PheMe (0.67), Lys (1.94), Pro (1.04), Cha (0.98), Phe (1.03)

EXAMPLE 331

(N-Methyl)Phenylalanyl-Lysyl-Prolyl-{(2R)-2-Amino-3-cyclohexylpropanoyl}-Phenylalanyl-DTyrosyl-OH

FAB+ MS: (M+H)+ =868

EXAMPLE 332

H-Phenylalanyl-Lysyl(N-epsilon-trifluoroacetyl)-Prolyl-{(2R)-2-Amino-3-cyclohexylpropanoyl}-{(2S)-2-Amino-3-cyclohexylpropanoyl}-DArginyl-OH FAB+ MS: (M+H)+ =949 Amino Acid Anal.: Pro (0.84), Phe (1.15), Cha (1.95), Lys (0.99), Arg (1.08)

EXAMPLE 333

H-Phenylalanyl-Lysyl-Alanyl-{(2S)-2-Amino-3-cyclohexylpropanoyl}-{(2S)-2-Amino-3-cyclohexylpropanoyl}Valyl-DArginyl-OH

FAB+ MS: (M+H)+ =926

EXAMPLE 334

(N-Methyl)Phenylalanyl-{(2S)-2-Amino-6-acetamidinylhexanoyl}-Prolyl-{(2R)-2-Amino-3-cyclohexylpropanoyl}-Phenylalanyl-DArginyl-OH The peptide Boc-(N-Methyl)Phenylalanyl-Lysyl(Fmoc)-Prolyl-{(2R)-2-Amino-3-cyclohexylpropanoyl}-Phenylalanyl-DArginyl(N-guanidino-Tos)-OResin was synthesized according to the protocol described in Example 1, and the Fmoc protecting group was removed by treatment of the peptide-resin with piperidine according to the method shown in: Stewart, J. M.; Young, J. D."Solid Phase Peptide Synthesis", 2nd Edition; Pierce Chemical Co.: Rockford, Ill., 1984; p 83. The resin, Boc-(N-Methyl)Phenylalanyl-Lysyl-Prolyl-{(2R)-2-Amino-3-cyclohexylpropanoyl}-Phenylalanyl-DArginyl(N-guanidino-Tos)-OResin (0.6 g, .ca 0.25 meq) was suspended in a solution of diisopropyl-ethylamine (0.44 mL, 2.5 mmol) in dimethylformamide (8 mL). Methyl acetimidate hydrochloride (0.14 g, 1.25 mmol) was added and the suspension stirred gently for 24 h at 50° C. The resin was removed by filtration, washed with dimethylformamide (2 portions) and methylene chloride (2 portions), and dried by aspiration. The peptide was then cleaved from the resin by treatment with anhydrous HF and purified by HPLC as described in Example 2 to provide the title compound (131 mg, 46% yield).

FAB+ MS: (M+H)+ =902 Amino Acid Anal.: PheMe (0.81), Phe (0.97), Lys (0.37), Pro (1.13), Cha (0.88), Arg (1.03)

EXAMPLE 335

(N-Methyl)Phenylalanyl-Lysyl-Prolyl-{(2R)-2-Amino-4-phenylbutanoyl}-Alanyl-DArginyl-OH FAB+ MS: (M+H)+ =793 Amino Acid Anal.: Pro (1.05), Ala (0.73), PheMe (1.04), Cha (1.08), Lys (1.00), Arg (1.09)

EXAMPLE 336

H-Phenylalanyl-Lysyl-Alanyl-{(2S)-2-Amino-3-cyclohexylpropanoyl}-{(2S)-2-Amino-3-cyclohexylpropanoyl}-{(2R)-2-Amino-3-cyclohexylpropanoyl}-DArginyl-OH

FAB+ MS: (M+H)+ =980

EXAMPLE 337

(N-Methyl)Phenylalanyl-Lysyl-Prolyl-{(2R)-2-Amino-3-cyclohexylpropanoyl}-Phenylalanyl-{(R/S)-2Fluorophenylalanyl}-OH This compound was prepared in analogy to Example No. 322.

FAB+ MS: (M+H)+ =870

EXAMPLE 338

(N-Methyl)Phenylalanyl-Lysyl-Prolyl-{(2R)-2-Amino-3-cyclohexylpropanoyl}-Phenylalanyl-{(R/S)-2-Fluorophenylalanyl)-OH This compound was prepared in analogy to Example No. 322.

FAB+ MS: (M+H)+ =870

EXAMPLE 339

(N-Methyl)Phenylalanyl-Lysyl-(2-Naphthylalanyl)-{(2R)-2-Amino-3-cyclohexylpropanoyl}-Phenylalanyl-DArginyl-OH FAB+ MS: (M+H)+ =961 Amino Acid Anal.: PheMe (0.93), Phe (1.01), Cha (0.91), Lys (0.97), Arg (1.02)

EXAMPLE 340

(N-Methyl)Phenylalanyl-Lysyl-Prolyl-{(2R)-2-Amino-3-cyclohexylpropanoyl}-{(2S)-2-Amino-3-cyclohexylpropanoyl}-DAlanyl-OH FAB+ MS: (M+H)+ =782 Amino Acid Anal.: Phe (0.91), Lys (0.99), Pro (1.13), Cha (1.98), Ala (1.03)

EXAMPLE 341

H-Phenylalanyl-Lysyl-Alanyl-Alanyl-Leucyl-DAlanyl-Arginyl-OH FAB+ MS: (M+H)+ =776 Amino Acid Anal.: Phe (0.99), Lys (0.99), Ala (2.84), Leu (1.03), Arg (0.99)

EXAMPLE 342

(N-Methyl)Phenylalanyl-Lysyl-Prolyl-{(2R)-2-Amino-3-cyclohexylpropanoyl}-{(2S)-2-Amino-3-cyclohexylpropanoyl}-{(R/S) t-Butylalanyl}-OH

FAB+ MS: (M+H)+ =838

EXAMPLE 343

(N-Methyl)Phenylalanyl-Lysyl-Prolyl-{(2R)-2-Amino-3-cyclohexylpropanoyl}-{(2S)-2-Amino-3-cyclohexylpropanoyl}-{(R/S)t-Butylalanyl}-OH

FAB+ MS: (M+H)+ =838

EXAMPLE 344

(N-Methyl)Phenylalanyl-Lysyl-Prolyl-D{3-(2'-Thienyl)alanyl}-Phenylalanyl-DArginyl-OH

FAB+ MS: (M+H)+ =861

EXAMPLE 345

(N-Allyl)Phenylalanyl-Lysyl-Alanyl-{(2R)-2-Amino-3-cyclohexylpropanoyl}-{(2S)-2-Amino-3-cyclohexylpropanoyl}-DArginyl-OH

FAB+ MS: (M+H)+ =867

EXAMPLE 346

(N-Methyl)Phenylalanyl-Lysyl-Prolyl-{(2R)-2-Amino-3-cyclohexylpropanoyl}-{(2S)-2-Amino-3-cyclohexylpropanoyl}-DLysyl-OH FAB+ MS: (M+H)+ =839 Amino Acid Anal.: PheMe (0.67), Lys (1.98), Pro (1.02), Cha (1.94)

EXAMPLE 347

H-Phenylalanyl-Lysyl-Alanyl-{(2S)-2-Amino-3-cyclohexylpropanoyl}-Alanyl-Leucyl-Glycyl-OH

FAB+ MS: (M+H)+ =759

EXAMPLE 348

(N-Methyl)Phenylalanyl-Lysyl-Prolyl-{(2R)-2-Amino-3-cyclohexylpropanoyl}-{p-Iodophenylalanyl}-DPhenylalanyl-OH

FAB+ MS: (M+H)+ =978

EXAMPLE 349

(N-Methyl)Phenylalanyl-Seryl-Prolyl-{(2R)-2-Amino-3-cyclohexylpropanoyl}-Phenylalanyl-DArginyl-OH FAB+ MS: (M+H)+=820 Amino Acid Anal.: Ser (0.58), PheMe (1.06), Phe (0.98), Cha (0.94), Arg (1.03), Pro (1.02)

EXAMPLE 350

(N-Methyl)Phenylalanyl-Lysyl(N-epsilon-trifluoroacetyl)-Prolyl-{(2R)-2-Amino-3-cyclohexylpropanoyl}-Leucyl-DArginyl-OH FAB+ MS: (M+H)+=923 Amino Acid Anal.: Pro (0.99), PheMe (1.00), Leu (1.04), Cha (0.94), Lys (0.98), Arg (1.03)

EXAMPLE 351

H-Phenylalanyl-Lysyl-Alanyl-{(2S)-2-Amino-3-cyclohexylpropanoyl}-{(2S)-2-Amino-3-cyclohexylpropanoyl}-Arginyl-OH

FAB+ MS: (M+H)+=827

EXAMPLE 352

(N-Methyl)Phenylalanyl-Lysyl-Prolyl-{(2R)-2-Amino-3-cyclohexylpropanoyl}-{(2S)-2-Amino-3-cyclohexylpropanoyl}-{(R) -Phenylglycinyl}-OH (R)-Phenylglycine was converted to its benzyl carbamate with Cbz-Cl under Schotten-Baumann conditions (Greenstein, J. P.; Winitz, M. "Chemistry of the Amino Acids" 3rd ed; Robert E Krieger Publishing Co , Inc: Malabar, Fla., 1986; Vol. 2, p 891.) in 68% yield: mass spectrum, m/e 286(M+H). Conversion to the t-butyl ester was accomplished with isobutylene in dioxane in the presence of a catalytic amount of sulfuric acid in 78% yield. The Cbz group was removed by hydrogenation to give (R)-phenylglycine t-butyl ester in 78% yield: mass spectrum, m/e 208(M+H). This ester was reacted with N-Boc- (N-Methyl) Phenylalanyl-Lysyl (N-epsilon-Boc) -Prolyl-{(2R)-2-Amino-3-cyclohexylpropanoyl }-{(2S)-2-Amino-3-cyclohexylpropanoic acid} (prepared by the methodology described in Example 322) under the conditions described in Example 322. Following deprotection with 50% trifluoroacetic acid in methylene chloride, the title compound was obtained in 41% yield following HPLC purification as described in Example 2.

FAB+ MS: (M+H)+=844 Amino Acid Anal.: PheMe (0.77), Lys (0.97), Pro (1.03), Cha (1.94), Phg (0.96)

EXAMPLE 353

(N-Methyl)Phenylalanyl-Lysyl-Prolyl-DValyl-Phenylalanyl-DArginyl-OH

FAB+ MS: (M+H)+=807 Amino Acid Anal.: Pro (0.96), Val (1.05), PheMe (0.99), Phe (1.03), Lys (0.96), Arg (1.00)

EXAMPLE 354

H-Lysyl-Phenylalanyl-Alanyl-{(2R)-2-Amino-3-cyclohexylpropanoyl}-{(2S)-2-Amino-3-cyclohexylpropanoyl}-DArginyl-OH

FAB+ MS: (M+H)+=827

EXAMPLE 355

(N-Methyl)Phenylalanyl-Lysyl-Prolyl-DPhenylalanyl-{(2S)-2-Amino-3-cyclohexylpropanoyl}-DArginyl-OH FAB+ MS: (M+H)+=861 Amino Acid Anal.: PheMe (0.84), Phe (1.00), Cha (0.90), Lys (0.83), Arg (1.00), Pro (1.07)

EXAMPLE 356

(N-Benzyl)Prolyl-Lysyl-Prolyl-{(2R)-2-Amino-3-cyclohexylpropanoyl}-{(2S)-2-Amino-3-cyclohexylpropanoyl}-DArginyl-OH The trifluoroacetic acid salt of Prolyl-Lysyl(N-epsilon-Cbz)-Prolyl-{(2R)-2-Amino-3-cyclohexylpropanoyl}-{(2S)-2-Amino-3-cyclohexylpropanoyl}-DArginyl(N-guanidino-Tos)-OResin was prepared according to the procedure described in Example 1. The peptide-resin obtained (0.55 g) was washed with 10%-diisopropylethylamine (DIEA) in methylene chloride (3×15 mL) and methylene chloride (3×15 mL) and was suspended in DMF (15 mL, containing 1%-acetic acid). Benzaldehyde (10 equivalent mole) and sodium cyanoborohydride (10 equivalent mole) were added and reacted for 1 hr. After the resin obtained was washed with DMF (3×15 mL) and methylene chloride (3×15 mL), it was treated with HF and anisole and purified by HPLC, according to the procedure described in Example 2.

FAB+ MS: (M+H)+=893 Amino Acid Anal.: Lys (0.95), Pro (1.24), Cha (2.04), Arg (1.05)

EXAMPLE 357

H-Lysyl-Aspartyl-{(2S)-2-Amino-3-cyclohexylpropanoyl}-{(2S)-2-Amino-3-cyclohexylpropanoyl}-Leucyl-DArginyl-Arginyl-OH FAB+ MS: (M+H)+=993 Amino Acid Anal.: Lys (1.00), Asp (0.90), Cha (1.90), Leu (1.03), Arg (1.97)

EXAMPLE 358

(N-Methyl) Phenylalanyl-Lysyl-Prolyl-{(R/S) t-Butylalanyl-{(2S)-2-Amino-3-cyclohexylpropanoyl}-DArginyl-OH

FAB+ MS: (M+H)+=841

EXAMPLE 359

H-{3-(2'-Thienyl)alanyl}-Lysyl-Prolyl-D{3-(2'-Thienyl)alanyl}-Phenylalanyl-DArginyl-OH

FAB+ MS: (M+H)+=853

EXAMPLE 360

H-Phenylalanyl-Lysyl-Valyl-{(2R)-2-Amino-3-cyclohexylpropanoyl}-{(2S)-2-Amino-3-cyclohexylpropanoyl}-DArginyl-OH FAB+ MS: (M+H)+=855 Amino Acid Anal.: Val (0.99), Phe (0.89), Cha (2.07), Lys (0.93), Arg (1.12)

EXAMPLE 361

(N-Methyl)Phenylalanyl-Lysyl-Prolyl-{(2R)-2-Amino-3-cyclohexylpropanoyl}-{(2R/S)-p-Fluorophenylalanyl}-DPhenylalanyl-OH

FAB+ MS: (M+H)+=870

EXAMPLE 362

(N-Methyl)Phenylalanyl-Lysyl-Prolyl-{(2R)-2-Amino-3-cyclohexylpropanoyl}-{(2R/S)-p-Fluorophenylalanyl}-DPhenylalanyl-OH

FAB+ MS: (M+H)+=870

EXAMPLE 363

(N-Methyl)Phenylalanyl-Lysyl-Prolyl-{(2R)-2-Amino-3-cyclohexylpropanoyl}-{(2R)-2-Amino-3-cyclohexylpropanoyl}-{(R/S)-2-Benzyl-arginyl}-OH The preparation of this compound is described in Example 378.

FAB+ MS: (M+H)+ =957 PheMe(0.73), Lys (1.07), Pro (0.93), Cha (1.83)

EXAMPLE 364

(N-Methyl)Phenylalanyl-Lysyl-Prolyl-{(2R)-2-Amino-3-cyclohexylpropanoyl}-{(2R)-2-Amino-3-cyclohexylpropanoyl}-{(R/S)-2-Benzyl-arginyl}-OH The preparation of this compound is described in Example 378.

FAB+ MS: (M+H)+ =957 PheMe(0.74), Lys (1.00), Pro (1.00), Cha (1.87)

EXAMPLE 365

H-Phenylalanyl-Lysyl(N-epsilon-trifluoroacetyl)-Prolyl-{(2R)-2-Amino-3-cyclohexylpropanoyl}-Glutaminyl-DArginyl-OH FAB+ MS: (M+H)+ =924 Amino Acid Anal.: Glx (1.05), Pro (0.96), Phe (0.96), Cha (0.99), Lys (0.97), Arg (1.05)

EXAMPLE 366

H-Phenylalanyl-Lysyl-Alanyl-{(2S)-2-Amino-3-cyclohexylpropanoyl}-{(2S)-2-Amino-3-cyclohexylpropanoyl}-Leucyl-DLysyl-OH

FAB+ MS: (M+H)+ =912

EXAMPLE 367

(N-Methyl)Phenylalanyl-Lysyl-Prolyl-{(2R)-2-Amino-3-cyclehexylpropanoyl}-Phenylalanyl-{(R)-Phenylglycinyl}-OH The title compound was prepared in analogy to Example 352 in 38% yield.

FAB+ MS: (M+H)+ =838 Amino Acid Anal.: PheMe (0.73), Lys (0.98), Pro (1.01), Cha (0.93), Phe (1.01), Phg (1.00)

EXAMPLE 368

(N-Methyl)Phenylalanyl-Lysyl-Prolyl-{(2R)-2-Amino-3-cyclohexylpropanoyl}-{(2S)-2-Amino-3-cyclohexylpropanoyl}-Arginyl-OH FAB+ MS: (M+H)+ =867 Amino Acid Anal.: Pro (1.07), PheMe (1.02), Cha (1.94), Lys (0.99), Arg (1.07)

EXAMPLE 369

(N-Methyl)Phenylalanyl-Lysyl-{(2S)-2-Amino-4-pentenoyl}-{(2R)-2-Amino-3-cyclohexylpropanoyl}-Phenylalanyl-DArginyl-OH Commercially available L-2-amino-4-pentenoic acid is converted to its N-tert-butoxycarbonyl derivative using the methodology-described in: Keller, O.; Keller, W. E.; van Look, G.; Wersin, G. *Organic Syntheses* 1984, 63, 160–170. The N-protected amino acid is incorporated into the peptide under standard solid phase conditions as described in Examples 1 and 2.

EXAMPLE 370

H-Phenylalanyl-Lysyl-Alanyl-{(2R)-2-Amino-3-cyclohexylpropanoyl}-{(2S)-2-Amino-3-cyclohexylpropanoyl}-DArginyl-OH

FAB+ MS: (M+H)+ =827

EXAMPLE 371

(N-Methyl)(2R/S)(m-Fluoro)Phenylalanyl-Lysyl-Prolyl-{(2R)-2-Amino-3-cyclohexylpropanoyl}-Phenylalanyl-DArginyl-OH

FAB+ MS: (M+H)+ =879

EXAMPLE 372

(N-Methyl)(2R/S)(m-Fluoro)Phenylalanyl-Lysyl-Prolyl-{(2R)-2-Amino-3-cyclohexylpropanoyl}-Phenylalanyl-DArginyl-OH

FAB+ MS: (M+H)+ =879

EXAMPLE 373

(N-Methyl)DProlyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =817 Amino Acid Anal.: Lys (0.95), Pro (1.34), Cha (2.05), Arg (1.05)

EXAMPLE 374

H-Lysyl-{(2S)-2-Amino-4-phenylbutanoyl}-{(2S)-2-Amino-3-cyclohexylpropanoyl}-{(2S)-2-Amino-3-cyclohexylpropanoyl}-Leucyl-DAlanyl-Arginyl-OH FAB+ MS: (M+H)+ =954 Amino Acid Anal.: Lys (1.00), hPhe/Cha (2.90), Leu (1.04), Ala (0.98), Arg (0.98)

EXAMPLE 375

(N-Methyl)Phenylalanyl-Lysyl-Prolyl-{(2R)-2-Amino-3-cyclohexylpropanoyl}-{(RS)t-Butylalanyl-DArginyl-OH

FAB+ MS: (M+H)+ =841

EXAMPLE 376

H-{3-(2'-Thienyl)alanyl}-Lysyl-Prolyl-{(2R)-2-Amino-3-cyclohexylpropanoyl}-{3-(2'-Thienyl)alanyl}-DArginyl-OH

FAB+ MS: (M+H)+ =859

EXAMPLE 377

H-Phenylalanyl-Lysyl(N-epsilon-trifluoroacetyl)-Prolyl-DPhenylalanyl-{(2S)-2-Amino-3-cyclohexylpropanoyl)-DArginyl-OH FAB+ MS: (M+H)+ =943 Amino Acid Anal.: Pro (1.04), Phe (2.13), Cha (0.89), Lys (0.96), Arg (0.97)

EXAMPLE 378

(N-Methyl)Phenylalanyl-Lysyl-Prolyl-{(2R)-2-Amino-3-cyclohexylpropanoyl}-{(2S)-2-Amino-3-cyclohexylpropanoyl}-{(R/S) -2-Benzyl-arginyl}-OH (N-alpha-Boc, N-delta-Cbz) Ornithine was converted to its benzyl ester in 98% yield (mass spectrum, m/e 457 [M+H]) according to: Wang, S-S.; Gisin, B. F.; Winter, D. P.; Makojske, R.; Kulesha, I. D.; Tzougraki, C.; Meienhofer, J. *J. Org. Chem.* 1977, 42, 1286–1290. The Boc group was removed by treatment with 4 N hydrochloric acid in dioxane over 1 h. Benzylation on the alpha carbon was accomplished using a solid-liquid catalytic phase-transfer alkylation procedure: O'Donnell, M. J.; LeClef, B.; Rusterholz, D. B. *Tetrahedron Lett.* 1982, 23, 4259–4262. This supplied (R/S)-(N-delta-Cbz)-2-benzyl-ornithine benzyl ester in 75% yield: $^1$H NMR (CDCl3, 300 MHz) δ1,3 (m, 1 H), 1.6 (m, 2 H), 1.93 (m, 1 H), 2.25 (d, 1 H), 3.15 (m, 3 H), 4,8 (b. 1 H), 5.1 (m, 4 H), 7.05 (m, 2 H), 7.2 (m, 3 H), 7.35 (m, 10 H); mass spectrum, m/e 447 (M+H). The above compound was coupled in 41% yield using 1-(3-dimethyl-aminopropyl)-3-ethyl carbodiimide hydrochloride to N-Boc-(N-Methyl)Phenylalanyl-Lysyl (N-epsilon-Boc)-Prolyl-{(2R)-2-Amino-3-cyclohexylpropanoyl}-{(2S)-2-Amino-3-cyclohexylpropanoic acid} which was prepared by methodology described in Example 322: FAB+ MS: (M+H)+ =1339. The Cbz group and benzyl ester were cleaved hydrogenitically: Ram, S.; Ehrenkaufer, R. E. *Synthesis* 1988, 91–95. Guanidination of the delta amine of the ornithine residue was accomplished according to the procedure of Salvadori, S.; Sarto, G. P.; Tomatis, R. *Eur. J. Med. Chem.-Chim. Ther.* 1983, 18, 489–493. The Boc groups were removed with 50% trifluoroacetic acid in methylene chloride to supply the title compounds. Besides the diastereomeric pair created by coupling of racemic 2-benzylornithine, racemization occurred at the adjacent residue. The four compounds; Examples 378, 379, 363, and 364; were separated and purified by HPLC as described in Example 2.

FAB+ MS: (M+H)+ =957 PheMe(0.79), Lys (0.98), Pro (1.02), Cha (1.85)

EXAMPLE 379

(N-Methyl)Phenylalanyl-Lysyl-Prolyl-{(2R)-2-Amino-3-cyclohexylpropanoyl}-{(2S)-2-Amino-3-cyclohexylpropanoyl}-{(R/S)-2-Benzyl-arginyl}-OH The preparation of this compound is described in Example 378.

FAB+ MS: (M+H)+ =957 PheMe(0.79), Lys (0.99), Pro (1.01), Cha (1.88)

EXAMPLE 380

H-Phenylalanyl-Lysyl(N-epsilon-trifluoroacetyl)-Glycyl-{(2R)-2-Amino-3-cyclohexylpropanoyl}-{(2S)-2-Amino-3-cyclohexylpropanoyl}-DArginyl-OH FAB+ MS: (M+H)+ =909 Amino Acid Anal.: Gly (0.99), Phe (0.95), Lys (0.98), Arg (1.08)

EXAMPLE 381

H-Phenylalanyl-Lysyl-Alanyl-{(2S)-2-Amino-3-cyclohexylpropanoyl}-{(2S)-2-Amino-3-cyclohexylpropanoyl}-Leucyl-DOrnithyl-OH

FAB+ MS: (M+H)+ =898

EXAMPLE 382

(N-Methyl)Phenylalanyl-Lysyl-Prolyl-{(2R)-2-Amino-3-cyclohexylpropanoyl}-DPhenylalanyl-{(R/S)-2-Benzyl-arginyl}-OH This compound was prepared in analogy to Example 378

FAB+ MS: (M+H)+ =951 Amino Acid Anal.: PheMe (0.82), Lys (0.99), Pro (1.03), Cha (0.94), Phe (1.04)

EXAMPLE 383

(N-Methyl)Phenylalanyl-Lysyl-Prolyl-DPhenylalanyl-Phenylalanyl-DArginyl-OH

FAB+ MS: (M+H)+ =855

EXAMPLE 384

H-Phenylalanyl-Lysyl-DAlanyl-{(2S)-2-Amino-3-cyclohexylpropanoyl}-{(2S)-2-Amino-3-cyclohexylpropanoyl}-DArginyl-OH

FAB+ MS: (M+H)+ =827

EXAMPLE 385

H-{(2R/S)(m-Fluoro)Phenylalanyl}-Lysyl-Prolyl-{(2R)-2-Amino-3-cyclohexylpropanoyl}-Phenylalanyl-DArginyl-OH

FAB+ MS: (M+H)+ =865

EXAMPLE 386

(N-Methyl)Prolyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =817 Amino Acid Anal.: Lys (0.98), Pro (1.17), Cha (2.00), Arg (1.02)

EXAMPLE 387

(N-Methyl)Phenylalanyl-Lysyl-Prolyl-{(2R)-2-Amino-3-cyclohexylpropanoyl}-{3-(2'-Thienyl)alanyl}-DArginyl-OH

FAB+ MS: (M+H)+ =867

EXAMPLE 388

H-Phenylalanyl-Lysyl-Prolyl-{(2R)-2-Amino-3-cyclohexylpropanoyl}-Leucyl-DArginyl-OH FAB+ MS:(M+H)+ =943 Amino Acid Anal.: Pro (1.04), Phe (2.13), Cha (0.89), LyS (0.96), Arg (0.97) or Pro (1.01), Phe (1.94), Cha (01.01), Lys (0.93), Arg (1.12)

EXAMPLE 389

H-Phenylalanyl-Lysyl(N-epsilon-trifluoroacetyl)-Prolyl-{(2R)-2-Amino-3-cyclohexylpropanoyl}-Phenylalanyl-DArginyl-OH FAB+ MS: (M+H)+ =943 Amino Acid Anal.: Pro (0.82), Phe (2.03), Cha (1.04), Lys (1.02), Arg (1.10)

EXAMPLE 390

H-Phenylalanyl-Lysyl-Alanyl-{(2S)-2-Amino-3-cyclohexylpropanoyl}-{(2S)-2-Amino-3-cyclohexylpropanoyl}-Leucyl-DNorleucyl-OH

FAB+ MS: (M+H)+ =897

EXAMPLE 391

H-Lysyl-Phenylalanyl-DAlanyl-{(2S)-2-Amino-3-cyclohexylpropanoyl}-{(2S)-2-Amino-3-cyclohexylpropanoyl}-DArginyl-OH

FAB+ MS: (M+H)+ =827

EXAMPLE 392

(N-Benzyl)DProlyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =893 Amino Acid Anal.: Lys (0.93), Pro (1.24), Cha (2.14), Arg (1.07)

EXAMPLE 393

H-{3-(2'-Thienyl)alanyl}-Lysyl-Prolyl-{(2R)-2-Amino-3-cyclohexylpropanoyl}-Phenylalanyl-DArginyl-OH

FAB+ MS: (M+H)+ =853

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. A C5a anaphylatoxin activity modulating compound selected from the group consisting of

[Chemical structure diagrams showing formulas with labels A, B, D, E, G, J, L, Q and substituents R101, R201, R202, R210, R211, R220, R221, R230, R231, R301, R302, R310, R311, and (CH₂)ₙ group]

wherein
n is 0, 1 or 2;
A is $R_1$-$R_2$-$R_3$ where
$R_1$ is selected from the group consisting of
aryl,
lower alkyl,
arylalkyl, and
hydrogen;
$R_2$ is selected from the group consisting of
$>CR_{99}R_{100}$
where $R_{99}$ is selected from hydrogen, lower alkyl, and arylalkyl and $R_{100}$ is hydrogen or lower alkyl, and
oxygen, with the proviso that when $R_2$ is oxygen, $R_1$ cannot be hydrogen; and
$R_3$ is selected from the group consisting of $>C=O$ and $>CH_2$ with the proviso that when $R_3$ is $>CH_2$ then $R_2$ cannot be oxygen; or
$R_1$ and $R_2$ taken together represent hydrogen or aryl;
$R_1$, $R_2$, and $R_3$ taken together represent hydrogen, lower alkyl, alkenyl, arylalkyl or an N-terminal protecting group;
$R_{101}$ is selected from the group consisting of hydrogen, lower alkyl, arylalkyl, and alkenyl;
$R_{201}$, $R_{210}$, $R_{220}$, and $R_{230}$ are independently selected from the group consisting of
hydrogen
lower alkyl,
alkenyl,
aryl,
arylalkyl,
(cycloalkyl)alkyl,
aminoalkyl,
amidoalkyl,
amidinoalkyl,
hydroxyalkyl,
guanidinoalkyl,
carboxyalkyl,
(carboxyamido)alkyl,
(carboxyhydrazino)alkyl,
ureidoalkyl,
(heterocyclic)alkyl,
(thioalkoxy)alkyl, and
sulfhydrylalkyl;
$R_{202}$, $R_{211}$, $R_{221}$, $R_{231}$, $R_{302}$, and $R_{311}$ are independently selected from the group consisting of
hydrogen,
lower alkyl, and
arylalkyl, with the proviso that for $R_{302}$, arylalkyl is not 3-phenylpropyl;
$R_{301}$ is selected from the group consisting of
hydrogen,
lower alkyl,
alkenyl,
aryl,
arylalkyl,
(cycloalkyl)alkyl,
aminoalkyl where the amine nitrogen is unsubstituted,
amidoalkyl,
hydroxyalkyl,
guanidinoalkyl,
carboxyalkyl,
(carboxyamido)alkyl,
(carboxyhydrazino)alkyl,
ureidoalkyl,
(heterocyclic)alkyl,
(thioalkoxy)alkyl, and
sulfhydrylalkyl, with the provisos that when $R_{311}$ is hydrogen and $R_{310}$ is
3-guanidinopropyl such that residue L is L-arginyl, then
a) arylalkyl is limited to benzyl,
b) amidoalkyl may not be N-benzoylamidoalkyl,
c) (carboxyamido)alkyl may not be aniline amides of aspartyl residues, and
d) in (heterocyclic)alkyl, the heterocyclic moiety is separated from the α-carbon of the amino acid residue by one methylene unit;
$R_{310}$ is selected from the group consisting of
hydrogen
lower alkyl,
alkenyl,
aryl,
arylalkyl,
(cycloalkyl)alkyl,
aminoalkyl,
amidoalkyl,
amidinoalkyl,
hydroxyalkyl,
guanidinoalkyl,
(carboxyamido)alkyl,
(carboxyhydrazino)alkyl,
ureidoalkyl,
(heterocyclic)alkyl,
sulfhydrylalkyl; and
Q is $R_{25}$-$R_{26}$-$R_{27}$ where
$R_{25}$ is selected from the group consisting of oxygen and $>NR_{109}$ where $R_{109}$ is hydrogen, lower alkyl or arylalkyl;
$R_{26}$ is selected from the group consisting of
hydrogen,
lower alkyl,
arylalkyl, and >NR$_{110}$ where R$_{100}$ is hydrogen, lower alkyl, aryl, and arylalkyl, with the provisos that
a) when R$_{25}$ is oxygen, then R$_{26}$ is lower alkyl, and
b) when R$_{26}$ is hydrogen, lower alkyl or arylalkyl, then R$_{27}$ is absent; and R$_{27}$ is hydrogen or aryl, or R$_{26}$ and R$_{27}$, taken together, represent hydrogen with the proviso that when R$_{25}$ is oxygen, R$_{26}$ and R$_{27}$ taken together are hydrogen, lower alkyl, or arylalkyl.

2. A compound as defined by claim 1 wherein R$_{201}$ is selected from aryl or arylalkyl; and R$_{202}$ is selected from hydrogen or lower alkyl.

3. A compound as defined by claim 1 wherein R$_{210}$ is selected from the group consisting arylalkyl; aminoalkyl; guanidinoalkyl; and lower alkyl; and R$_{211}$ is selected from hydrogen or lower alkyl.

4. A compound as defined by claim 1 wherein R$_{301}$ is selected from the group consisting of lower alkyl; arylalkyl, wherein arylalkyl is limited to benzyl when L represents an L-arginyl residue; and (cycloalkyl)alkyl; and
R$_{302}$, is selected from hydrogen or lower alkyl.

5. A compound as defined by claim 1 wherein R$_{310}$ is selected from the group consisting of arylalkyl and guanidinoalkyl; and
R$_{311}$ is selected from hydrogen or lower alkyl.

6. A compound as defined by claim 1 wherein G and L are of the D- or unnatural configuration.

7. A compound as defined by claim 1 wherein R$_1$-R$_2$-R$_3$ taken together is independently selected from hydrogen, lower alkyl or acetyl.

8. A compound as defined by claim 1 selected from the group consisting of:
H-Phenylalanyl-Lysyl-Prolyl-DLeucyl-{(2S)-2-Amino-3-cyclohexylpropanoyl}DArginyl-OH;
(N-Methyl)Phenylalanyl-Lysyl-Prolyl-DTyrosyl-{(2S)-2-Amino-3-cyclohexylpropanoyl}-DArginyl-OH;
H-Phenylalanyl-Lysyl-Prolyl-DPhenylalanyl-{(2S)-2-Amino-3-cyclohexylpropanoyl}-DArginyl-OH;
(N-Methyl)Phenylalanyl-Lysyl-Prolyl-D(1-Naphthylalanyl)-Phenylalanyl-DArginyl-OH; and
(N-Methyl)Phenylalanyl-Lysyl-Prolyl-DPhenylalanyl-{(2S)-2-Amino-3-cyclohexylpropanoyl}-DArginyl-OH.

9. A compound as defined by claim 1 wherein G is {(2R)-2-amino-3-cyclohexylpropanoyl}and is selected from the group consisting of:
(N-Methyl)Phenylalanyl-Lysyl-Tyrosyl-{(2R)-2-Amino-3-cyclohexylpropanoyl}-Phenylalanyl-DArginyl-OH;
(N-Methyl)Phenylalanyl-Lysyl-Glutamyl-{(2R)-2-Amino-3-cyclohexylpropanoyl}-Phenylalanyl-DArginyl-OH;
(N-Methyl)Phenylalanyl-Lysyl-Lysyl-{(2R)-2-Amino-3-cyclohexylpropanoyl}-Phenylalanyl-DArginyl-OH;
(N-Methyl)Phenylalanyl-Lysyl-Prolyl-{(2R)-2-Amino-3-cyclohexylpropanoyl}-Naphthylalanyl)-DArginyl-OH;
(N-Methyl)Phenylalanyl-Lysyl-Prolyl-{(2R)-2-Amino-3-cyclohexylpropanoyl}-Phenylalanyl-DArginyl-OH;
H-Phenylalanyl-Lysyl-Prolyl-{(2R)-2-Amino-3-cyclohexylpropanoyl}-Phenylalanyl-DArginyl-OH;
(N-Methyl)Phenylalanyl-Lysyl-{(2R/S)-2-Amino-5-phenylpentanoyl}-{(2R)-2-Amino-3-cyclohexylpropanoyl}-Phenylalanyl-DArginyl-OH;
(N-Methyl)Phenylalanyl-Lysyl-Prolyl-{(2R)-2-Amino-3-cyclohexylpropanoyl}-Tryptophanyl-DArginyl-OH;
(N-Methyl)Phenylalanyl-Lysyl-Arginyl-{(2R)-2-Amino-3-cyclohexylpropanoyl}-Phenylalanyl-DArginyl-OH;
(N-Methyl)Phenylalanyl-Lysyl-Prolyl-{(2R)-2-Amino-3-cyclohexylpropanoyl}Phenylalanyl-DPhenylalanyl-OH;
(N-Methyl)Phenylalanyl-Lysyl-Tryptophanyl-{(2R)-2-Amino-3-cyclohexylpropanoyl}-Phenylalanyl-DArginyl-OH;
(N-Methyl)Phenylalanyl-Lysyl-Alanyl-{(2R)-2-Amino-3-cyclohexylpropanoyl}-Phenylalanyl-DArginyl-OH;
(N-Methyl)Phenylalanyl-Lysyl-Prolyl-{(2R)-2-Amino-3-cyclohexylpropanoyl}-Norleucyl-DArginyl-OH;
(N-Methyl)Phenylalanyl-Lysyl-Prolyl-{(2R)-2-Amino-3-cyclohexylpropanoyl}-Phenylalanyl-{(R)-Phenylglycinyl}-OH;
(N-Methyl)Phenylalanyl-Lysyl-{(2S)-2-Amino-4-pentenoyl}-{(2R)-2-Amino-3-cyclohexylpropanoyl}-Phenylalanyl-DArginyl-OH;
(N-Methyl)(2R/S)(3-F)Phenylalanyl-Lysyl-Prolyl-{(2R)-2-Amino-3-cyclohexylpropanoyl}-Phenylalanyl-DArginyl-OH; and
H-Phenylalanyl-Lysyl-Prolyl-{(2R)-2-Amino-3-cyclohexylpropanoyl}-Leucyl-DArginyl-OH.

10. A compound as defined by claim 1 wherein G is {(2R)-2-amino-3-cyclohexylpropanoyl} and J is {(2S)-2-amino-3-cyclohexylpropanoyl} and is selected from the group consisting of:
H-Phenylalanyl-Lysyl-Prolyl-{(2R)-2-Amino-3-cyclohexylpropanoyl}-{(2S)-2-Amino-3-cyclohexylpropanoyl}-DArginyl-OH;
H-{(R/S)-t-Butylalanyl-Lysyl-Prolyl-{(2R)-2-Amino-3-cyclohexylpropanoyl}-{(2s)-2-Amino-3-cyclohexylpropanoyl}-D-Arginyl-OH;
(N-Methyl)Phenylalanyl-Ornithyl-Prolyl-{(2R)-2-Amino-3-cyclohexylpropanoyll-{(2s)-2-Amino-3-cyclohexylpropanoyl}-DArginyl-OH;
(N,N-Dimethyl)Phenylalanyl-Lysyl-Prolyl-{(2R)-2-Amino-3-cyclohexylpropanoyl}-{(2S)-2-Amino-3-cyclohexylpropanoyl}-DArginyl-OH;
H-Phenylalanyl-Lysyl-Arginyl-{(2R)-2-Amino-3-cyclohexylpropanoyl}-{(2S)-2-Amino-3-cyclohexylpropanoyl}-DArginyl-OH;
H-Phenylalanyl-Arginyl-Prolyl-{(2R)-2-Amino-3-cyclohexylpropanoyl}-{(2S)-2-Amino-3-cyclohexylpropanoyl}-DArginyl-OH;
(N-Methyl)Phenylalanyl-Lysyl-Prolyl-{(2R)-2-Amino-3-cyclohexylpropanoyl}-(2-Naphthylalanyl)-DArginyl-OH;
H-Phenylalanyl-Lysyl-Lysyl-{~2R)-2-Amino-3-cyclohexylpropanoyl}-{(2S)-2-Amino-3-cyclohexylpropanoyl}-DArginyl-OH;
(N-Methyl)Phenylalanyl-Lysyl-Prolyl-{(2R)-2-Amino-3-cyclohexylpropanoyl~{(2S)-2-Amino-3-cyclohexylpropanoyl}-DTryptophanyl-OH;
(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-N-(Me)(Benzyl);

H-Phenylalanyl-Ornithyl-Prolyl-{(2R)-2-Amino-3-cyclohexylpropanoyl}-{(2S)-2-Amino-3-cyclohexylpropanoyl}-DArginyl-OH;

H-Phenylalanyl-Lysyl-Phenylalanyl-{(2R)-2-Amino-3-cyclohexylpropanoyl}-{(2S)-2-Amino-3-cyclohexylpropanoyl}-DArginyl-OH;

N-Acetyl-Phenylalanyl-Lysyl-Alanyl-{(2R)-2-Amino-3-cyclohexylpropanoyl}-{(2S)-2-Amino-3-cyclohexylpropanoyl}-DArginyl-OH;

H-Phenylalanyl-Lysyl-Leucyl-{(2R)-2-Amino-3-cyclohexylpropanoyl~-{~2S)-2-Amino-3-cyclohexylpropanoyl}-DArginyl-OH;

(N-Methyl)Phenylalanyl-Lysyl-Alanyl-{(2R)-2-Amino-3-cyclohexylpropanoyl}-{(2S)-2-Amino-3-cyclohexyl-propanoyl}-DArginyl-OH;

(N-Methyl)Phenylglycyl-Lysyl-Prolyl-{(2R)-2-Amino-3-cyclohexylpropanoyl}-{(2S)-2-Amino-3-cyclohexylpropanoyl~-DArginyl-OH;

(N-Methyl)Phenylalanyl-Lysyl-Prolyl-{(2R)-2-Amino-3-cyclohexylpropanoyl}-{(2S)-2-Amino-3-cyclohexylpropanoyl}-DArginyl-OH;

(N-Methyl)Phenylalanyl-Norleucyl-Prolyl-{(2R)-2-Amino-3-cyclohexylpropanoyl}-{(2S)-2-Amino-3-cyclohexyl-propanoyl}-DArginyl-OH;

H-Phenylalanyl-Lysyl-Arginyl-{(2R)-2-Amino-3-cyclohexylpropanoyl}-{(2S)-2-Amino-3-cyclohexylpropanoyl}-DAlanyl-OH;

(N-Methyl)Phenylalanyl-Lysyl-Tyrosyl-{(2R)-2-Amino-3-cyclohexylpropanoyl}-{(2S)-2-Amino-3-cyclohexylpropanoyl}-DArginyl-OH;

(N-Methyl)Phenylalanyl-Lysyl(N-epsilon-trifluoroacetyl)-Prolyl-{(2R )-2-Amino-3-cyclohexylpropanoyl}-{(2S)-2-Amino-3-cyclohexyl-propanoyl}-DArginyl-OH;

and H-Phenylalanyl-Lysyl-Alanyl-{(2R)-2-Amino-3-cyclohexylpropanoyl}-{(2S)-2-Amino-3-cyclohexylpropanoyl}-D-Arginyl-OH[; and (N-Benzyl)DProlyl-Lysyl-Prolyl-{(2R)-2-Amino-3-cyclohexylpropanoyl-~(2S)-2-Amino-3-cyclohexylpropanoyl}-DArginyl-OH].

---

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="XAA at position 4 is an L- cyclohexylalanyl residue"

( i x ) FEATURE:
        ( A ) NAME/KEY: Modified-site
        ( B ) LOCATION: 5
        ( D ) OTHER INFORMATION: /note="XAA at position 5 is an L- cyclohexylalanyl residue"

( x i ) SEQUENCE DESCRIPTION: SEQ ID NO:1:

Phe  Lys  Ala  Xaa  Xaa  Arg
    1                      5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="XAA at position 4 is an L- cyclohexylalanyl residue"

( x i ) SEQUENCE DESCRIPTION: SEQ ID NO:2:

Phe  Lys  Ala  Xaa  Leu  Arg
    1                      5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="XAA at position 4 is an
            L- cyclohexylalanyl residue"

( x i ) SEQUENCE DESCRIPTION: SEQ ID NO:3:

Phe  Lys  Phe  Xaa  Leu  Arg
    1                     5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="XAA at position 4 is an
            L- cyclohexylalanyl residue"

( i x ) FEATURE:
        ( A ) NAME/KEY: Modified-site
        ( B ) LOCATION: 5
        ( D ) OTHER INFORMATION: /note="XAA at position 5 is an
            L- cyclohexylalanyl residue"

( x i ) SEQUENCE DESCRIPTION: SEQ ID NO:4:

Phe  Lys  Ala  Xaa  Xaa  Leu  Arg
    1                     5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="XAA at position 4 is an
            L- cyclohexylalanyl residue"

( i x ) FEATURE:
        ( A ) NAME/KEY: Modified-site
        ( B ) LOCATION: 5
        ( D ) OTHER INFORMATION: /note="XAA at position 5 is an
            L- cyclohexylalanyl residue"

( x i ) SEQUENCE DESCRIPTION: SEQ ID NO:5:

Phe  Lys  Ala  Xaa  Xaa  Leu  Lys
    1                     5

( 2 ) INFORMATION FOR SEQ ID NO:6:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 5
    ( D ) OTHER INFORMATION: /note="XAA at position 5 is an
        L- cyclohexylalanyl residue"

( x i ) SEQUENCE DESCRIPTION: SEQ ID NO:6:

Phe Lys Ala Gly Xaa Leu Gly
1                 5

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /note="XAA at position 4 is an
        L- cyclohexylalanyl residue"

( i x ) FEATURE:
    ( A ) NAME/KEY: Modified-site
    ( B ) LOCATION: 5
    ( D ) OTHER INFORMATION: /note="XAA at position 5 is an
        L- cyclohexylalanyl residue"

( i x ) FEATURE:
    ( A ) NAME/KEY: Modified-site
    ( B ) LOCATION: 6
    ( D ) OTHER INFORMATION: /note="XAA at position 6 is an
        L-leucyl methyl ester residue"

( x i ) SEQUENCE DESCRIPTION: SEQ ID NO:7:

Phe Lys Ala Xaa Xaa Xaa
1                 5

( 2 ) INFORMATION FOR SEQ ID NO:8:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /note="XAA at position 4 is an
        L- cyclohexylalanyl residue"

( x i ) SEQUENCE DESCRIPTION: SEQ ID NO:8:

Phe Lys Ala Xaa Gly Leu Gly
1                 5

( 2 ) INFORMATION FOR SEQ ID NO:9:

( i ) SEQUENCE CHARACTERISTICS:
    ( A ) LENGTH: 7 amino acids
    ( B ) TYPE: amino acid
    ( C ) STRANDEDNESS: single (D) TOPOLOGY: linear (ii) MOLECULE TYPE: peptide (xi) SEQUENCE DESCRIPTION: SEQ ID NO:9:

Phe Lys Arg Arg Leu Gly Arg
1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="XAA at position 1 is an
            N- methylphenylalanyl residue"

(xi) SEQUENCE DESCRIPTION: SEQ ID NO:10:

Xaa Lys Pro Gly Phe Arg
1               5

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="XAA at position 1 is an
            N- methylphenylalanyl residue"

(ix) FEATURE:
        (A) NAME/KEY: Modified-site
        (B) LOCATION: 4
        (D) OTHER INFORMATION: /note="XAA at position 4 is an
            L- cyclohexylalanyl residue"

(ix) FEATURE:
        (A) NAME/KEY: Modified-site
        (B) LOCATION: 7
        (D) OTHER INFORMATION: /note="XAA at position 7 is an
            L-arginyl hydrazide residue"

(xi) SEQUENCE DESCRIPTION: SEQ ID NO:11:

Xaa Lys Ala Xaa Ala Leu Xaa
1               5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Phe Arg Met Arg Leu Gly Arg
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note="XAA at position 2 is an
            L- cyclohexylalanyl residue"

( i x ) FEATURE:
        ( A ) NAME/KEY: Modified-site
        ( B ) LOCATION: 4
        ( D ) OTHER INFORMATION: /note="XAA at position 4 is an
            L- cyclohexylalanyl residue"

( x i ) SEQUENCE DESCRIPTION: SEQ ID NO:13:

Arg Xaa Phe Xaa Lys Leu
1               5

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Phe Arg Met Gly Leu Gly Arg
1               5

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Phe Lys Arg Met Gln Leu Gly
1               5

( 2 ) INFORMATION FOR SEQ ID NO:16:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /note="XAA at position 4 is an
            L- cyclohexylalanyl residue"

( i x ) FEATURE:
        ( A ) NAME/KEY: Modified-site
        ( B ) LOCATION: 5
        ( D ) OTHER INFORMATION: /note="XAA at position 5 is an
            L- cyclohexylalanyl residue"

(i x) FEATURE:
    (A) NAME/KEY: Modified-site
    (B) LOCATION: 7
    (D) OTHER INFORMATION: /note="XAA at position 7 is an
        L-arginyl hydrazide residue"

(x i) SEQUENCE DESCRIPTION: SEQ ID NO:16:

Phe  Lys  Ala  Xaa  Xaa  Leu  Xaa
1                    5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 4
        (D) OTHER INFORMATION: /note="XAA at position 4 is an
            L- cyclohexylalanyl residue"

(x i) SEQUENCE DESCRIPTION: SEQ ID NO:17:

Phe  Lys  Ala  Xaa  Gly  Arg
1                    5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:18:

Phe  Arg  Met  Gln  Leu  Gly
1                    5

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 4
        (D) OTHER INFORMATION: /note="XAA at position 4 is an
            L- cyclohexylalanyl residue"

(i x) FEATURE:
        (A) NAME/KEY: Modified-site
        (B) LOCATION: 5
        (D) OTHER INFORMATION: /note="XAA at position 5 is an
            L- cyclohexylalanyl residue"

(x i) SEQUENCE DESCRIPTION: SEQ ID NO:19:

Phe  Lys  Ala  Xaa  Xaa  Leu  Gly
1                    5

(2) INFORMATION FOR SEQ ID NO:20:

(i) SEQUENCE CHARACTERISTICS:
        (A) LENGTH: 7 amino acids

```
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Phe  Arg  Met  Gln  Leu  Gly  Ala
    1                    5
```

( 2 ) INFORMATION FOR SEQ ID NO:21:

```
    ( i ) SEQUENCE CHARACTERISTICS:
            ( A ) LENGTH: 6 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Modified-site
            ( B ) LOCATION: 4
            ( D ) OTHER INFORMATION: /note="XAA at position 4 is an
                    L- cyclohexylalanyl residue"

( i x ) FEATURE:
            ( A ) NAME/KEY: Modified-site
            ( B ) LOCATION: 5
            ( D ) OTHER INFORMATION: /note="XAA at position 5 is an
                    L- cyclohexylalanyl residue"

( x i ) SEQUENCE DESCRIPTION: SEQ ID NO:21:

Phe  Lys  Ala  Xaa  Xaa  Arg
    1                    5
```

11. A method for modulating anaphylatoxin activity in a mammal in need of such treatment, comprising administering to the mammal a therapeutically effective amount of a compound of claim 1.

12. An anaphylatoxin modulating composition comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO.   : 5,386,011
DATED        : January 31, 1995
INVENTOR(S)  : Wiedeman et al.

It is certified that error appears in the above-indentified patent and that said Letters Patent is hereby corrected as shown below:

| | |
|---|---|
| COLUMN 2, LINE 60: | delete "T is selected" <br> insert --L is selected-- |
| COLUMN 15, LINE 57: | delete "Lysyl-Prolyl{(2-R)" <br> insert --Lysyl-Prolyl-{(2-R)-- |
| COLUMN 30, LINE 11: | delete "(SEQUENCE ID NO. 1)" |
| COLUMN 35, LINE 8: | delete "(SEQUENCE ID NO. 2)" |
| COLUMN 38, LINE 65: | delete "(SEQUENCE ID NO. 3)" |
| COLUMN 39, LINE 50: | delete "(110)," <br> insert --(1.10),-- |
| COLUMN 40, LINE 7: | delete "(SEQUENCE ID NO. 4)" |
| COLUMN 43, LINE 58: | delete "(SEQUENCE ID NO. 5)" |
| COLUMN 49, LINE 39: | delete "(SEQUENCE ID NO. 6)" |
| COLUMN 50, LINE 64: | delete "(SEQUENCE ID NO. 7)" |

UNITED STATES PATENT AND TRADEMARK OFFICE
CERTIFICATE OF CORRECTION

PATENT NO. : 5,386,011
DATED : January 31, 1995
INVENTOR(S) : Wiedeman et al.

It is certified that error appears in the above-indentified patent and that said Letters Patent is hereby corrected as shown below:

COLUMN 51, LINE 36:   delete "(SEQUENCE ID NO. 8)"

COLUMN 52, LINE 10:   delete "(SEQUENCE ID NO. 9)"

COLUMN 52, LINE 27:   delete "(SEQUENCE ID NO. 10)"

COLUMN 55, LINE 5:    delete "(SEQUENCE ID NO. 13)"

COLUMN 58, LINE 65:   delete "(SEQUENCE ID NO. 15)"

COLUMN 59, LINE 1:    delete "(SEQUENCE ID NO. 16)"

COLUMN 61, LINE 15:   delete "(SEQUENCE ID NO. 18)"

COLUMN 76, LINE 60:   delete "{~2R)"
                      insert --{(2R)--

COLUMN 76, LINE 64:   delete "~{(2S)"
                      insert -- }{(2S)--

UNITED STATES PATENT AND TRADEMARK OFFICE
CERTIFICATE OF CORRECTION

PATENT NO. : 5,386,011
DATED : January 31, 1995
INVENTOR(S) : Wiedeman et al.

It is certified that error appears in the above-indentified patent and that said Letters Patent is hereby corrected as shown below:

COLUMN 77, LINE 11:   delete "~-{~2S)"
                      insert -- }-{(2S)--

COLUMN 77, LINE 18:   delete "~"

COLUMN 78, LINE 18:   delete "~"

Signed and Sealed this

Sixteenth Day of July, 1996

Attest:

Attesting Officer

BRUCE LEHMAN
Commissioner of Patents and Trademarks